(12) United States Patent
Laurence et al.

(10) Patent No.: US 11,167,082 B2
(45) Date of Patent: Nov. 9, 2021

(54) DRIVE MECHANISMS FOR DRUG DELIVERY PUMPS

(71) Applicant: AMGEN INC., Thousand Oaks, CA (US)

(72) Inventors: Lawton Laurence, Phoenixville, PA (US); Paul F. Bente, IV, Wayne, PA (US); Mark A. Destefano, Collegeville, PA (US); Ian P. Dardani, Radnor, PA (US); Ian B. Hanson, Wayne, PA (US)

(73) Assignee: AMGEN INC., Thousand Oaks, CA (US)

( * ) Notice: Subject to any disclaimer, the term of this patent is extended or adjusted under 35 U.S.C. 154(b) by 917 days.

(21) Appl. No.: 15/554,731

(22) PCT Filed: Mar. 9, 2016

(86) PCT No.: PCT/US2016/021585
§ 371 (c)(1),
(2) Date: Aug. 31, 2017

(87) PCT Pub. No.: WO2016/145094
PCT Pub. Date: Sep. 15, 2016

(65) Prior Publication Data
US 2018/0085517 A1   Mar. 29, 2018

Related U.S. Application Data

(60) Provisional application No. 62/242,929, filed on Oct. 16, 2015, provisional application No. 62/201,456, (Continued)

(51) Int. Cl.
*A61M 5/145*      (2006.01)
*A61M 5/142*      (2006.01)
(Continued)

(52) U.S. Cl.
CPC .......... *A61M 5/1454* (2013.01); *A61M 5/145* (2013.01); *A61M 5/1452* (2013.01);
(Continued)

(58) Field of Classification Search
CPC ............ A61M 5/1454; A61M 5/14216; A61M 5/158; A61M 5/145; A61M 5/315; A61M 5/20; A61M 2005/1402; A61M 2005/1585
See application file for complete search history.

(56) References Cited

U.S. PATENT DOCUMENTS 4,668,220 A * 5/1987 Hawrylenko ....... A61M 5/1454
128/DIG. 1
8,517,991 B2 8/2013 Clemente
(Continued)

FOREIGN PATENT DOCUMENTS

CN   101340938 A   1/2009
CN   102078652 A   6/2011
(Continued)

OTHER PUBLICATIONS

Chinese Patent Application No. 201680021169, First Office Action, dated Feb. 3, 2020.
(Continued)

*Primary Examiner* — Nathan R Price
*Assistant Examiner* — John A Doubrava
(74) *Attorney, Agent, or Firm* — Marshall, Gerstein & Borun LLP

(57) ABSTRACT

A drive mechanism (100) for use with a drug container (50) in a drug pump, the drug container (50) having a barrel (58) and a plunger seal (60), including a tether, an electrical actuator (101) and a gear interface. Rotation of the gear interface is controlled by the actuator (101). A gear assembly rotationally engages with the gear interface. The gear assembly includes a main gear and a regulating mechanism.
(Continued)

Release of the tether is metered by the gear assembly through the regulating mechanism. A piston (110, 1110, 2110) is connected to the tether and is disposed in the barrel (58) and configured to translate axially within the container. A biasing member is disposed at least partially within the barrel (58) and is retained in an energized state between the piston (110, 1110, 2110) and drive housing, wherein the release of the tether controls the free expansion of the biasing member from its energized state and the axial translation of the piston (110, 1110, 2110).

8 Claims, 30 Drawing Sheets

Related U.S. Application Data filed on Aug. 5, 2015, provisional application No. 62/147,435, filed on Apr. 14, 2015, provisional application No. 62/134,226, filed on Mar. 17, 2015, provisional application No. 62/130,318, filed on Mar. 9, 2015.

(51) Int. Cl.
  *A61M 5/158* (2006.01)
  *A61M 5/168* (2006.01)
  *A61M 5/172* (2006.01)
  *A61M 5/162* (2006.01)
  *A61M 5/14* (2006.01)

(52) U.S. Cl.
  CPC ........ *A61M 5/14216* (2013.01); *A61M 5/158* (2013.01); *A61M 5/14566* (2013.01); *A61M 5/162* (2013.01); *A61M 5/168* (2013.01); *A61M 5/1684* (2013.01); *A61M 5/1685* (2013.01); *A61M 5/16804* (2013.01); *A61M 5/16877* (2013.01); *A61M 5/1723* (2013.01); *A61M 2005/1402* (2013.01); *A61M 2005/14208* (2013.01); *A61M 2005/14506* (2013.01); *A61M 2005/1585* (2013.01); *A61M 2205/18* (2013.01); *A61M 2205/276* (2013.01); *A61M 2205/33* (2013.01); *A61M 2205/3334* (2013.01); *A61M 2205/3584* (2013.01); *A61M 2205/50* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 8,603,026 | B2 | 12/2013 | Favreau |
| 8,603,027 | B2 | 12/2013 | Favreau |
| 2005/0197625 | A1 | 9/2005 | Haueter et al. |
| 2008/0051714 | A1 | 2/2008 | Moberg et al. |
| 2008/0319394 | A1 | 12/2008 | Yodfat et al. |
| 2011/0028897 | A1* | 2/2011 | Swan ................. A61M 5/1454 604/151 |
| 2011/0172603 | A1 | 7/2011 | Yodfat et al. |
| 2012/0123325 | A1 | 5/2012 | Kameyama |
| 2012/0172804 | A1* | 7/2012 | Plumptre .......... A61M 5/14566 604/154 |
| 2013/0060196 | A1 | 3/2013 | O'Connor et al. |
| 2013/0060233 | A1* | 3/2013 | O'Connor ......... A61M 5/14248 604/506 |
| 2013/0211370 | A1 | 8/2013 | Nzike et al. |
| 2014/0058353 | A1* | 2/2014 | Politis ................ A61M 5/158 604/506 |
| 2014/0236087 | A1 | 8/2014 | Alderete, Jr. et al. |

FOREIGN PATENT DOCUMENTS

| | | |
|---|---|---|
| CN | 103025370 A | 4/2013 |
| CN | 103228303 A | 7/2013 |
| CN | 103764200 A | 4/2014 |
| CN | 104129567 A | 11/2014 |
| CN | 104307071 A | 1/2015 |
| EP | 3028727 A1 | 6/2016 |
| JP | 2005-537112 A | 12/2005 |
| JP | 2010-527255 A | 8/2010 |
| WO | WO-2008/133702 A1 | 11/2008 |
| WO | WO-2008/142394 A1 | 11/2008 |
| WO | WO-2010/112377 A1 | 10/2010 |
| WO | WO-2011/156580 A1 | 12/2011 |
| WO | WO-2012/084033 A1 | 6/2012 |
| WO | WO-2012/103428 A2 | 8/2012 |
| WO | WO-2012/134589 A1 | 10/2012 |
| WO | WO-2013/033421 A2 | 3/2013 |
| WO | WO-2013/033467 A2 | 3/2013 |
| WO | WO-2014/036239 A2 | 3/2014 |
| WO | WO-2014/116274 A1 | 7/2014 |
| WO | WO-2015/027174 A1 | 2/2015 |
| WO | WO-2015/032784 A1 | 3/2015 |
| WO | WO-2016/141082 A1 | 9/2016 |
| WO | WO-2016/186706 A1 | 11/2016 |

OTHER PUBLICATIONS

International Search Report and Written Opinion, International Application No. PCT/US2016/021585, dated Sep. 12, 2017.
Australian Patent Application No. 2016229138, Examination Report No. 1, dated Oct. 31, 2019.
Japanese Patent Application No. 2017-547555, Notice of Rejection, dated Jan. 7, 2020.
European Patent Application No. 1671062737, Communication Pursuant to Article 94(3) EPC, dated Oct. 9, 2020.
Chinese Patent Application No. 201680021169, Second Office Action, dated Sep. 30, 2020.
International Search Report and Written Opinion, International Application No. PCT/US2016/021585, dated Oct. 5, 2016.
Eurasian Patent Application No. 201791983, Office Action, dated May 29, 2019.
Eurasian Patent Application No. 201791983, Office Action, dated Dec. 3, 2018.
European Patent Application No. 21157193, Extended European Search Report, dated Jun. 14, 2021.

* cited by examiner

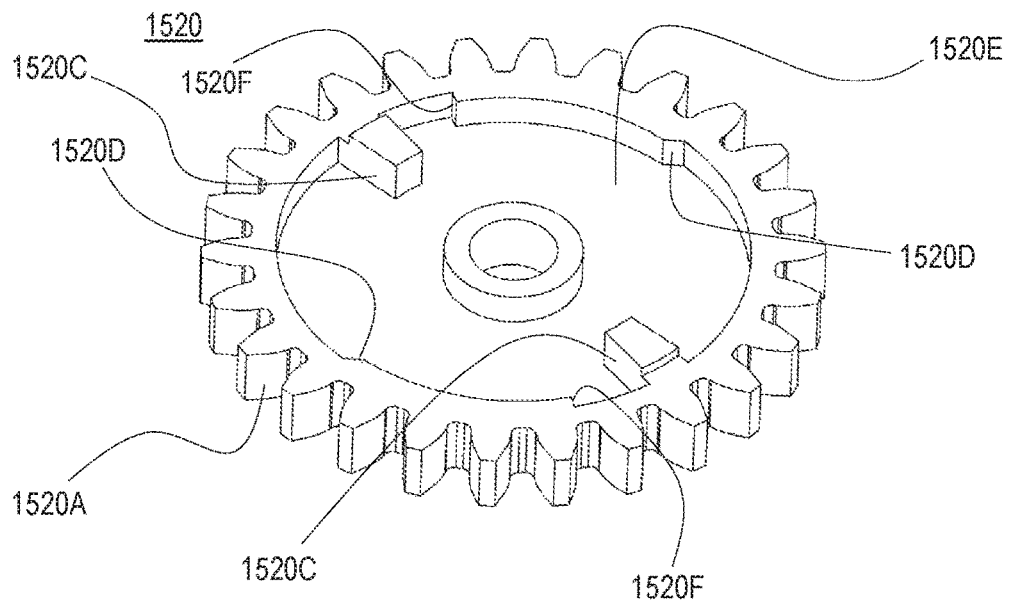
FIG. 22
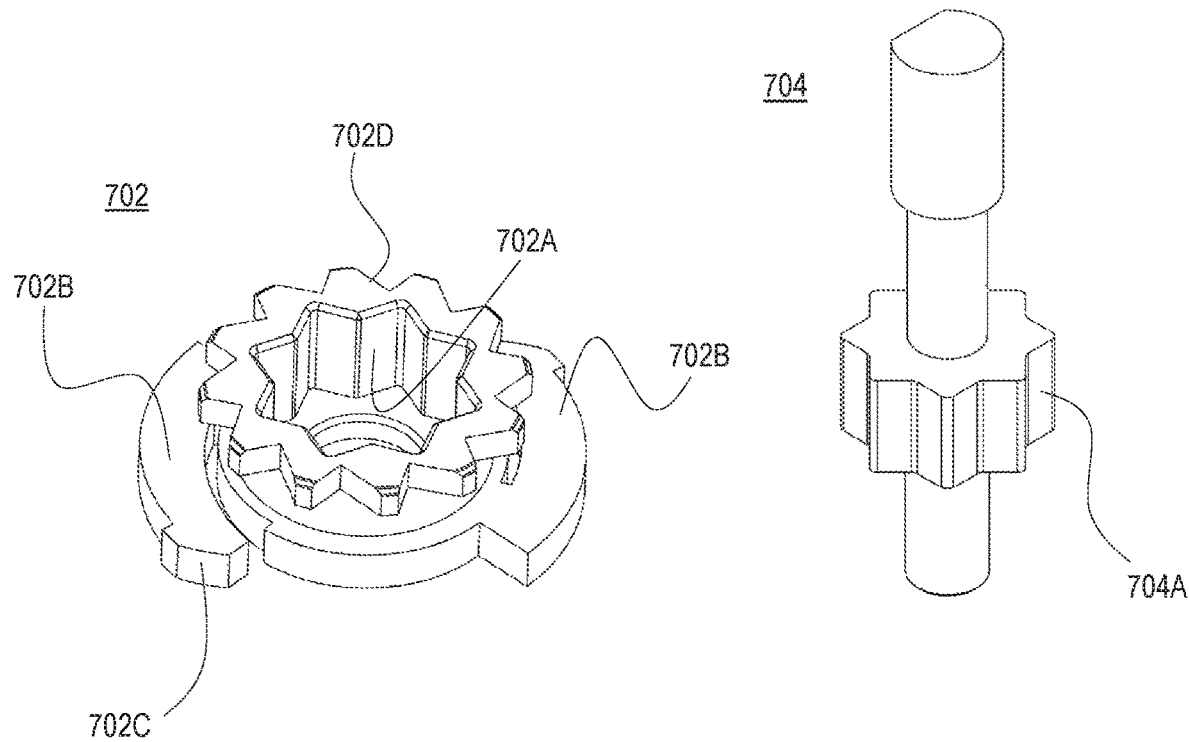
FIG. 23
FIG. 24

DRIVE MECHANISMS FOR DRUG DELIVERY PUMPS

CROSS-REFERENCE TO RELATED APPLICATIONS

This application is a United States national stage application of International Application No. PCT/US2016/021585, having an international filing date of Mar. 9, 2016, which claims priority to U.S. Provisional Application No. 62/130,318, filed on Mar. 9, 2015, U.S. Provisional Application No. 62/134,226, filed on Mar. 17, 2015, U.S. Provisional Application No. 62/147,435, filed on Apr. 14, 2015, U.S. Provisional Application No. 62/201,456, filed on Aug. 5, 2015, and U.S. Provisional Application 62/242,929, filed on Oct. 16, 2015, all of which are included by reference herein in their entireties for all purposes.

FIELD

THIS INVENTION relates to drug delivery pumps. More particularly, this invention relates to drive mechanisms for the controlled delivery of drug substances, controlled drug delivery pumps with such drive mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a target. More recently, parenteral delivery of liquid medicines into the body has been accomplished by administering bolus injections using a needle and reservoir, continuously by gravity driven dispensers, or via transdermal patch technologies. Bolus injections can imperfectly match the clinical needs of the target, and may require larger individual doses than are desired at the specific time they are given. Continuous delivery of medicine through gravity-feed systems compromises mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a target. These infusion devices have the ability to offer sophisticated fluid delivery profiles accomplishing bolus requirements, continuous infusion, and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injection pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides drive mechanisms for the controlled delivery of drug substances, controlled drug delivery pumps with such drive mechanisms, the methods of operating such devices, and the methods of assembling such devices. Notably, the drive mechanisms of the present invention enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a target; and (iii) connecting a sterile fluid pathway to a drug container to permit fluid flow from the drug container to the needle insertion mechanism for delivery to the target. The novel embodiments of the present invention thus are capable of delivering drug substances at variable rates. The drive mechanisms of the present invention may be pre-configurable or dynamically configurable, such as by control by the power and control system, to meet desired delivery rates or profiles, as explained in detail below. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. Because the end-of-dose indication is related to the physical end of axial translation and/or travel of one or more components of the drive mechanism, the drive mechanism and drug pump provide a true end-ofdose indication to the user. Through these mechanisms, confirmation of drug dose delivery can accurately be provided to the user or administrator. Accordingly, the novel devices of the present invention alleviate one or more of the problems associated with prior art devices, such as those referred to above.

In a first embodiment, the present invention provides a drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug pump into the target. A piston, and one or more biasing members, wherein the one or more biasing members are initially retained in an energized state and is configured to bear upon an interface surface of the piston, may also be incorporated in the drive mechanism. The piston is configured to translate substantially axially within a drug container having a plunger seal and a barrel. A tether is connected at one end to the piston and at another end to a winch assembly of a regulating mechanism, wherein the tether restrains the free expansion of the biasing member from its initial energized state and the free axial translation of the piston upon which the biasing member bears upon. The drug container may contain a drug fluid within a drug chamber for delivery to a target. Optionally, a cover sleeve may be utilized between the biasing member and the interface surface of the piston to hide the interior components of the barrel (namely, the piston and the biasing member) from view during operation of the drive mechanism. The tether is configured to be released from a winch assembly of a regulating mechanism of the drive mechanism to meter the free expansion of the biasing member from its initial energized state and the free axial translation of the piston upon which the biasing member bears upon.

Alternatively, the present invention provides a drive mechanism for utilization with a drug container in a drug pump, the drug container including a barrel and a plunger seal, including a tether, an electrical actuator, and a gear interface. Rotation of the gear interface is controlled by the electrical actuator. A gear assembly is in rotational engagement with the gear interface and includes a main gear and a regulating mechanism, wherein release of the tether is metered by operation of the gear assembly through the regulating mechanism. A drive housing is provided. A piston is connected to the tether and configured for disposition in the barrel adjacent the plunger seal. The piston is configured to translate substantially axially within the drug container and a biasing member is configured for disposition at least partially within the barrel, the biasing member being retained in an energized state between the piston and drive housing. The release of the tether controls the free expansion of the biasing member from its energized state and the free axial translation of the piston upon which the biasing member bears upon.

The present invention provides in other aspects a drug delivery pump, including a drive mechanism of any of the disclosed embodiments and a drug container including a barrel and a plunger seal, a needle insertion mechanism and a fluid pathway connection. The invention also may provide a safety mechanism configured to terminate or slow delivery of the drug fluid through the fluid pathway connection upon a loss of tension in the tether.

In yet another embodiment, the present invention provides a primable drive mechanism for utilization with a drug container in a drug pump, the drug container including a barrel and a plunger seal, including a tether, a drive housing, and a winch drum. A piston is connected to the tether and configured for disposition in the barrel adjacent the plunger seal, the piston configured to translate substantially axially within the drug container and a biasing member is configured for disposition at least partially within the barrel, the biasing member being retained in an energized state between the piston and drive housing. The tether is disposed and wound upon the winch drum and is configured to be released from the winch drum by rotation of the winch drum to meter the free expansion of the biasing member from its energized state and the free axial translation of the piston upon which the biasing member bears upon.

In at least one embodiment of the present invention, the regulating mechanism is a gear assembly driven by an actuator of the drive mechanism. The regulating mechanism retards or restrains the distribution of the tether, only allowing it to advance at a regulated or desired rate. This restricts movement of the piston within the barrel, which is pushed by one or more biasing members, hence controlling the movement of the plunger seal and delivery of the drug contained in the chamber. As the plunger seal advances in the drug container, the drug substance is dispensed through the sterile pathway connection, conduit, insertion mechanism, and into the target for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a gear coupled to a winch assembly upon which the tether may be releasably wound. Accordingly, rotation of the gear assembly initiated by the actuator may be coupled to winch assembly (i.e., through the gear assembly), thereby controlling the distribution of the tether, the rate of expansion of the biasing members and the axial translation of the piston, and the rate of movement of the plunger seal within the barrel to force a fluid from the drug chamber. The rotational movement of the winch assembly, and thus the axial translation of the piston and plunger seal, are metered, restrained, or otherwise prevented from free axial translation by other components of the regulating element, as described herein. Notably, the regulating mechanisms of the present invention do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the drive mechanisms of the present invention may concurrently or sequentially perform the steps of: triggering a needle insertion mechanism (NIM) to provide a fluid pathway for drug delivery to a target; and connecting a sterile fluid pathway to a drug container to permit fluid flow from the drug container to the needle insertion mechanism for delivery to the target. In at least one embodiment, initial motion by the actuator of the drive mechanism causes rotation of the main/star gear. In one manner, the main/star gear conveys motion to the regulating mechanism through the gear assembly. In another manner, the main/star gear conveys motion to the needle insertion mechanism through a gear. As the gear is rotated by the main/star gear, the gear engages the needle insertion mechanism to initiate the fluid pathway connection into the target, as described in detail above. In one particular embodiment, the needle insertion mechanism is a rotational needle insertion mechanism. Accordingly, the gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connection into the target, as described in detail herein.

In another embodiment, the drive mechanism may configure a NIM activation mechanism for activation by a user. For example, the NIM activation mechanism may be in an initial configuration in which depression of an actuation of an activation mechanism does not activate the NIM. The drive mechanism may subsequently transform the NIM activation mechanism to a configuration in which actuation of the activation mechanism does activate needle insertion. For example, actuation of the activation mechanism may cause translation of a slide. The drive mechanism may cause a selector member to be positioned such that contact between the slide and the selector member causes at least a portion of the slide to be displaced. This displacement brings the slide into contact with a throw arm which is caused to translate with the slide. This translation of the throw arm causes activation of needle insertion. For example, the throw arm may cause displacement of a NIM interlock which, in an initial configuration, prevents rotation of a NIM retainer. The NIM retainer initially prevents activation of needle insertion. After translation of the NIM interlock, an aperture of the NIM interlock is aligned with a portion of the NIM retainer, allowing rotation of the NIM retainer. This rotation allows activation of needle insertion.

In at least one embodiment, rotation of the needle insertion mechanism in this manner may also cause a connection of a sterile fluid pathway to a drug container to permit fluid flow from the drug container to the needle insertion mechanism for delivery to the target. Ramp aspect of needle insertion mechanism is caused to bear upon a movable connection hub of the sterile fluid pathway connection. As the needle insertion mechanism is rotated by the drive mechanism, a ramp aspect of the needle insertion mechanism bears upon and translates a movable connection hub of the sterile fluid pathway connection to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug pump. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present invention provides a drug delivery pump with controlled drug delivery. The drug delivery pump having a housing and an assembly platform, upon which an activation mechanism, an insertion mechanism, a fluid pathway connection, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch assembly of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a target. Optionally, a cover sleeve may be utilized between the biasing member and the interface surface of the piston to hide the interior components of the barrel (namely, the piston and the biasing member) from view during operation of the drive mechanism. The tether is configured to be released from a winch assembly of the delivery regulating mechanism to meter the free expansion of the biasing member from its initial energized state and the free axial translation of the piston upon which the biasing member bears upon.

In another embodiment, the drug pump further includes a gear assembly. The gear assembly may include a winch gear connected to a winch assembly upon which the tether may be releasably wound, rotation of the winch assembly releases the tether from the winch assembly to meter the free expansion of the biasing member from its initial energized state and the free axial translation of the piston upon which the biasing member bears upon. The metering of the tether controls the rate or profile of drug delivery to a target. The piston may be one or more parts and connects to a distal end of the tether. The winch assembly is coupled to a regulating mechanism which controls rotation of the winch assembly and hence metering of the translation of the piston.

In yet another embodiment, the drug pump may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug pump is configured to receive one or more inputs to meter the release of the tether by the winch assembly and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch assembly on the free axial translation of the piston upon which the biasing member bears upon to meet a desired drug delivery rate or profile, to change the dose volume for delivery to the target, and/or to otherwise start, stop, or pause operation of the drive mechanism.

In at least one embodiment of the present invention, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered, often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present invention, the delivery profile may be adjusted automatically based on one or more inputs. For example, the delivery profile may be adjusted based on activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the target. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the target. Accordingly, one or more embodiments of the present invention are capable of producing a change to the rate of medicament delivery from the drug container thereby providing a dynamic control capability to the drive mechanism and/or the drug delivery device.

The devices described herein may further include features which prevent the delivery of an excess volume of medicament or delivery at too rapid of a rate, e.g., to prevent a run-away condition of uncontrolled or undesired delivery of the medicament. By providing such automatic safety mechanisms, the safety of the target may be ensured. Some medicaments, such as insulin or other treatments for diabetes, can be dangerous, and potentially even deadly, if they are not delivered according to prescribed parameters. Such safety mechanisms can include a brake mechanism, a plunger seal piercing mechanism, and a plunger seal displacing mechanism, such as those described in detail herein. The safety features described below may ensure that delivery of the medicament is terminated if delivery deviates from the specified parameters.

The novel embodiments of the present invention provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. For example, the embodiments may include one or more batteries utilized to power the motor, drive mechanisms, and drug pumps of the present invention. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 22 is an isometric view of a winch gear of the embodiment of FIGS. 21A-21B;

FIG. 23 is an isometric view of a coupler of a winch drum of the embodiment of FIGS. 21A-21B;

FIG. 24 is an isometric view of a capstan of a winch drum of the embodiment of FIGS. 21A-21B;

DETAILED DESCRIPTION

Figure 1A:
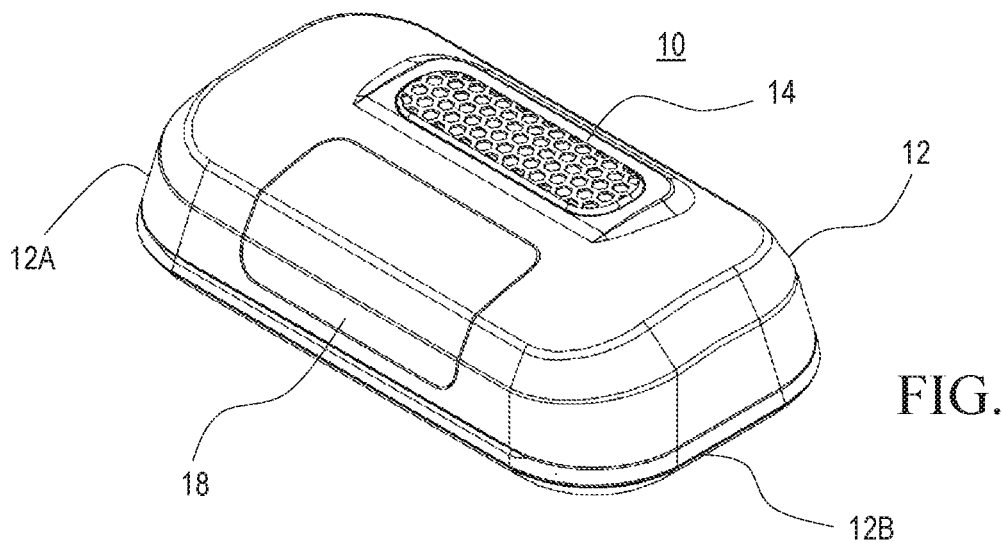
FIG. 1A is an isometric view of a drug delivery pump having a drive mechanism, according to one embodiment of the present invention (shown without the adhesive patch)

The present invention provides drive mechanisms for the delivery of drug substances and drug delivery pumps which incorporate such drive mechanisms. The drive mechanisms of the present invention may enable or initiate one or more functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a target; and (iii) connecting a sterile fluid pathway to a drug container to permit fluid flow from the drug container to the needle insertion mechanism for delivery to the target. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication.

The devices described herein may be configured for delivery of controlled substances and may further include features that prevent so-called "run-away" delivery of medicament. When delivering controlled substances, this may be an important safety feature to protect the target. For example, some medicaments, such as insulin, can be dangerous, and potentially even deadly, when administered in too large a quantity and/or at too rapid of a rate. By providing such automatic safety stop mechanisms, the safety of the target may be ensured.

As used herein to describe the drive mechanisms, drug delivery pumps, or any of the relative positions of the components of the present invention, the terms "axial" or "axially" refer generally to a longitudinal axis "A" around which the drug containers are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". Reference characters "A" and "D" appear in the drawings. As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present invention, the biasing member is a spring, preferably a compression spring.

The novel devices of the present invention provide drive mechanisms with integrated status indication and drug delivery pumps which incorporate such drive mechanisms. Such devices are safe and easy to use, and are aesthetically and ergonomically appealing. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, drive mechanisms, and their respective components are described further herein with reference to the accompanying figures.

Figure 1B:
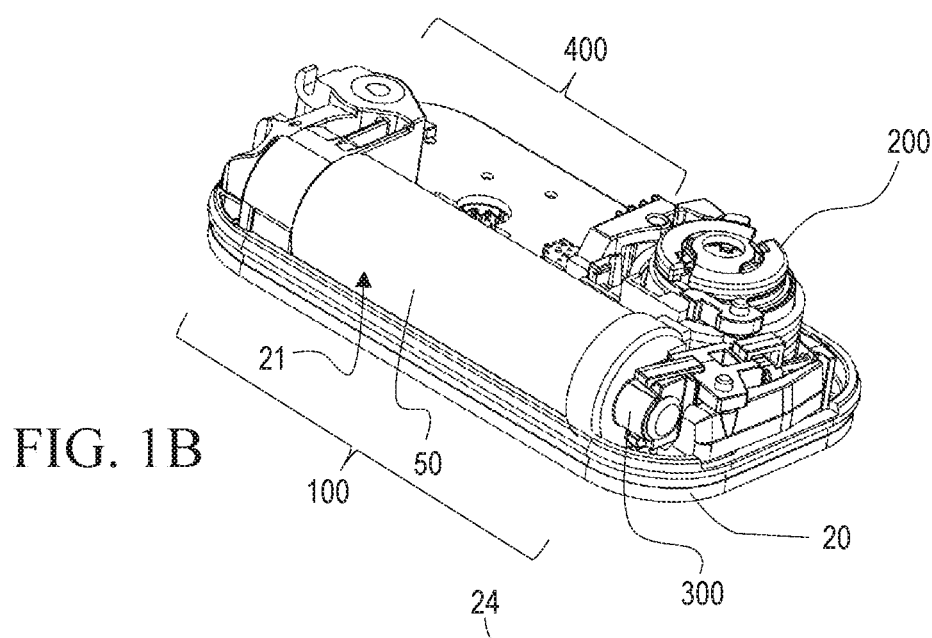
FIG. 1B is an isometric view of the interior components of the drug delivery pump shown in FIG. 1A (shown without the adhesive patch)
Figure 1C:
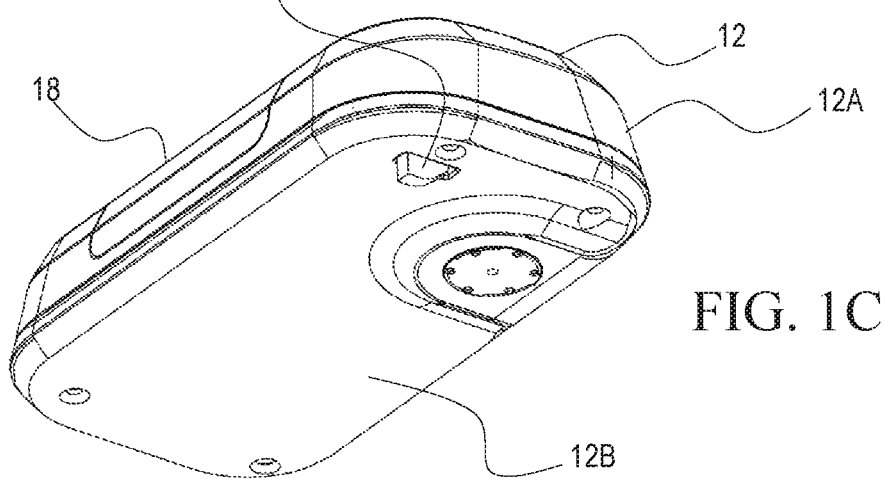
FIG. 1C is an isometric view of the drug delivery pump shown in FIG. 1A (shown without the adhesive patch) from yet another viewpoint.
Figure 2A:
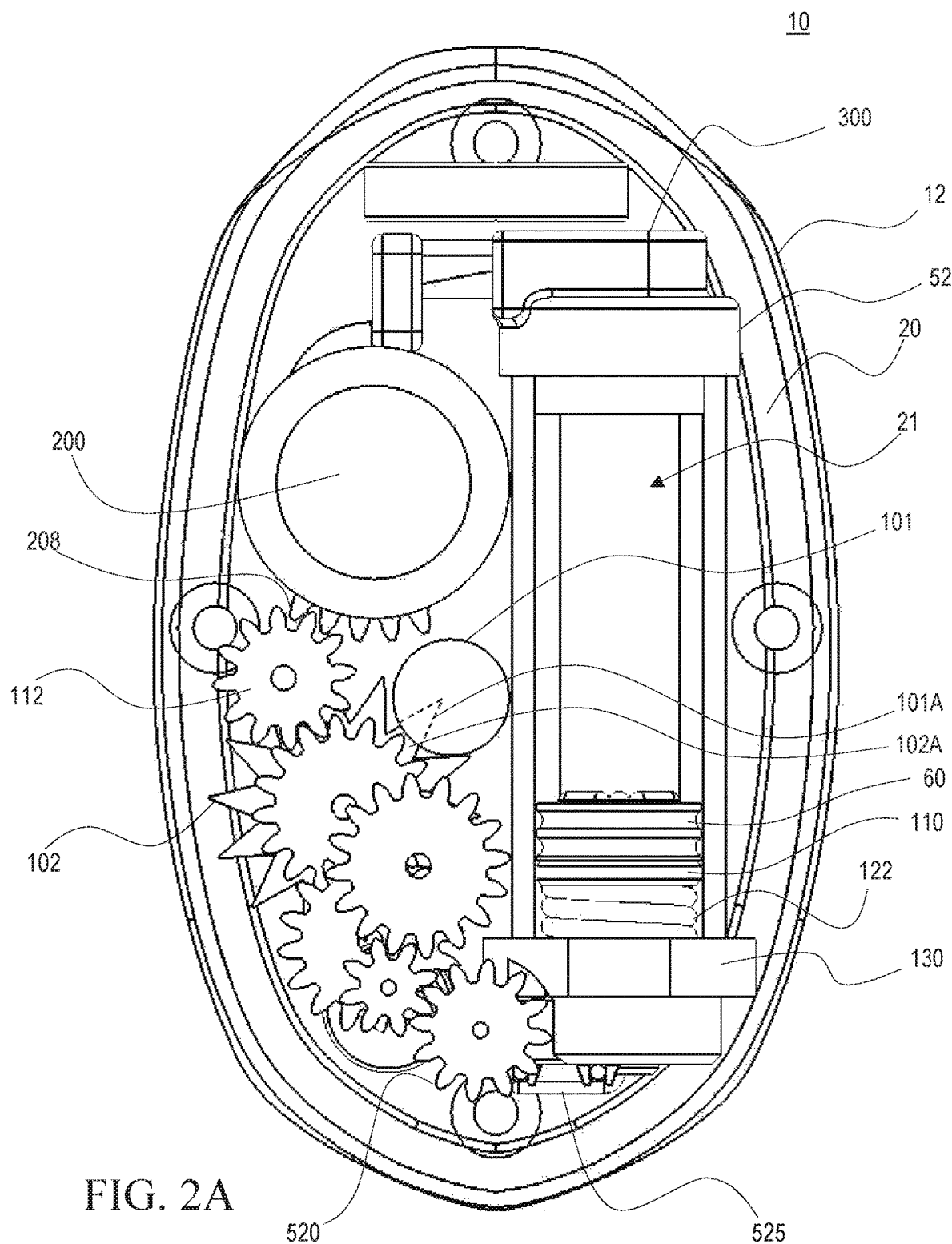
FIG. 2A is a top view, along an axis "A," of the interior components of an exemplary drug delivery pump.
Figure 2B:
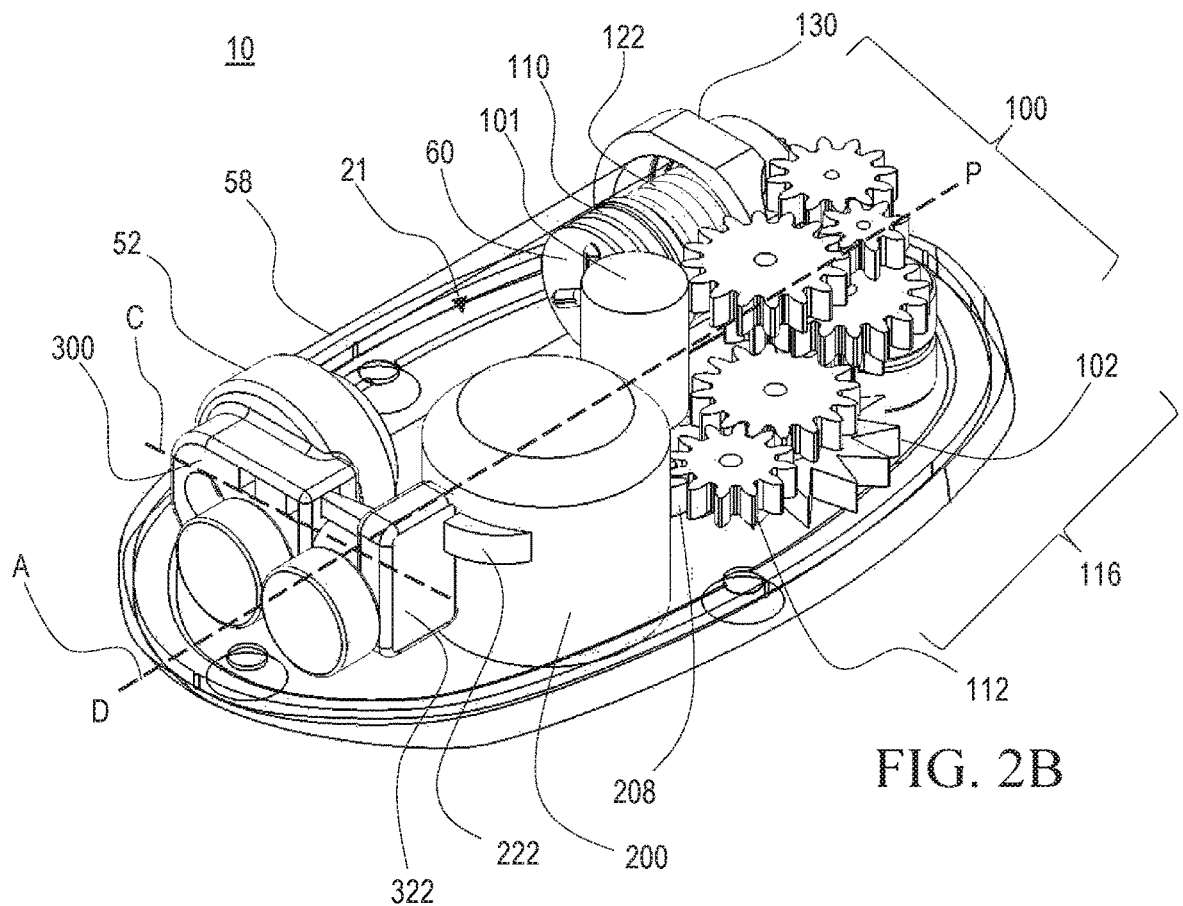
FIG. 2B is an isometric view of a drive mechanism, according to at least one embodiment of the present invention prior to activation.
Figure 2C:
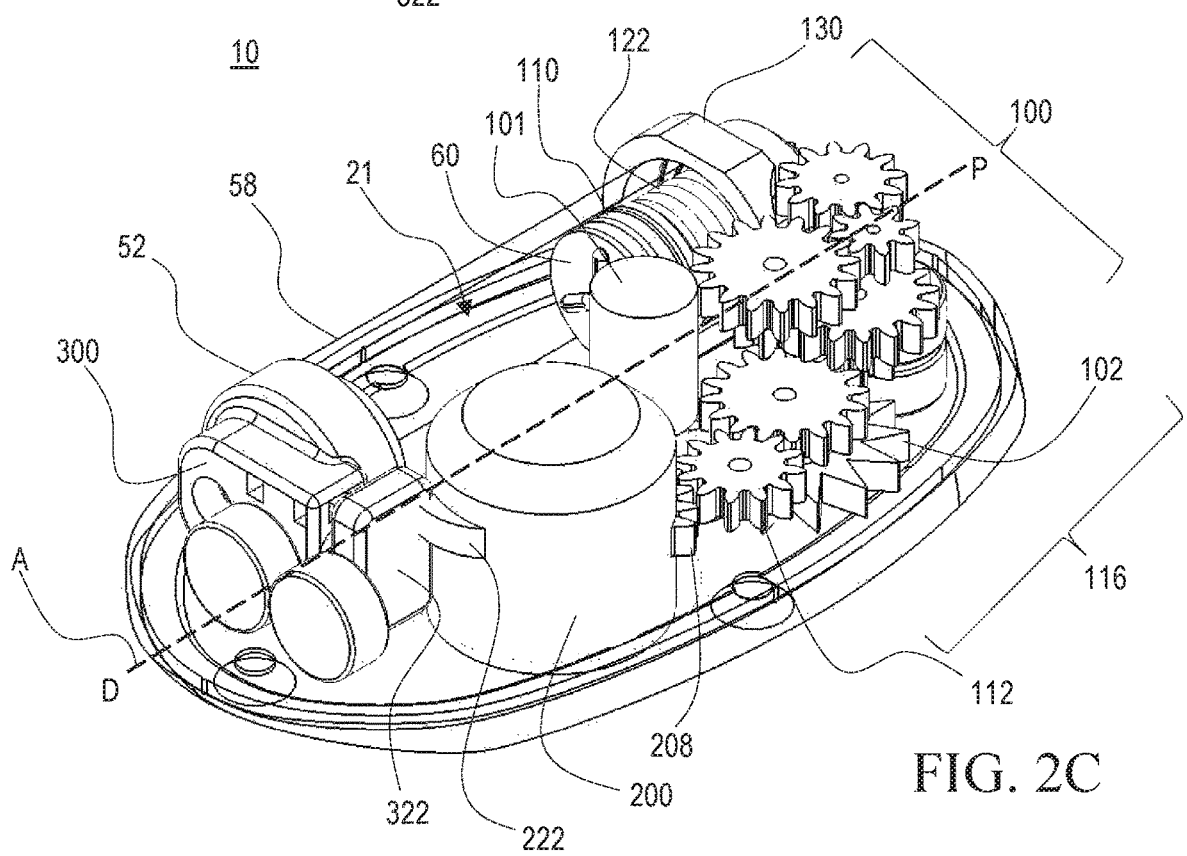
FIG. 2C is an isometric view of a drive mechanism, according to at least one embodiment of the present invention during activation.
Figure 2D:
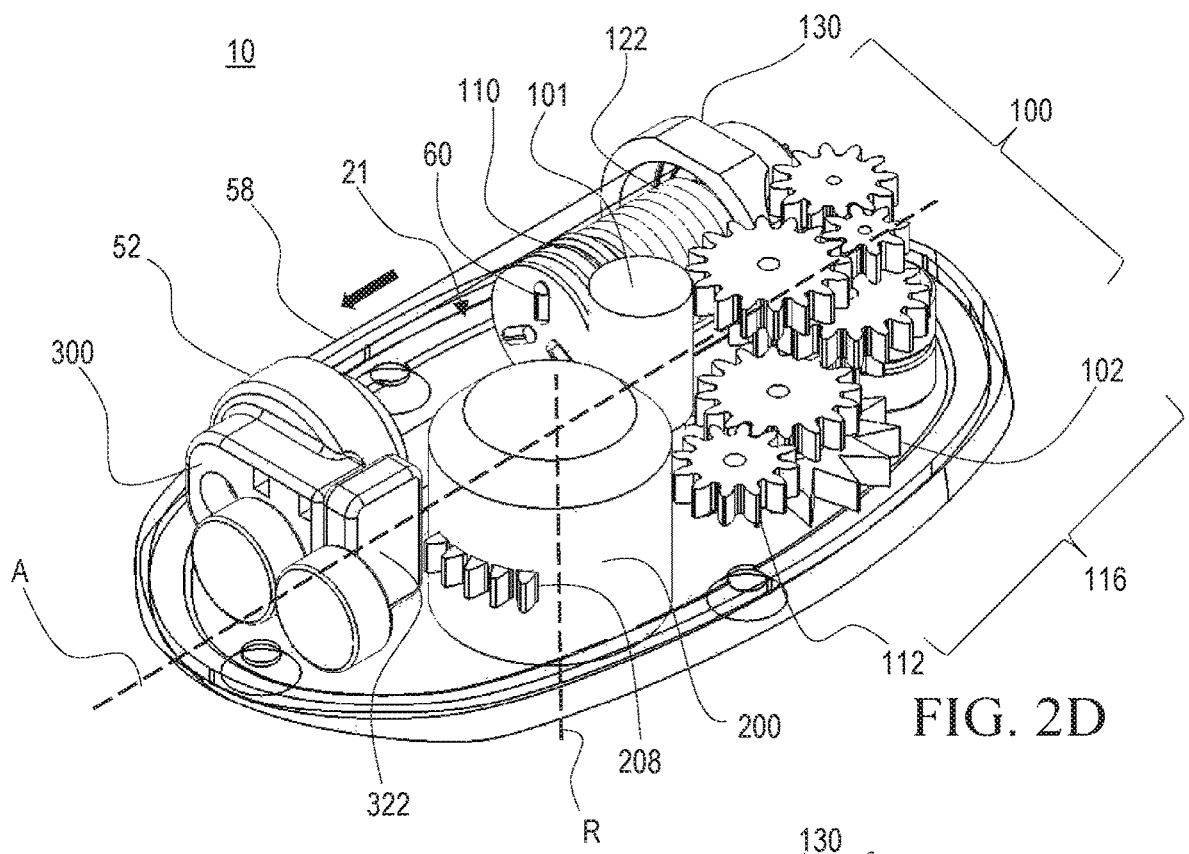
FIG. 2D is an isometric view of a drive mechanism, according to at least one embodiment of the present invention at a later stage during activation.

As used herein, the term "pump" is intended to include any number of drug delivery systems which are capable of dispensing a fluid to a target upon activation. Such drug delivery systems include, for example, injection systems, infusion pumps, bolus injectors, and the like. FIGS. 1A-2A show an exemplary drug delivery device according to at least one embodiment of the present invention. FIGS. 1B and 2A show the drug delivery device with the top housing removed so that the internal components are visible. The drug delivery device may be utilized to administer delivery of a drug treatment into a target. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which may include an upper housing 12A and a lower housing 12B. The pump housing 12 may include one or more tamper evidence features to identify if the drug delivery device has been opened or tampered with. For example, the pump housing 12 may include one or more tamper evidence labels or stickers, such as labels that bridge across the upper housing and the lower housing. Additionally or alternatively, the housing 12 may include one or more snap arms or prongs connecting between the upper housing and the lower housing. A broken or altered tamper evidence feature would signal to the user, the physician, the supplier, the manufacturer, or the like, that the drug delivery device has potentially been tampered with, e.g., by accessing the internal aspects of the device, so that the device is evaluated and possibly discarded without use by or risk to the user. The drug pump may further include an activation mechanism 14, a status indicator (not shown), and a window 18. The window 18 may be any translucent or transmissive surface through which the operation of the drug pump may be viewed. As shown in FIGS. 1B and 2A, drug pump 10 further includes assembly platform 20, drive mechanism 100 having drug container 50, insertion mechanism 200, fluid pathway connection 300, and a power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the target. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as one or more status indicators and windows, which may provide operation feedback to the user.

In at least one embodiment, the drug pump 10 provides an activation mechanism 14 that is displaced by the user to trigger the start command to the power and control system. In a preferred embodiment, the activation mechanism 14 is a start button that is located through the pump housing 12, such as through an aperture between upper housing 12A and lower housing 12B, and which contacts either directly or indirectly the power and control system 400. In at least one embodiment, the start button may be a push button, and in other embodiments, may be an on/off switch, a toggle, or any similar activation feature known in the art. The pump housing 12 also provides one or more status indicators and windows. In other embodiments, one or more of the activation mechanism 14, the status indicator, the window 18, and combinations thereof may be provided on the upper housing 12A or the lower housing 12B such as, for example, on a side visible to the user when the drug pump 10 is placed on the target. Housing 12 is described in further detail hereinafter with reference to other components and embodiments of the present invention.

Drug pump 10 is configured such that, upon activation by a user by depression of the activation mechanism, the drive mechanism is activated to perform one or more of the following functions: insert a fluid pathway into the target; enable, connect, or open necessary connections between a drug container, a fluid pathway, and a sterile fluid conduit; and force drug fluid stored in the drug container through the fluid pathway and fluid conduit for delivery into a target. In at least one embodiment, such delivery of drug fluid into a target is performed by the drive mechanism in a controlled manner. One or more optional safety mechanisms may be utilized, for example, to prevent premature activation of the drug pump. For example, an optional on-body sensor 24 may be provided in one embodiment as a safety feature to ensure that the power and control system, or the activation mechanism, cannot be engaged unless the drug pump 10 is in contact with the target. In one such embodiment, the on-body sensor is located on the bottom of lower housing 12B where it may come in contact with the target. Upon displacement or activation of the on-body sensor 24, depression of the activation mechanism is permitted. Accordingly, in at least one embodiment the on-body sensor is a mechanical safety mechanism, such as for example a mechanical lock out, that prevents triggering of the drug pump 10 by the activation mechanism. In another embodiment, the on-body sensor may be an electro-mechanical sensor such as a mechanical lock out that sends a signal to the power and control system to permit activation. In still other embodiments, the on-body sensor can be electrically based such as, for example, a conductive, capacitive- or impedance-based sensor which must detect tissue before permitting activation of the power and control system. In at least one embodiment, housing 12 is configured to at least partially prevent harmful matter from entering the drug pump. For example, the housing may be configured to restrict the passage of fluids into the drug pump. This may allow the device to be worn in the shower, while swimming, or during other activities. Use of an electrically based on-body sensor may eliminate potential points of entry into the drug pump for such fluids. These concepts are not mutually exclusive and one or more combinations may be utilized within the breadth of the present invention to prevent, for example, premature activation of the drug pump. In a preferred embodiment, the drug pump 10 utilizes one or more electrically based on-body sensors. Additional integrated safety mechanisms are described herein with reference to other components of the novel drug pumps.

Power and Control System:

The power and control system may include a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 100. In one embodiment, the power and control system interfaces either directly or indirectly with an on-body sensor 24 to identify when the device is in contact with the target and/or the activation mechanism 14 to identify when the device has been activated. The power and control system may also interface with the status indicator of the pump housing 12, which may be a transmissive or translucent material which permits light transfer, to provide visual feedback to the user. The power and control system interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the target, the power and control system will power the drive mechanism 100 to begin delivery of the drug treatment through the fluid pathway connection 300 and sterile fluid conduit (not shown).

Additionally, the power and control system may be configured to identify removal of the drug pump from its packaging. The power and control system may be mechanically, electronically, or electro-mechanically connected to the packaging such that removal of the drug pump from the packaging may activate or power-on the power and control system for use, or simply enable the power and control system to be powered-on by the user. In such an embodiment, without removal of the drug pump from the packaging the drug pump cannot be activated. This provides an additional safety mechanism of the drug pump and for the user. In at least one embodiment, the drug pump or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug pump or the power and control system may be mechanically connected to the packaging, such as by a pin and slot relationship which activates the system when the pin is removed (i.e., once the drug pump is removed from the packaging).

In a preferred embodiment of the present invention, once the power and control system has been activated, the drive mechanism is initiated to perform one or more of the steps of actuating the insertion mechanism 200 and the fluid pathway connection 300, while also permitting the drug fluid to be forced from the drug container. During the drug delivery process, the power and control system is configured to provide a dispensing status signal via the status indicator. After the drug has been administered into the target and after the end of any additional dwell time, to ensure that substantially the entire dose has been delivered to the target, the power and control system may provide an okay-to-remove status signal via the status indicator. This may be independently verified by the user by viewing the drive mechanism and drug dose delivery through the window 18 of the pump housing 12. Additionally, the power and control system may be configured to provide one or more alert signals via the status indicator, such as for example alerts indicative of fault or operation failure situations.

The power and control system may additionally be configured to accept various inputs from the user to dynamically control the drive mechanisms 100 to meet a desired drug delivery rate or profile. For example, the power and control system may receive inputs, such as from partial or full activation, depression, and/or release of the activation mechanism, to set, initiate, stop, or otherwise adjust the control of the drive mechanism 100 via the power and control system to meet the desired drug delivery rate or profile. Similarly, the power and control system may be configured to do one or more of the following: receive such inputs to adjust the drug dose volume; to prime the drive mechanism, fluid pathway connection, and fluid conduit; and/or to start, stop, or pause operation of the drive mechanism 100. Such inputs may be received by the user directly acting on the drug pump 10, such as by use of the activation mechanism 14 or a different control interface, or the power and control system may be configured to receive such inputs from a remote control device. Additionally or alternatively, such inputs may be pre-programmed.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Additionally, the power and control system may be configured to maintain regulation of the system's power source while providing momentary power to an actuator. During operation of the drug pump, as will be described further herein, momentary power is needed to move an actuator clockwise and counterclockwise between mechanical limits. This motion controls the motion of the drive system and, hence, the rate of delivery of the medicament. Directly supplying power to the actuator may lead to a large voltage drop which could interrupt the power source to other components of the drug pump. To avoid this, the power and control system may be configured to decouple the power source from the actuator when power is supplied to the actuator. To this end, the power and control system may include a switching device, such as a field-effect transistor; a charge-slowing device, such as a resistor; and a storage device, such as a capacitor. The three devices are serially connected between the power source and ground. The output is obtained from the capacitor and is connected to the actuator via a control device, such as an H-bridge. During operation the system operates in the following manner: First, the switching device is set to a fully closed configuration, connecting the power source, to the storage device and allowing the storage device to be charged by the power source in a length of time defined by, for example, the RC time constant. Second, the switch is opened, thereby disconnecting the power source from the storage device with the storage device remaining fully charged. Third, the charged storage device is applied to the control device. Fourth, the control device applies the stored power to the actuator and controls the actuator direction (clockwise or counterclockwise). In this way, the power source is not connected to the actuator when the actuator is powered, ensuring that the power source does not experience a voltage drop. This process repeats as needed to provide continued actuator clockwise and counterclockwise inputs to the pump drive mechanism without collapsing the system power source.

Insertion Mechanism:

A number of insertion mechanisms may be utilized within the drug pumps of the present invention. The pump-type delivery devices of the present invention may be connected in fluid flow communication to a target, for example, through any suitable hollow tubing. A hollow needle or a solid bore needle may be used to pierce the target and place a hollow cannula at the appropriate delivery position, with the needle being at least partially removed or retracted prior to drug delivery to the target. As stated above, the fluid can be introduced into the body through any number of means, including but not limited to: an automatically inserted needle, cannula, micro-needle array, or infusion set tubing. A number of mechanisms may also be employed to activate the needle insertion into the target. For example, a biasing member such as a spring may be employed to provide sufficient force to cause the needle and cannula to pierce the target. The same spring, an additional spring, or another similar mechanism may be utilized to retract the needle from the target. In one embodiment, the insertion mechanism may generally be as described in International Patent Application No. PCT/US2012/53174, which is included by reference herein in its entirety for all purposes. Such a configuration may be utilized for insertion of the drug delivery pathway into, or below, the target in a manner that minimizes pain. Other known methods for insertion of a fluid pathway may be utilized and are contemplated within the bounds of the present invention, including a rigid needle insertion mechanism and/or a rotational needle insertion mechanism as developed by the assignee of the present invention.

In at least one embodiment, the insertion mechanism 200 includes an insertion mechanism housing that may have a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the target. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to a sterile fluid conduit to permit fluid flow through the manifold, cannula, and into the target during drug delivery.

As used herein, "needle" is intended to refer to a variety of needles including but not limited to conventional hollow needles, such as a rigid hollow steel needles, and solid core needles more commonly referred to as a "trocars." In some embodiments, the needle is a 27 gauge solid core trocar and in other embodiments, the needle may be any size needle suitable to insert the cannula for the type of drug and drug administration (e.g., subcutaneous, intramuscular, intradermal, etc.) intended. In one or more embodiments, the insertion mechanism may generally be as described in International Patent Application No. PCT/US2012/53174 published as WO 2013/033421 A2, International Patent Application No. PCT/US2012/053241 published as WO 2013/033467 A2 or International Patent Application No. PCT/US2015/052815, which are included by reference herein in their entirety for all purposes.

The base includes a base opening through which the needle and cannula may pass-through during operation of the insertion mechanism. Sterility of the cannula and needle are maintained by their initial positioning within the sterile portions of the insertion mechanism. The base opening of base may be closed from non-sterile environments as well, such as by for example a sealing membrane.

According to at least one embodiment of the present invention, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the target. At the end of the insertion stage or at the end of drug delivery (as triggered by the drive mechanism), the retraction biasing member is permitted to expand in the proximal direction from its initial energized state. This axial expansion in the proximal direction of the retraction biasing member retracts the needle. If an inserter needle/trocar and cannula configuration is utilized, retraction of the needle may occur while maintaining the cannula in fluid communication with the target. Accordingly, the insertion mechanism may be used to insert a needle and cannula into the target and, subsequently, retract the needle while retaining the cannula in position for drug delivery to the target.

Figure 6A:
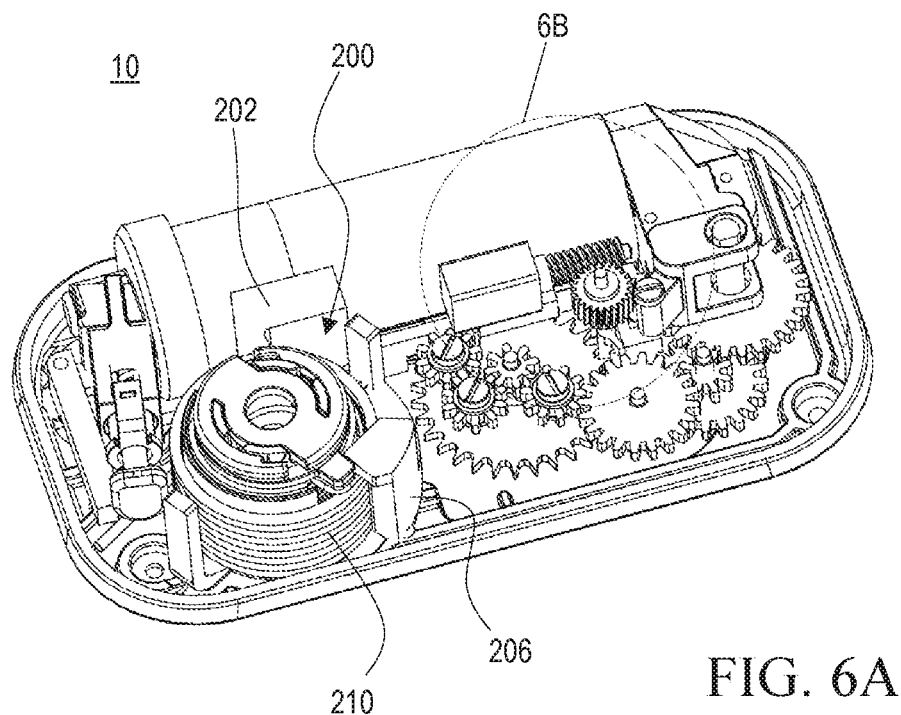
FIG. 6A is an isometric view of a drug delivery pump in which the insertion mechanism includes a rotational biasing member.

In one or more embodiments, the insertion mechanism may generally be as described in International Patent Application No. PCT/US2016/017534 filed Feb. 10, 2016, which is included by reference herein in its entirety for all purposes. In at least one embodiment, as shown in FIG. 6A, the insertion mechanism includes a rotationally biased member 210 which is initially held in an energized state. In a preferred embodiment, the rotationally biased member is a torsional spring. The rotational biasing member may be prevented from de-energizing by interaction of gear surface 208 with gear 112 as shown in FIG. 2A or, alternatively, by contact of a component of the insertion mechanism with a rotation prevention feature of the drug pump, as described further herein. Upon activation of the device, or another input, the rotationally biased member 210 is permitted to, at least partially, de-energize. This causes one or more components of the insertion mechanism to rotate and, in turn, cause, or allow, the insertion of the needle into the target. Further, a cannula may be inserted into the target as described above. At a later time, such as when the control arm or another component of the device recognizes a slack in the tether, the rotationally biased member may be allowed to further de-energize, causing additional rotation of one or more components of the insertion mechanism. This rotation may cause, or allow, the needle to be retracted from the target. The needle may be fully retracted in a single step or there may be multiple steps of retraction.

Figure 13A:
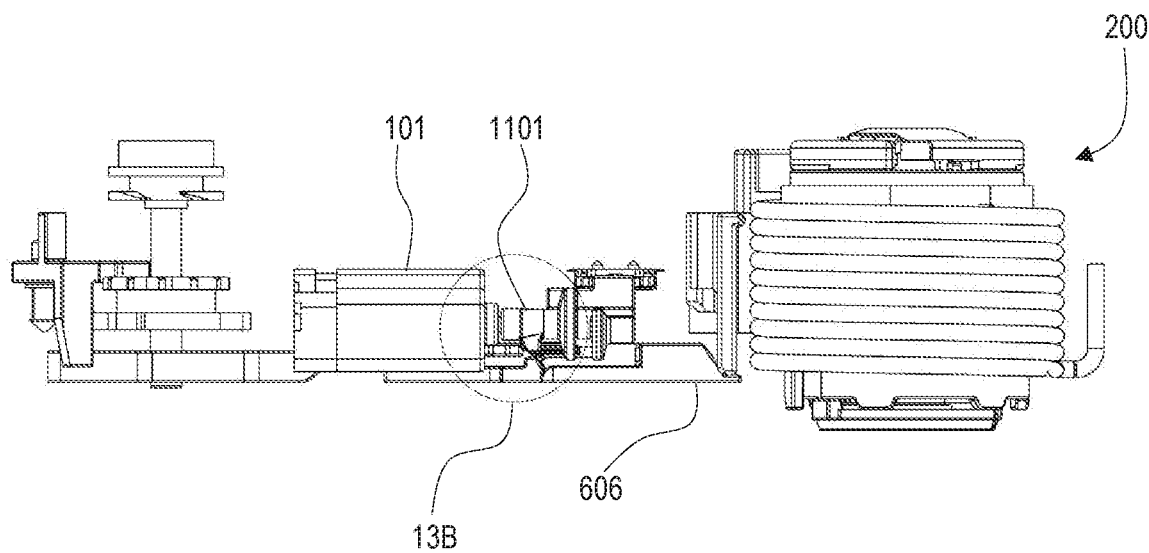
FIG. 13A is a side elevation view of an enabling mechanism according to at least one embodiment of the present invention.
Figure 13B:
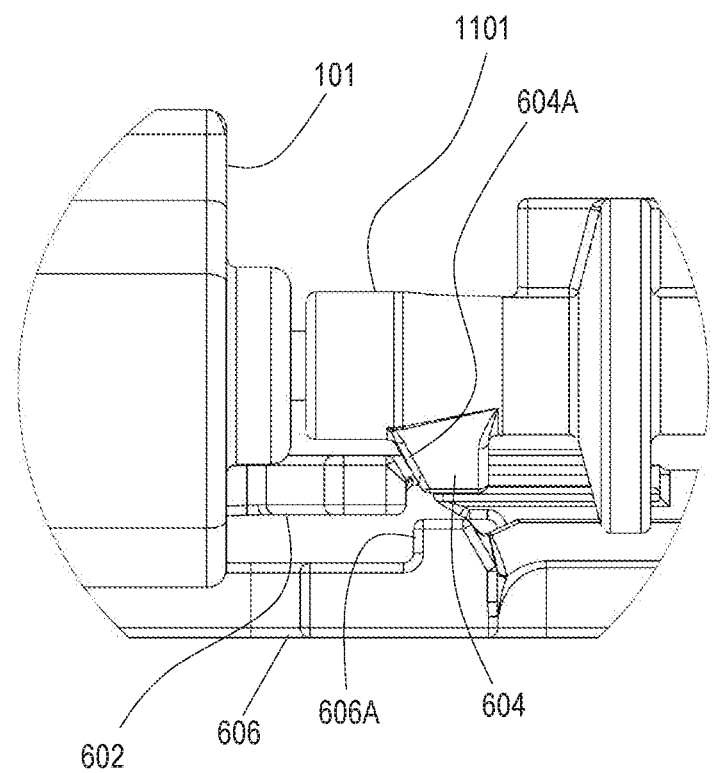
FIG. 13B is an enlarged, fragmentary side elevation view of the enabling mechanism of FIG. 13A.
Figure 14:
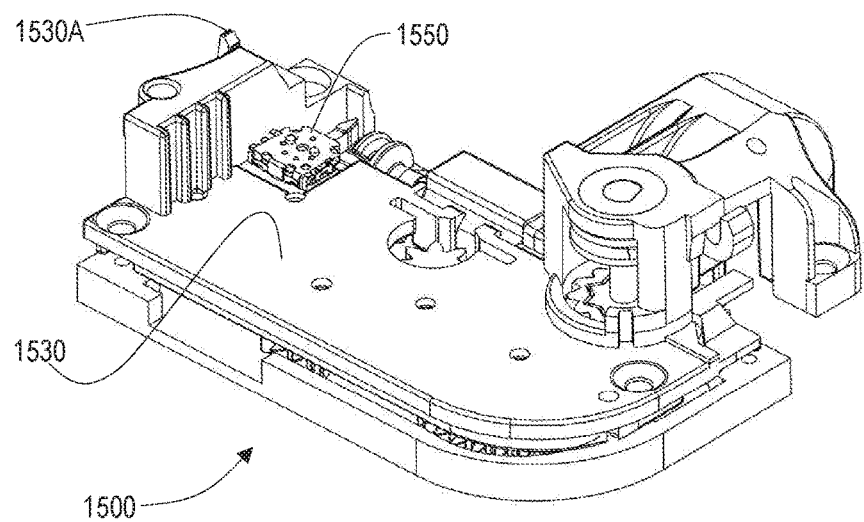
FIG. 14 is an isometric view of a regulating mechanism according to at least one embodiment of the present invention.

In one embodiment, translation of the activation mechanism may be a part of, or operate, a NIM activation mechanism. The NIM activation mechanism may include an enabling mechanism as shown in FIGS. 13A-13B. In this embodiment, translation of the activation mechanism 14 may be directly or indirectly coupled to a slide 602. In a first configuration, the enabling mechanism is configured such that translation of the activation mechanism and slide does not cause activation of the needle insertion mechanism 200 or sterile fluid pathway connection 300.

FIGS. 13A-13B illustrate the enabling mechanism configured such that translation of the activation mechanism 14 (See FIG. 1A) and slide 602 causes activation of the needle insertion mechanism 200. Transformation of the enabling mechanism from the first configuration to the second configuration may be initiated by, for example, triggering of an on-body sensor, or by the elapsing of a predetermined amount of time after power-on of the device. The transformation of the enabling mechanism from the first to the second configuration may be performed by rotation of the actuator 101 which may cause a selector member 604 to become aligned with an aspect of the slide 602. The selector member 604 may include a ramped surface 604A which is configured to contact a portion of the slide 602 upon translation of the activation mechanism 14 and slide 602. The selector member 604 may be mounted to or be an integral portion of the gear interface such as key 1101. Contact of the slide 602 with the selector member 604 may cause the slide 602 to be displaced such that a portion of the slide is aligned with a portion of a throw arm or control arm 606, such as protrusion 606A. In this configuration, translation of the activation mechanism 14 causes translation of the throw arm 606. Translation of the throw arm 606 causes activation of the needle insertion mechanism 200 to insert the fluid path into the target. During manufacturing, transportation, and storage, the enabling mechanism is in the first configuration in which depression of the activation mechanism 14 does not activate the needle insertion mechanism 200. In this way, the needle insertion mechanism is prevented from activating prematurely. Contact of the slide 602 with the selector member 604 may cause substantially rigid body displacement of the slide or, alternatively, the contact may cause a deformation of the slide. For example, the slide may include a deformable (i.e., less rigid) portion which may be displaced by the contact.

One example of a NIM activation mechanism is shown in FIGS. 7A-12B. For clarity, a number of components of the drug delivery device are hidden in these figures. The NIM activation mechanism includes: a slide 602, a throw arm 606, a NIM interlock 608, and a NIM retainer 610. Initially, as shown in FIGS. 7A-8B, the NIM retainer 610 is positioned such that the NIM retainer 610 is in contact with a protrusion 204 of the NIM 200 such that the protrusion 204 is prevented from rotating about axis R (see FIG. 9B), thereby preventing activation of the NIM 200. In the embodiment shown, the NIM retainer 610 is configured for rotational movement about axis B (see FIG. 11B). The NIM retainer 610 may, for example, be mounted to the housing 12 or to the top plate 1530 at the bore 610A. For example, a pin or shaft may be disposed in bore 610A around which the NIM retainer 610 may rotate. The pin or shaft may an integral portion of the housing 12 or top plate 1530 or, alternatively, may be a separate component. The NIM retainer 610 is prevented from rotating by contact between an arm 610B of the NIM retainer 610 with the NIM interlock 608. The NIM interlock 608 is disposed for translational motion (in the direction of the hatched arrow of FIG. 7B) and is initially held in position by a flex arm 1530A which may be a portion of the top plate 1530. The NIM interlock 608 is initially in a first position in which it is in contact with or adjacent to a lower surface 606B of the throw arm 606.

Figure 7A:
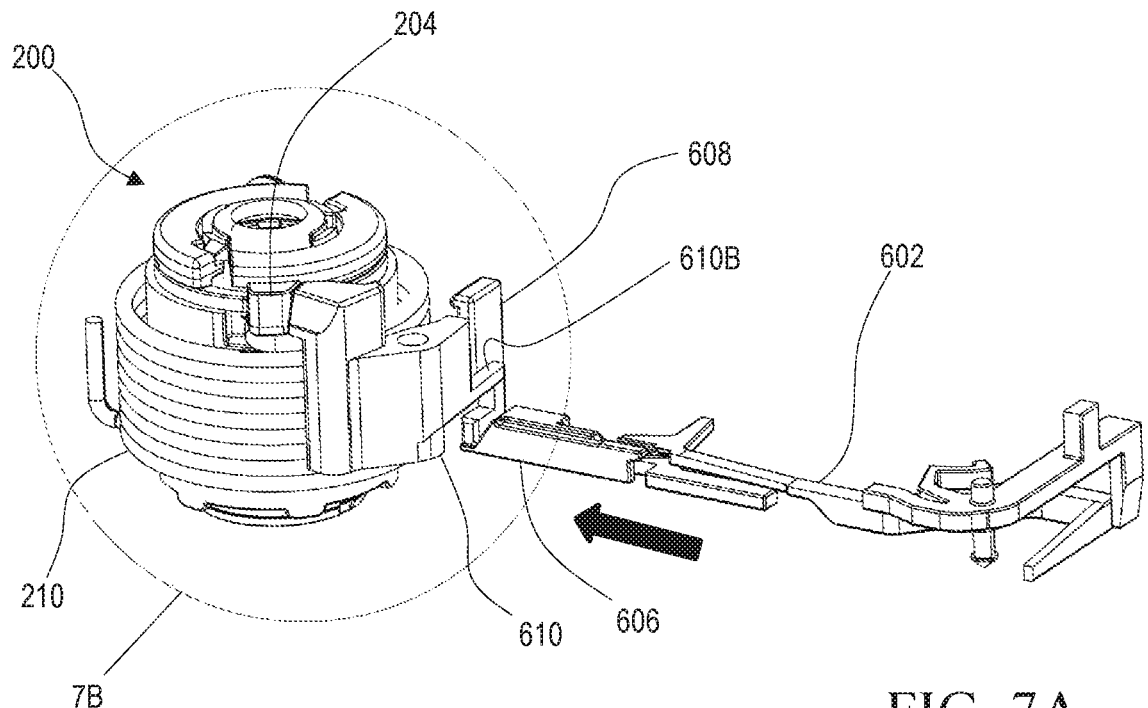
FIG. 7A is an isometric view of an insertion mechanism in an initial configuration.
Figure 7B:
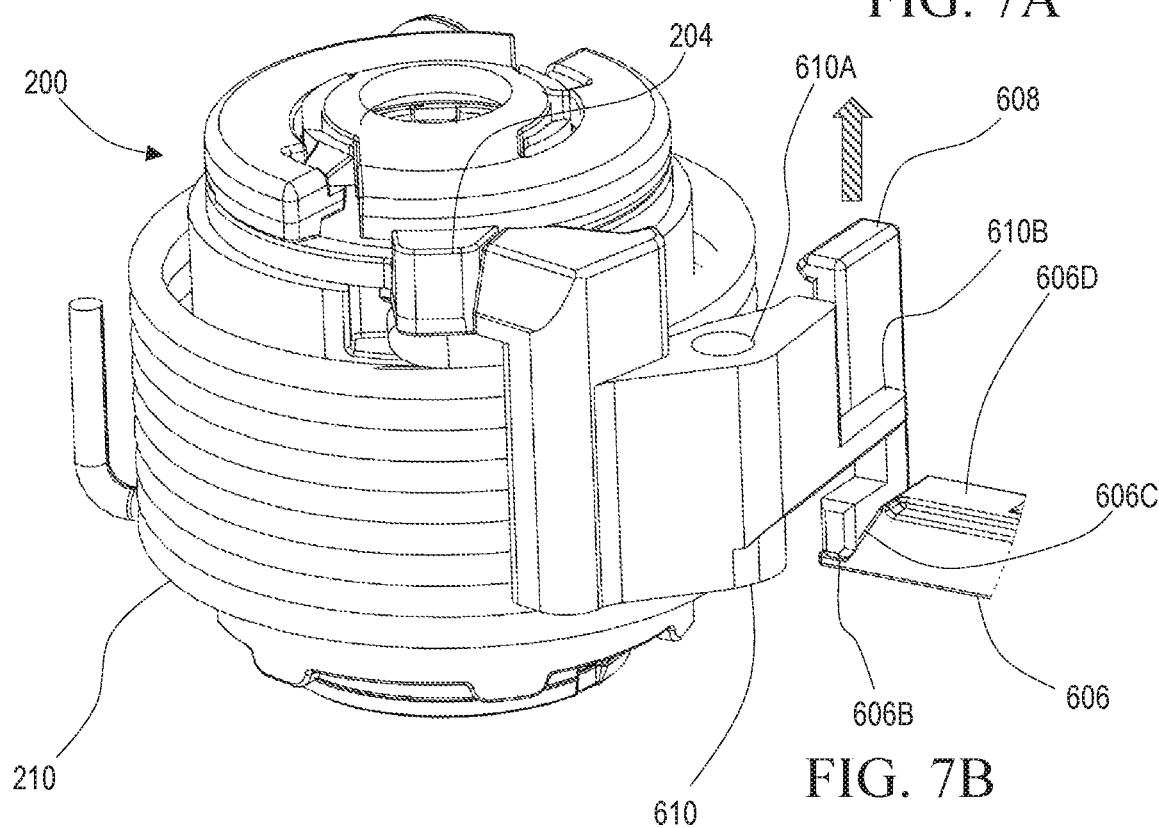
FIG. 7B is an enlarged, fragmentary isometric view of the insertion mechanism of FIG. 7A.
Figure 8A:
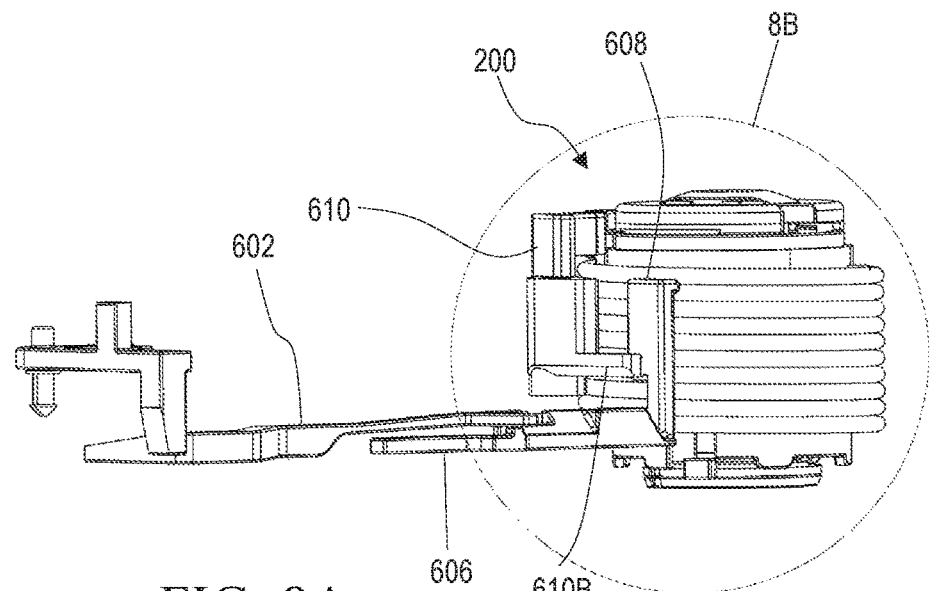
FIG. 8A is a side elevation view of the insertion mechanism of FIG. 7A in an initial configuration.
Figure 8B:
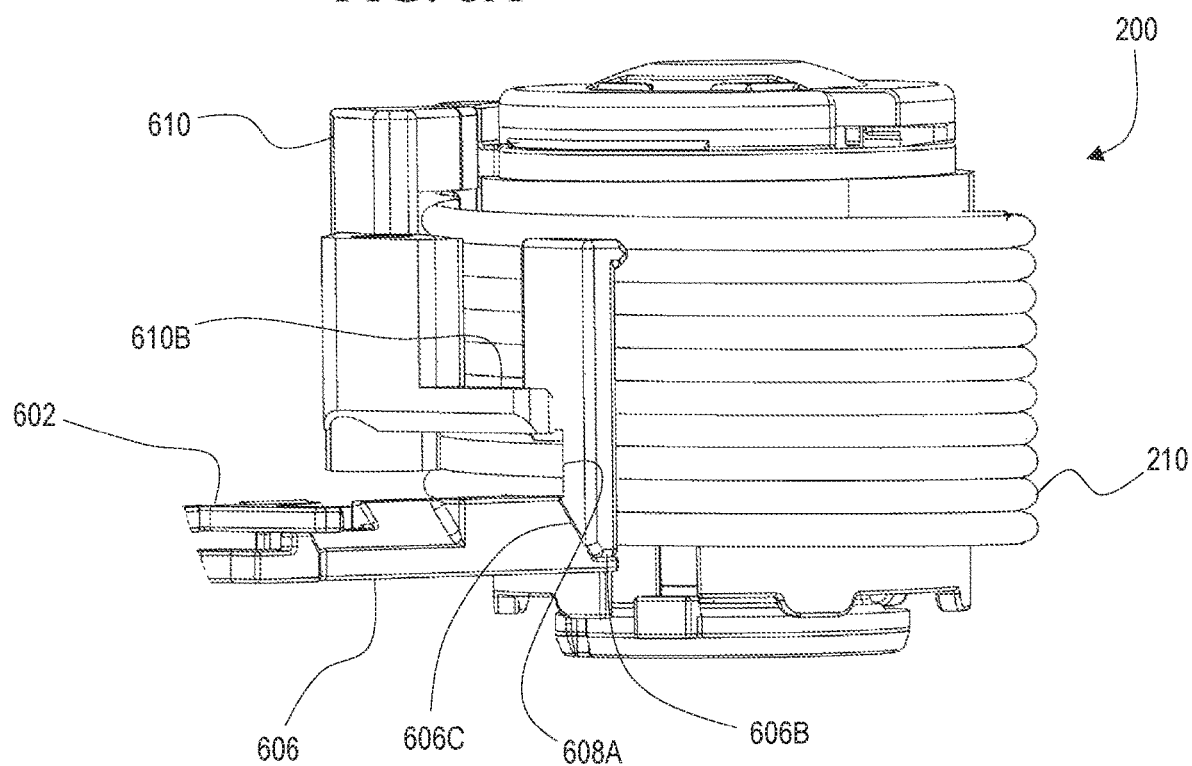
FIG. 8B is an enlarged, fragmentary, side elevation view of the insertion mechanism of FIG. 8A.
Figure 9A:
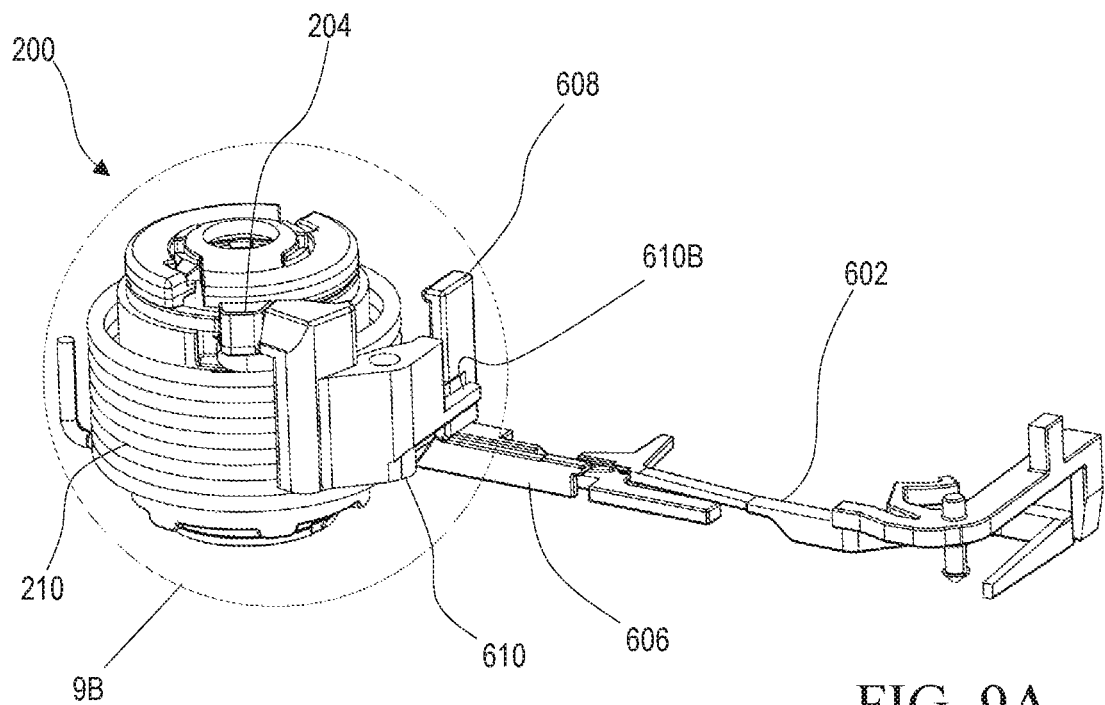
FIG. 9A is an isometric view of the insertion mechanism of FIG. 7A in an intermediate configuration.
Figure 9B:
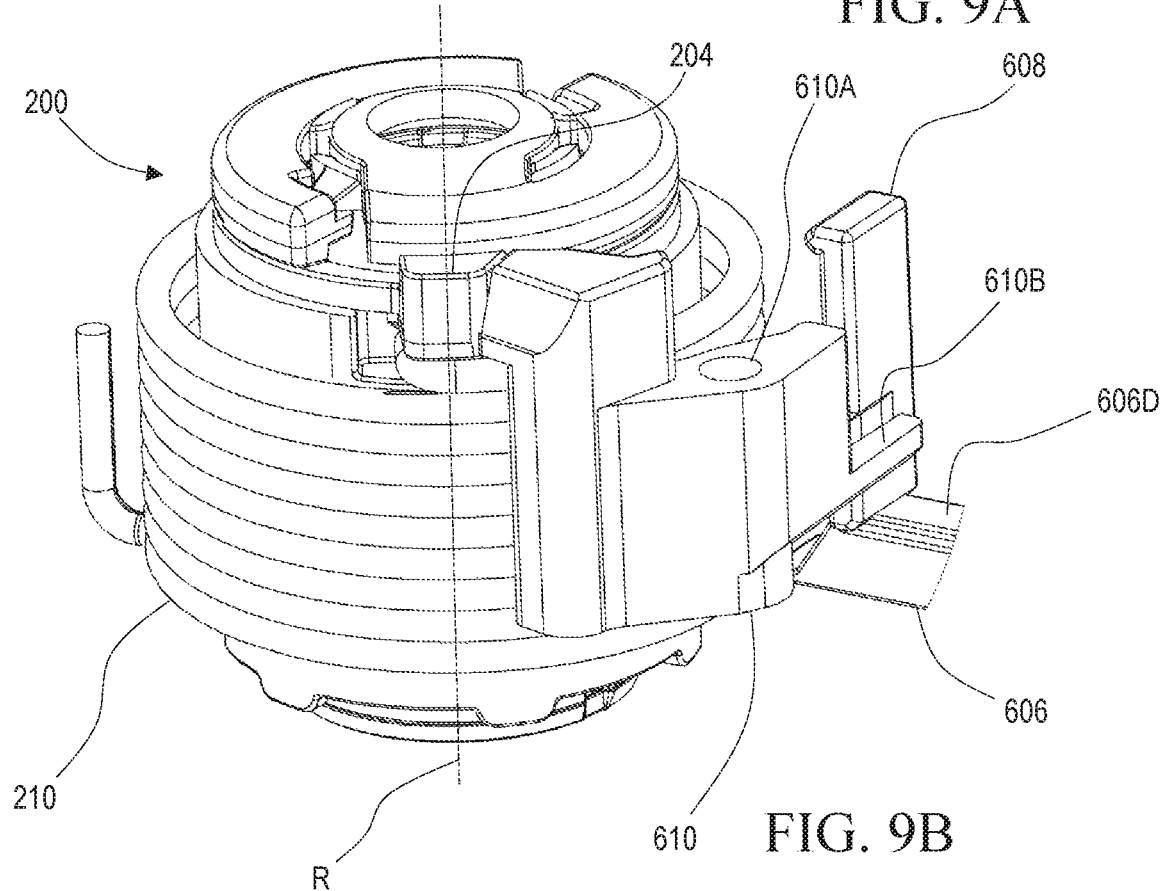
FIG. 9B is an enlarged, fragmentary isometric view of the insertion mechanism of FIG. 9A.
Figure 10A:
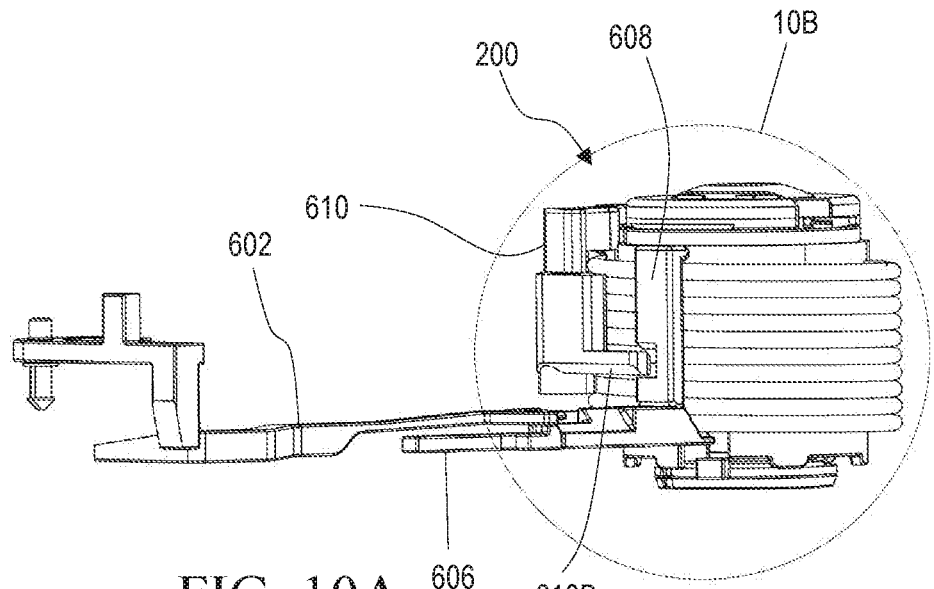
FIG. 10A is a side elevation view of the insertion mechanism of FIG. 9A in an intermediate configuration.
Figure 10B:
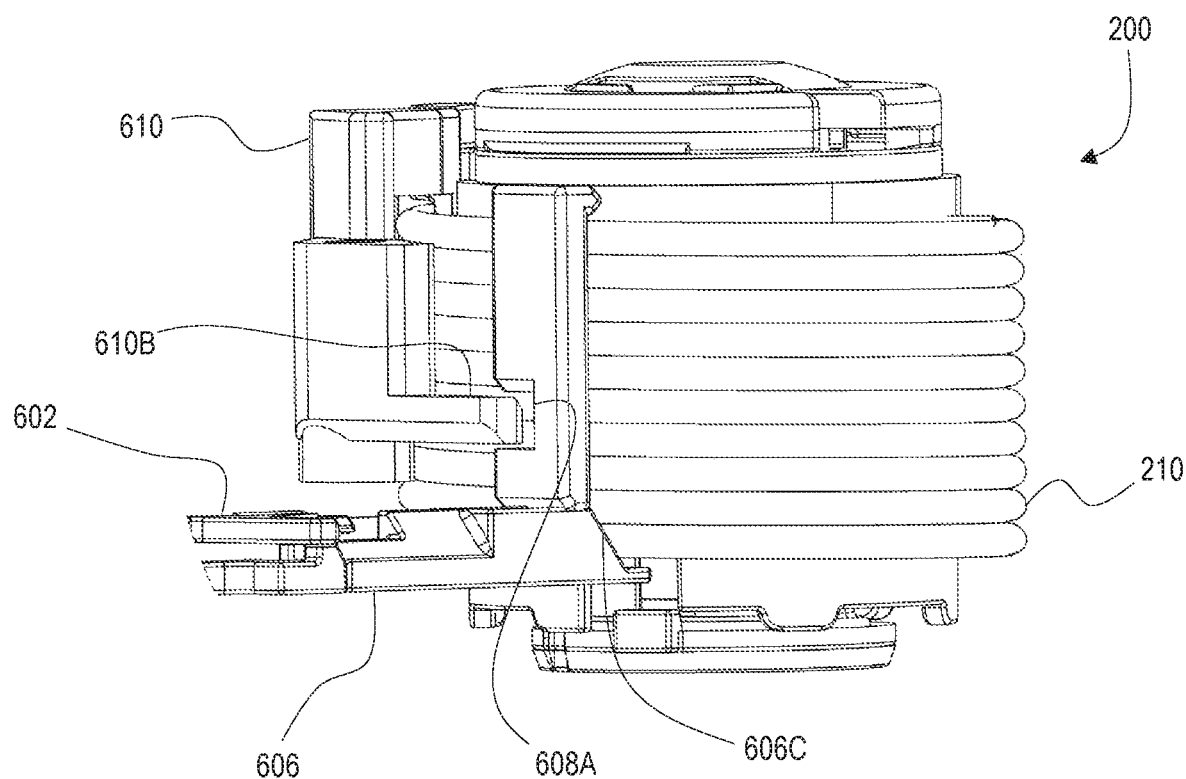
FIG. 10B is an enlarged, fragmentary, side elevation view of the insertion mechanism of FIG. 10A.
Figure 11A:
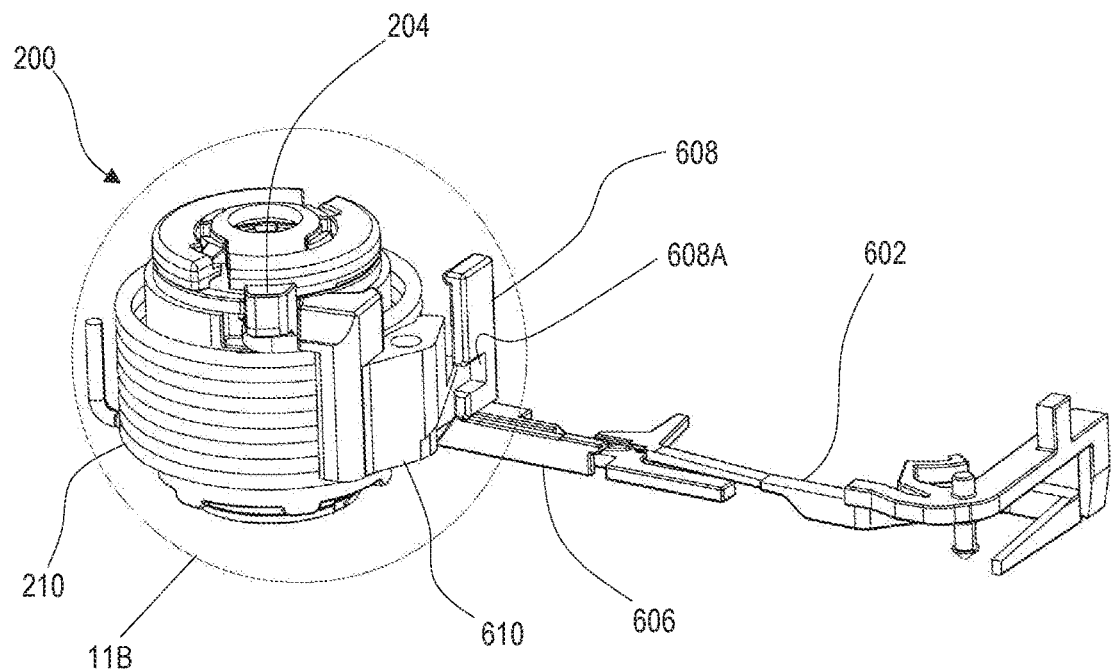
FIG. 11A is an isometric view of the insertion mechanism of FIG. 7A in an released configuration.
Figure 11B:
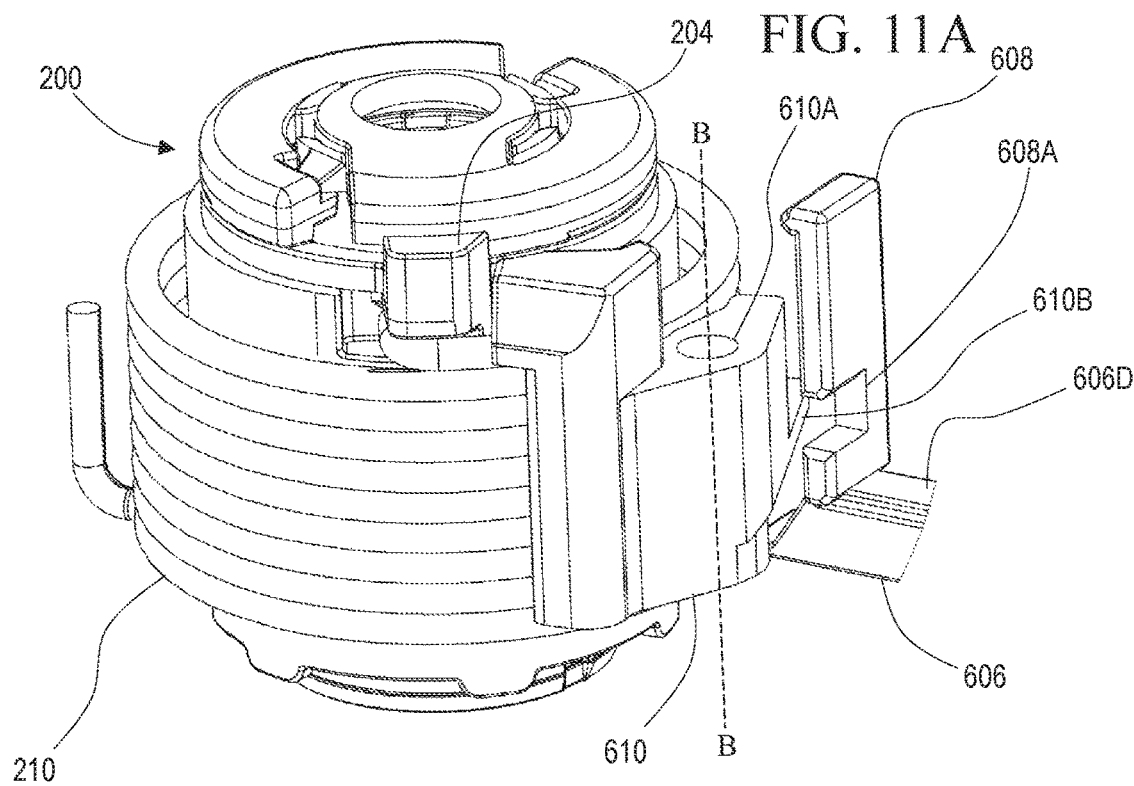
FIG. 11B is an enlarged, fragmentary isometric view of the insertion mechanism of FIG. 11A.
Figure 12A:
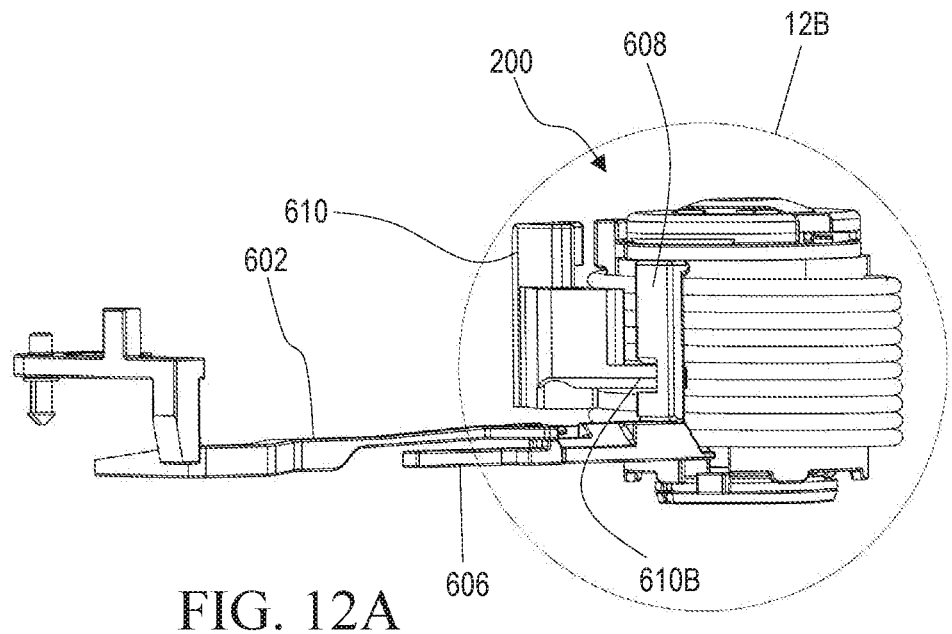
FIG. 12A is a side elevation view of the insertion mechanism of FIG. 11A in an released configuration.
Figure 12B:
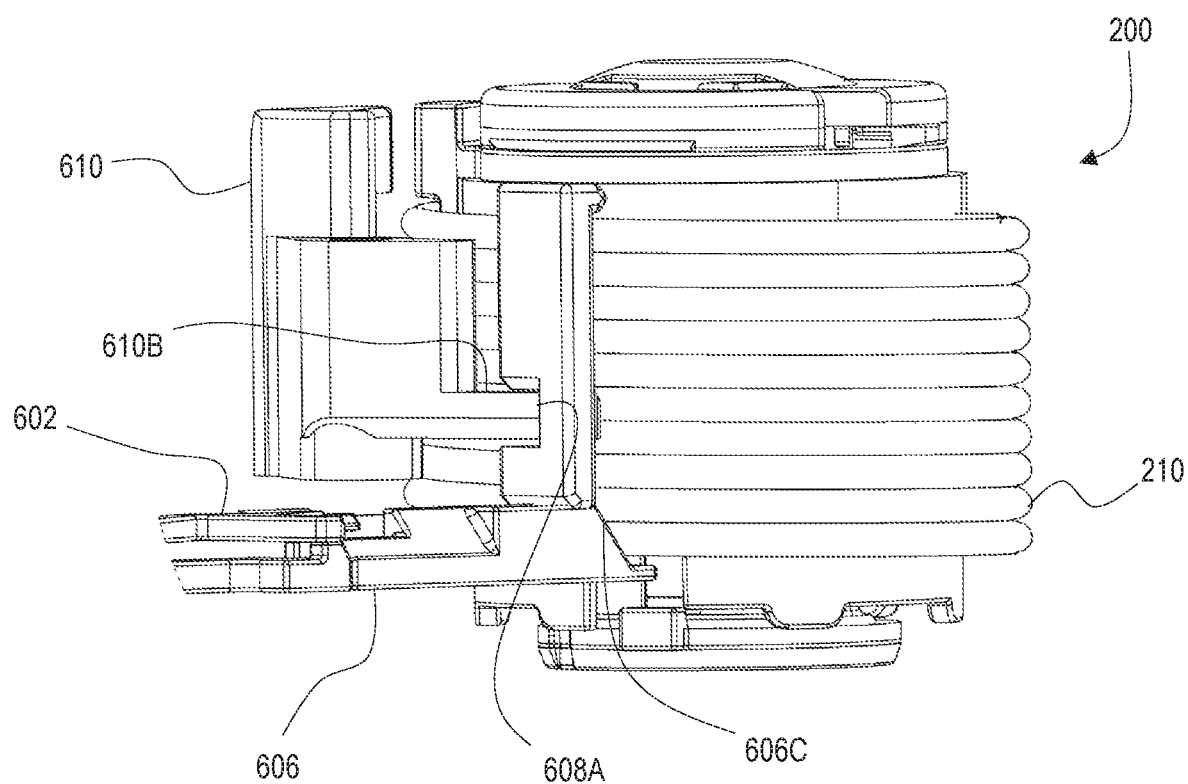
FIG. 12B is an enlarged, fragmentary, side elevation view of the insertion mechanism of FIG. 12A.

With the selector member 604 in the second configuration (shown in FIGS. 13A-13B) depression of the activation mechanism 14 causes translation of the throw arm 606 as described above (in the direction of the solid arrow in FIG. 7A). The ramped surface 606C of the throw arm 606 contacts the NIM interlock 608 and causes the NIM interlock 608 to translate in a direction substantially orthogonal to the direction of translation of the throw arm 606. FIGS. 9A-10B show the position of the throw arm 606 and NIM interlock 608 after translation of the throw arm. As shown, in this configuration, the NIM interlock 608 is positioned adjacent to or in contact with an upper surface 606D of the throw arm 606. The window 608A of the NIM interlock 608 is aligned with the arm 610B of the NIM retainer 610. Hence, as shown in FIGS. 11A-12B, the NIM retainer 610 is able to rotate about axis B. The contact surfaces of protrusion 204 and retainer 610 may be configured such that the protrusion 204 applies a rotational force to NIM retainer 610, thereby causing rotation of NIM retainer 610 about axis B. Alternatively, or additionally, the NIM retainer 610 may be biased to rotate by a biasing member. The biasing member may be, for example, a torsion spring. Rotation of the NIM retainer 610 causes the NIM retainer 610 to disengage the protrusion 204 of the NIM 200. Hence, the NIM 200 is able to activate to insert a fluid path into a target.

In other embodiments, the NIM interlock 608 may directly engage a portion of the NIM 200, such as the protrusion 204, to initially prevent activation of the NIM 200. Translation of the NIM interlock 608 in the direction orthogonal to the translation of the throw arm 606 may cause the NIM interlock 608 to disengage the NIM 200 and allow the NIM 200 to activate. Also, while the slide 602 and the throw arm 606 are shown here as separate components, it is contemplated that these can be combined into a single, unified component. In such an embodiment, the selector member may initially be configured to prevent translation of the slide and/or throw arm.

In another embodiment, the throw arm 606 is engaged with a portion of the NIM whereby translation of the throw arm 606 allows activation of the NIM 200.

In addition to the advantages described above, the insertion mechanisms described herein may also be capable of terminating flow of medicament to the target tissue by disconnecting the fluid path. This may be an important safety feature to protect the target. For example, some medicaments, such as insulin, can be dangerous, and potentially even deadly, when administered in too large a quantity and/or at too rapid of a rate. By providing such automatic safety stop mechanisms, so-called "run-away" delivery of medicament may be prevented, thereby ensuring the safety of the target. While the methods and associated structures for terminating flow may be discussed with regard to one or more specific insertion mechanisms disclosed herein, it will be appreciated that the method and associated structures may be utilized or adapted for any of the insertion mechanisms disclosed herein or within the spirit and scope of this disclosure.

An interruption in delivery of medicament to the target tissue may be triggered, for example, by an error in delivery of the medicament or by an input from the user. For example, the user may realize that they have already taken their drug dose and wish to pause or terminate drug delivery from the device. Upon such user input to the device, the delivery of the drug can be stopped and/or the fluid passageway through the needle or cannula may be terminated by retraction of the needle to its fully retracted position.

Additionally or alternatively, the device may pause or terminate drug delivery if it receives an error alert during operation. For example, if the drive mechanism is not functioning correctly, the needle insertion mechanism may be triggered to retract fully and terminate drug delivery to the target tissue to prevent over-delivery of a medication to the target tissue. This capability of the needle insertion mechanism provides a valuable safety feature for drug delivery to a target.

In some embodiments, retraction is activated upon removal of the drug pump from the target tissue. In other embodiments, retraction is activated if it is determined that an error has occurred in the delivery of the substances to the target tissue. For example, an occlusion of the drug delivery pathway which prevents the flow of medicament may be detected by a sensing function of the drug delivery pump. Upon the sensing of the occlusion an electrical or mechanical input may be used to initiate retraction of the needle.

Fluid Pathway Connection:

A number of fluid pathway connections may be utilized within the embodiments of the present invention. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the target. In one such embodiment, the fluid pathway connection may be substantially similar to that described in International Patent Application No. PCT/US2012/054861, published as WO 2015027174 A4 or International Patent Application No. PCT/US2016/020486 filed Mar. 2, 2016, which are included by reference herein in its entirety for all purposes. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connection. Accordingly, the integrated sterile fluid pathway connection is connected (i.e., the fluid pathway is opened) by the combination pneumatic/hydraulic force of the air/gas and drug fluid within the drug chamber created by activation of a drive mechanism. Once the integrated sterile fluid pathway connection is connected or opened, drug fluid is permitted to flow from the drug container, through the integrated sterile fluid pathway connection, sterile fluid conduit, and insertion mechanism, and into the target for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connection is initiated by movement of the needle insertion mechanism, which itself is initiated by the drive mechanism. Additionally or alternatively, the sterile fluid pathway connection is initiated by movement directly of the drive mechanism. For example, the drive mechanism may include a rotational gear, such as the star gear described in detail herein, that acts concurrently or sequentially to control the rate of drug delivery, to actuate the needle insertion mechanism, and/or initiate the sterile fluid pathway connection. In one particular embodiment, shown in FIGS. 1A-1C, the drive mechanism performs all of these steps substantially concurrently. The drive mechanism rotates a gear that acts upon several other components. The gear acts on a gear assembly to control the rate of drug delivery, while also contacting a needle insertion mechanism to introduce a fluid pathway into the target. As the needle insertion mechanism is initiated, the sterile fluid connection is made to permit drug fluid flow from the drug container, through the fluid conduit, into the needle insertion mechanism, for delivery into the target as the gear and gear assembly of the drive mechanism control the rate of drug delivery.

Regardless of the fluid pathway connection utilized by the drug pump, the drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Drive Mechanism:

The drive mechanisms of the present invention may enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a target; and (iii) connecting a sterile fluid pathway to a drug container to permit fluid flow from the drug container to the needle insertion mechanism for delivery to the target. With reference to the embodiments shown in FIGS. 2A-2E and 3A-3D, drive mechanism 100 includes an actuator 101, a gear assembly 116 including a main gear 102, a drive housing 130, and a drug container 50 having a cap 52, a pierceable seal (not visible), a barrel 58, and a plunger seal 60. The main gear 102 may be, for example, a star gear disposed to contact multiple secondary gears or gear surfaces. A drug chamber 21, located within the barrel 58 between the pierceable seal and the plunger seal 60, may contain a drug fluid for delivery through the insertion mechanism and drug pump into the target. The seals described herein may be comprised of a number of materials but are, in a preferred embodiment, comprised of one or more elastomers or rubbers. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the target.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. Optionally, as will be described further hereinafter, the piston may include one or more safety mechanisms which may be configured to restrict the translation of the piston to restrict flow of medicament to the target. Such safety mechanisms can include a brake mechanism, a plunger seal piercing mechanism, and a plunger seal displacing mechanism, such as those described in detail herein. The fluid pathway connection may be connected through the pierceable seal prior to, concurrently with, or after activation of the drive mechanism to permit fluid flow from the drug container, through the fluid pathway connection, sterile fluid conduit, and insertion mechanism, and into the target for drug delivery. In at least one embodiment, the fluid flows through only a manifold or needle and a cannula of the insertion mechanism, thereby maintaining the sterility of the fluid pathway before and during drug delivery. Such components and their functions are described in further detail herein.

Referring now to the embodiment of the drive mechanism shown in FIGS. 2A-2E and 3A-3D, drive mechanism 100 includes an actuator 101, a gear assembly 116 including a main gear 102, a drive housing 130, and a drug container 50 having a cap 52, a pierceable seal (not visible), a barrel 58, and a plunger seal 60. The main gear 102 may be, for example, a star gear disposed to contact multiple secondary gears or gear surfaces. A drug chamber 21, located within the barrel 58 between the pierceable seal and the plunger seal 60, may contain a drug fluid for delivery through the insertion mechanism and drug pump into the target. Compressed within the drive housing 130, between the drug container 50 and the proximal end of the housing 130, are one or more drive biasing members 122 and a piston 110, wherein the drive biasing members 122 are configured to bear upon an interface surface 110C of the piston 110, as described further herein. Optionally, a cover sleeve (not shown) may be utilized between the drive biasing members 122 and the interface surface 110C of the piston 110 to, for example, promote more even distribution of force from the drive biasing member 122 to the piston 110, prevent buckling of the drive biasing members 122, and/or hide the biasing members 122 from user view. Interface surface 110C of piston 110 is caused to rest substantially adjacent to, or in contact with, a proximal end of seal 60. Although the embodiments shown in FIGS. 2A-2E and 3A-3D show a singular biasing member it is also contemplated that one or more biasing members disposed to act in parallel or in series may be used.

Figure 2E:
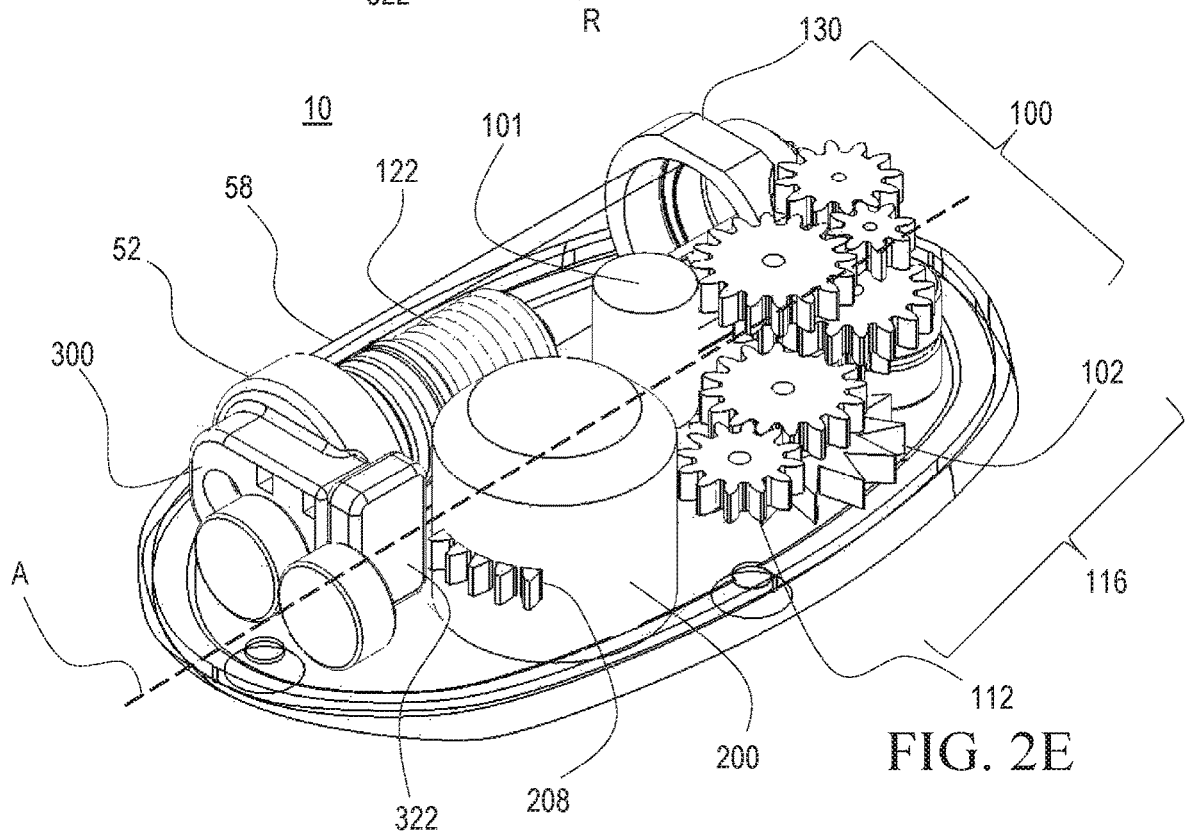
FIG. 2E is an isometric view of a drive mechanism, according to at least one embodiment of the present invention near or at completion of drug delivery.
Figure 3A:
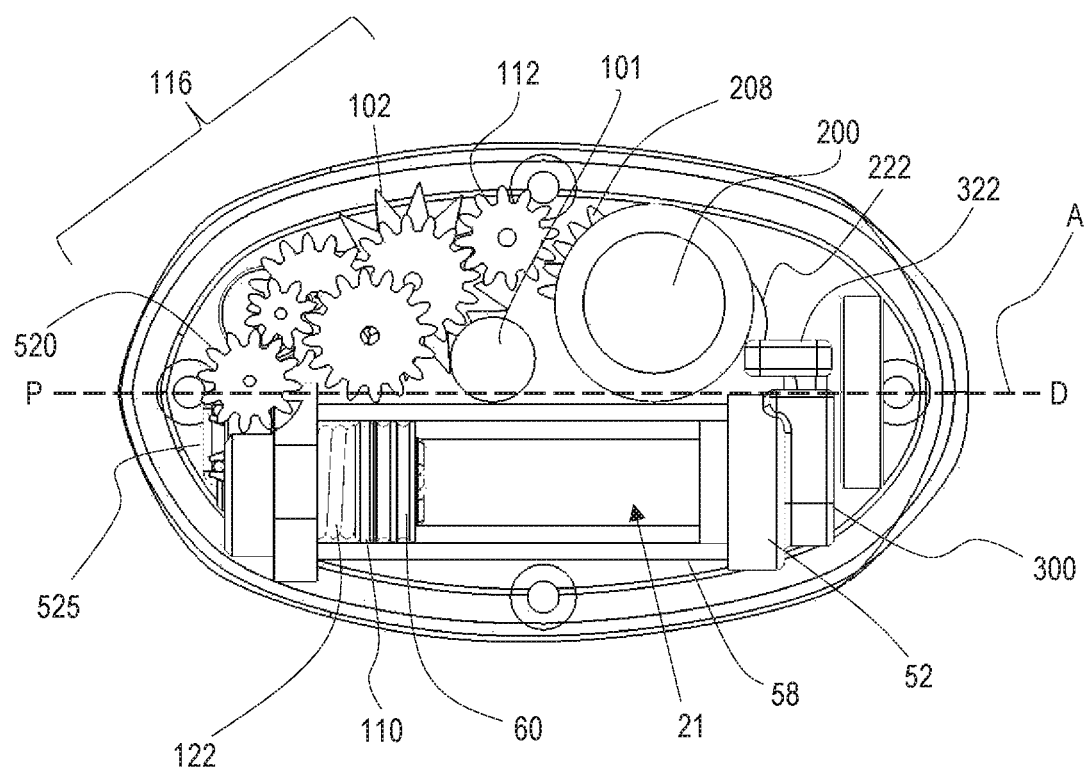
FIGS. 3A-3D are top views which correspond with the stages of operation shown in FIGS. 2A-2E, respectively.
Figure 3B:
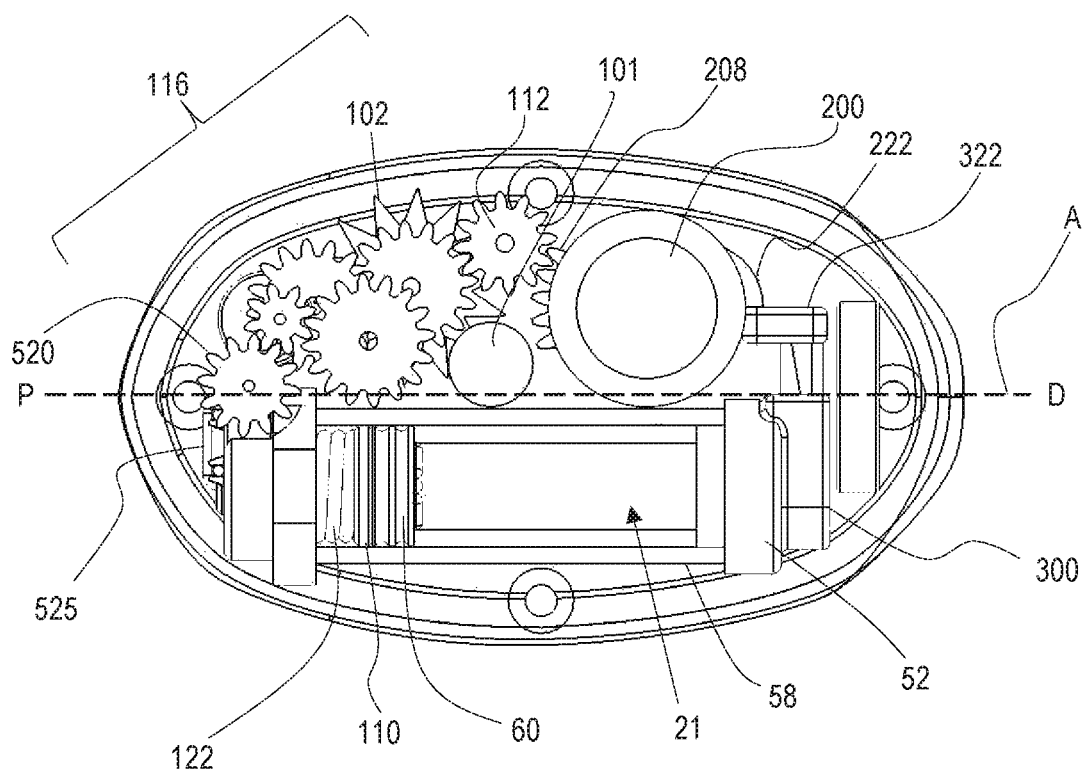
Figure 3C:
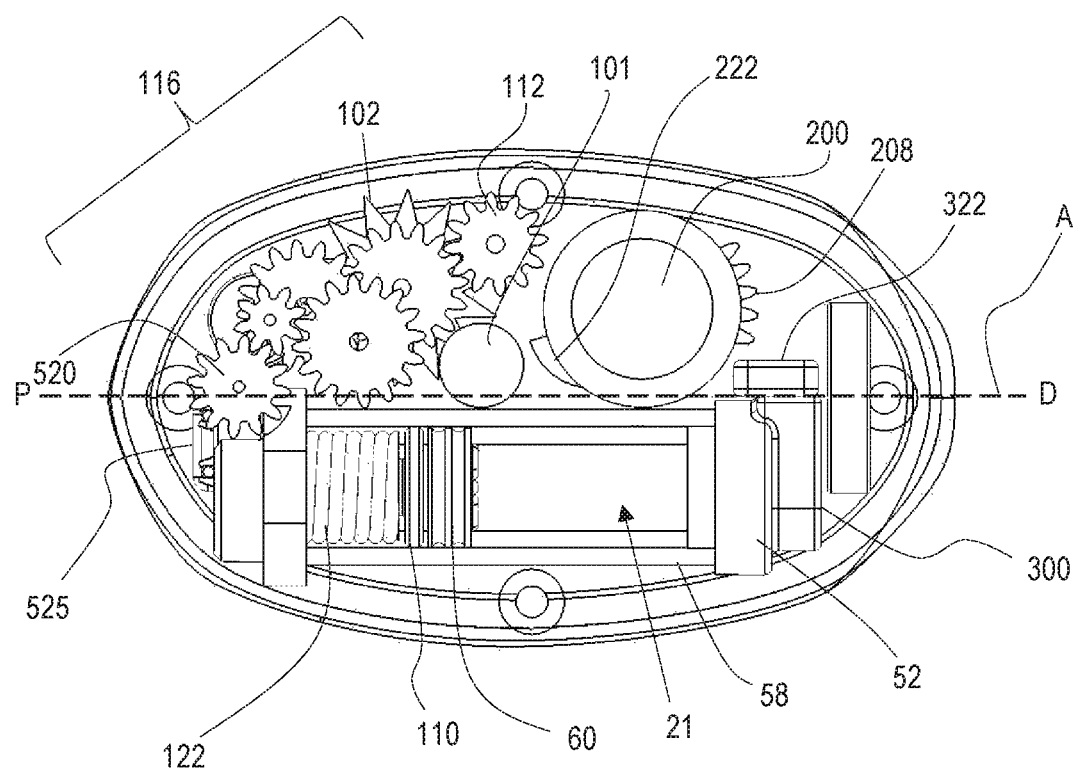
Figure 3D:
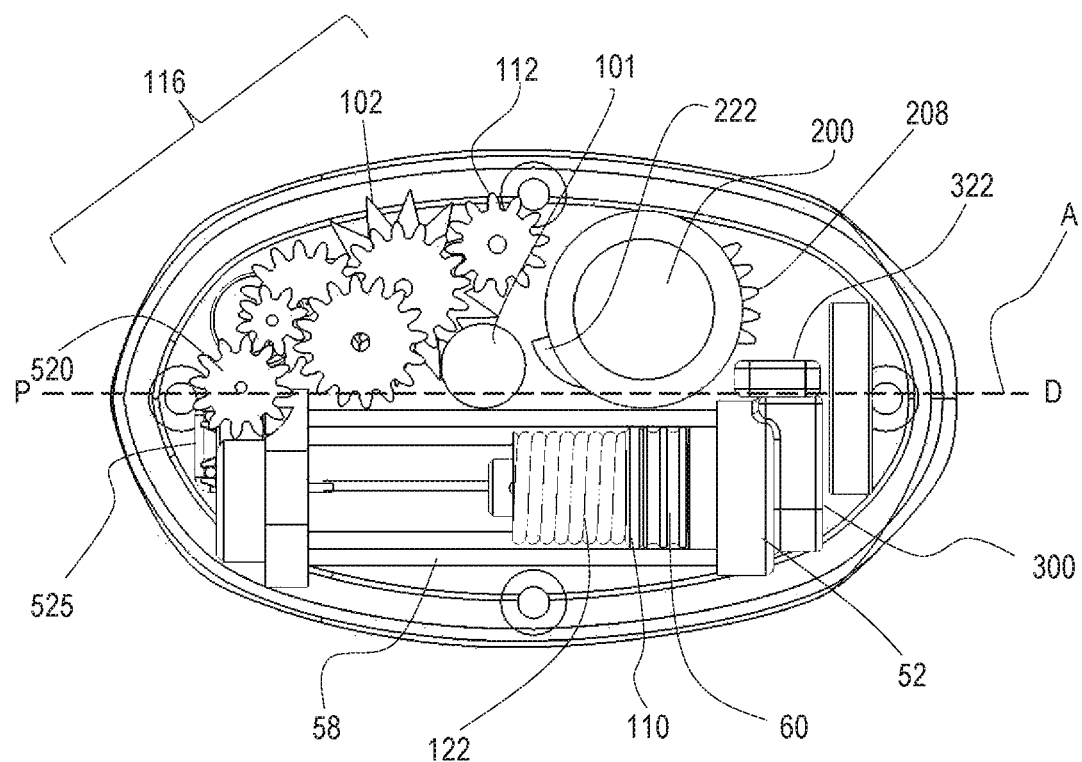

As best shown in FIG. 2E and FIG. 3D, the piston 110 may be comprised of one or more components and have an interface surface to contact the plunger seal. A tether, ribbon, string, or other retention strap (referred to herein as the "tether" 525; See FIG. 3D) may be connected at one end to the piston 110. For example, the tether 525 may be connected to the piston 110 by retention between the two components of the piston 110 when assembled. FIG. 3D shows the biasing member partially hidden to allow the connection of the tether to the piston to be viewed. The tether 525 is connected at another end to a winch assembly 520 of a delivery control or regulating mechanism 500. Winch assembly 520 includes winch gear 520A and winch drum 520B rotation of which is coupled, for example by a keyed relationship. Through the use of the winch assembly 520 connected to one end of the tether 525, and the tether 525 connected at another end to the piston 110, the regulating mechanism 500 functions to control, meter, provide resistance, or otherwise prevent free axial translation of the piston 110 and plunger seal 60 utilized to force a drug substance out of a drug container 50. Accordingly, the regulating mechanism 500 is a portion of the gear assembly 116 aspect of the drive mechanism, which together function to control the rate or profile of drug delivery to the target.

Figure 4:
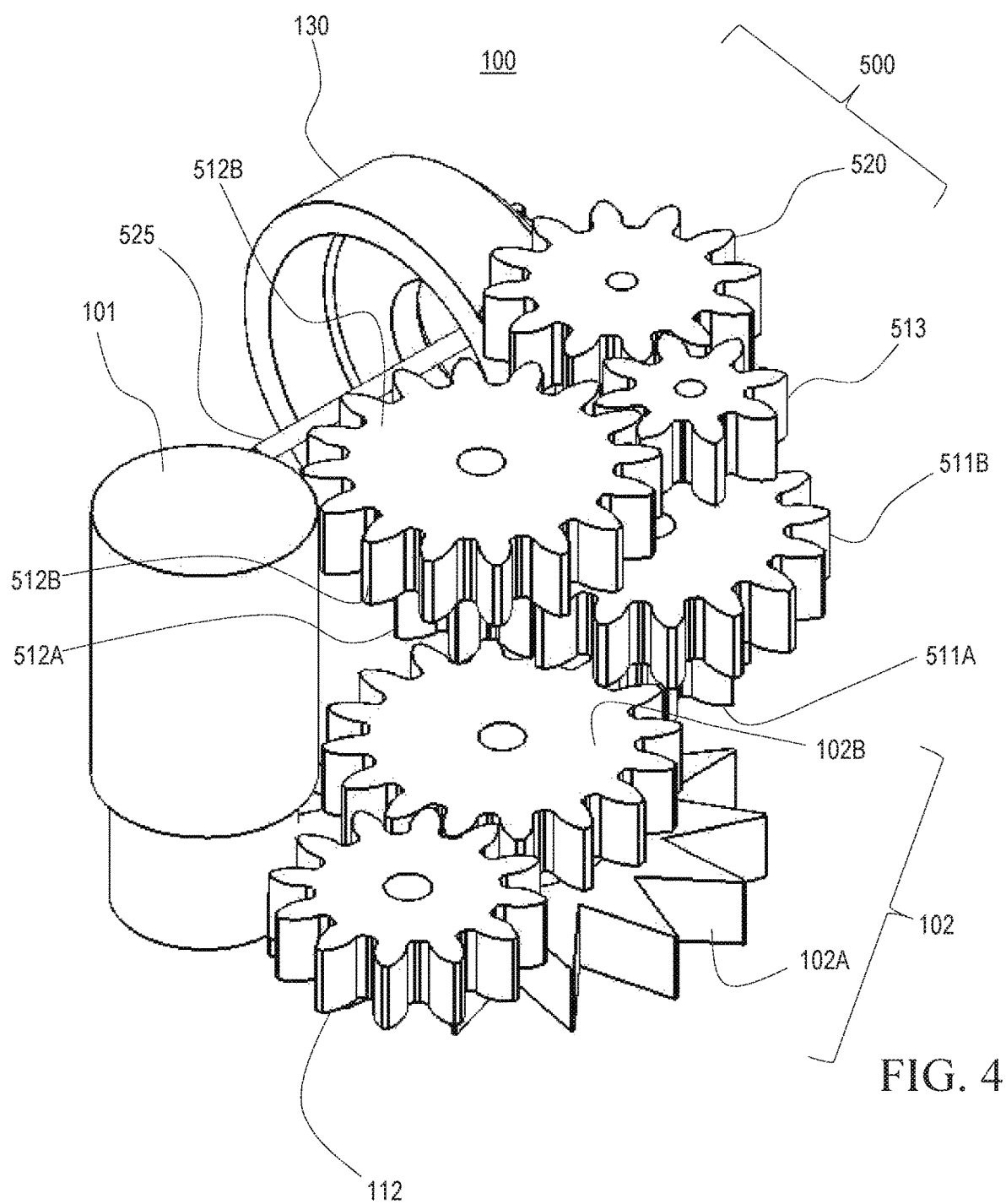
FIG. 4 is an isometric view of the drive mechanism, according to at least one embodiment of the present invention, in isolation from the drug delivery device.
Figure 5A:
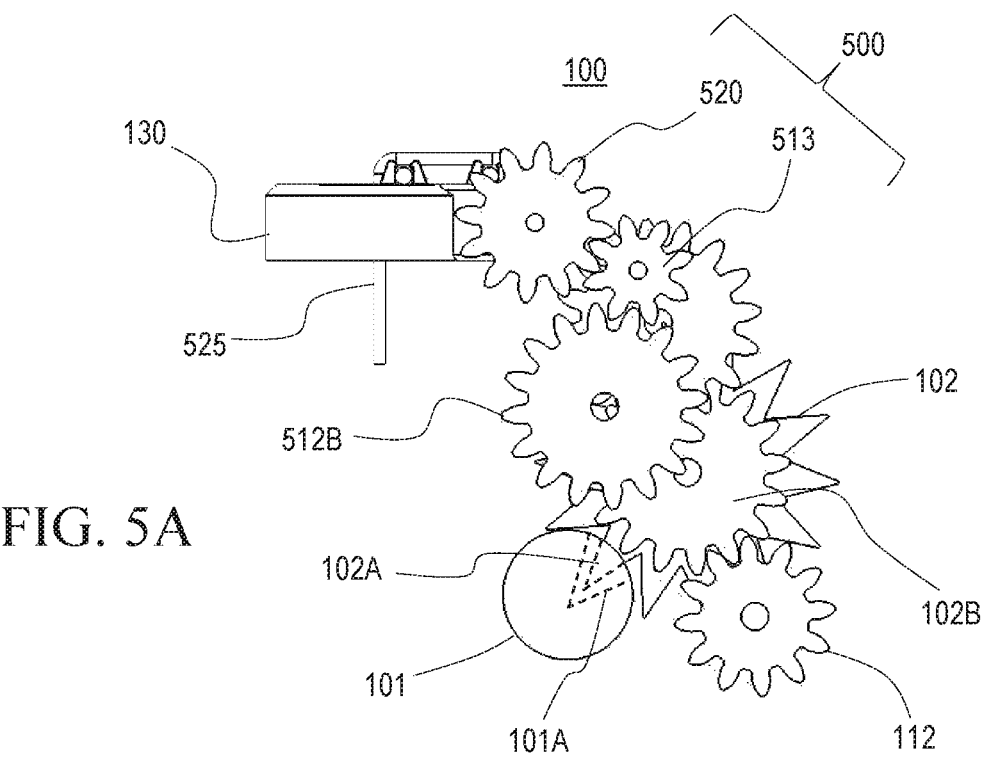
FIGS. 5A-5B are top and bottom views, respectively, of the drive mechanism shown in FIG. 4.
Figure 5B:
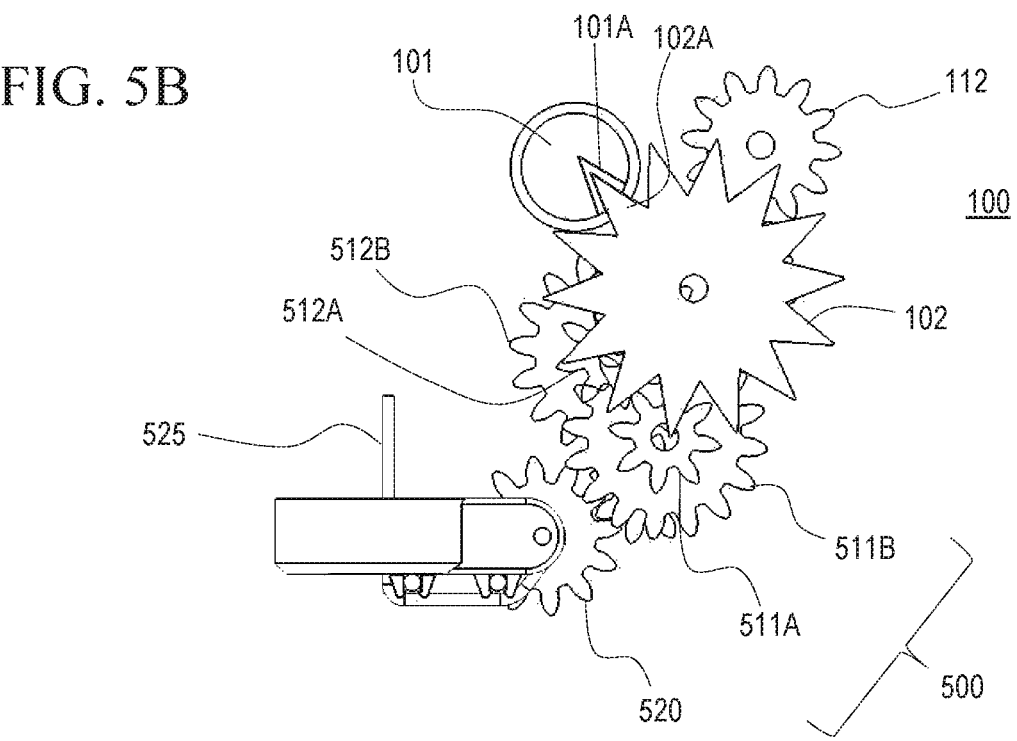
Figure 5C:
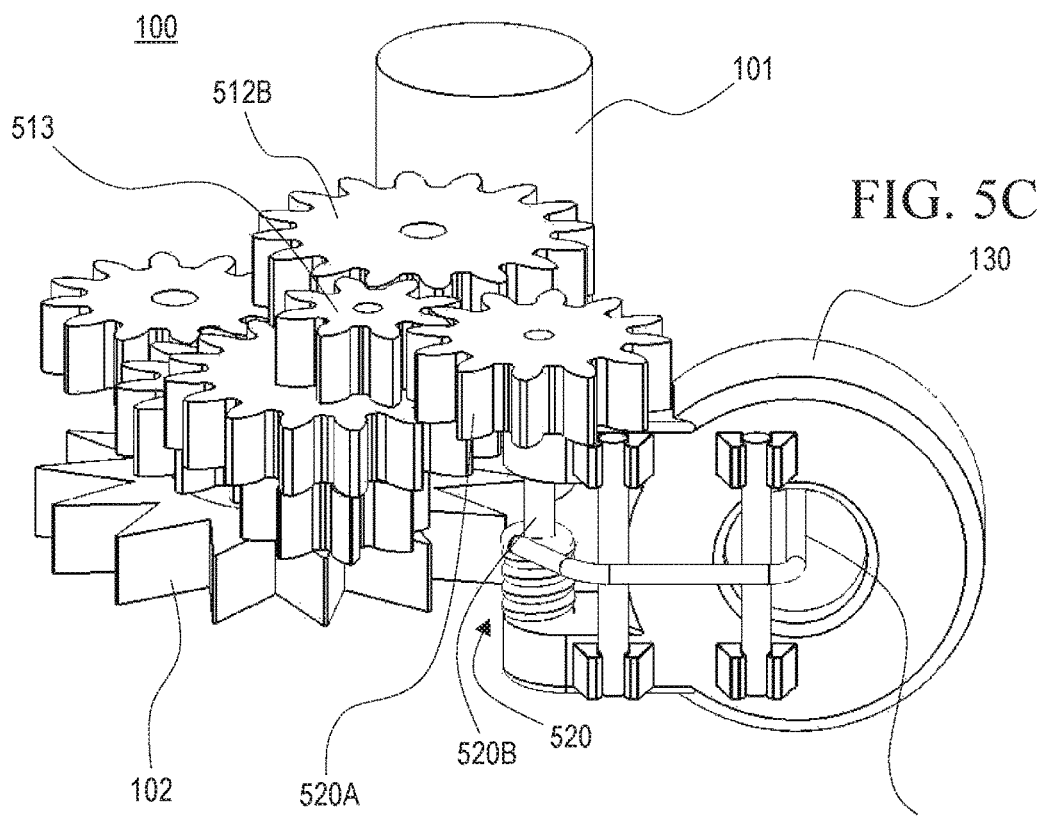
FIGS. 5C-5D are front and back perspective views, respectively, of the drive mechanism shown in FIG. 4.
Figure 5D:
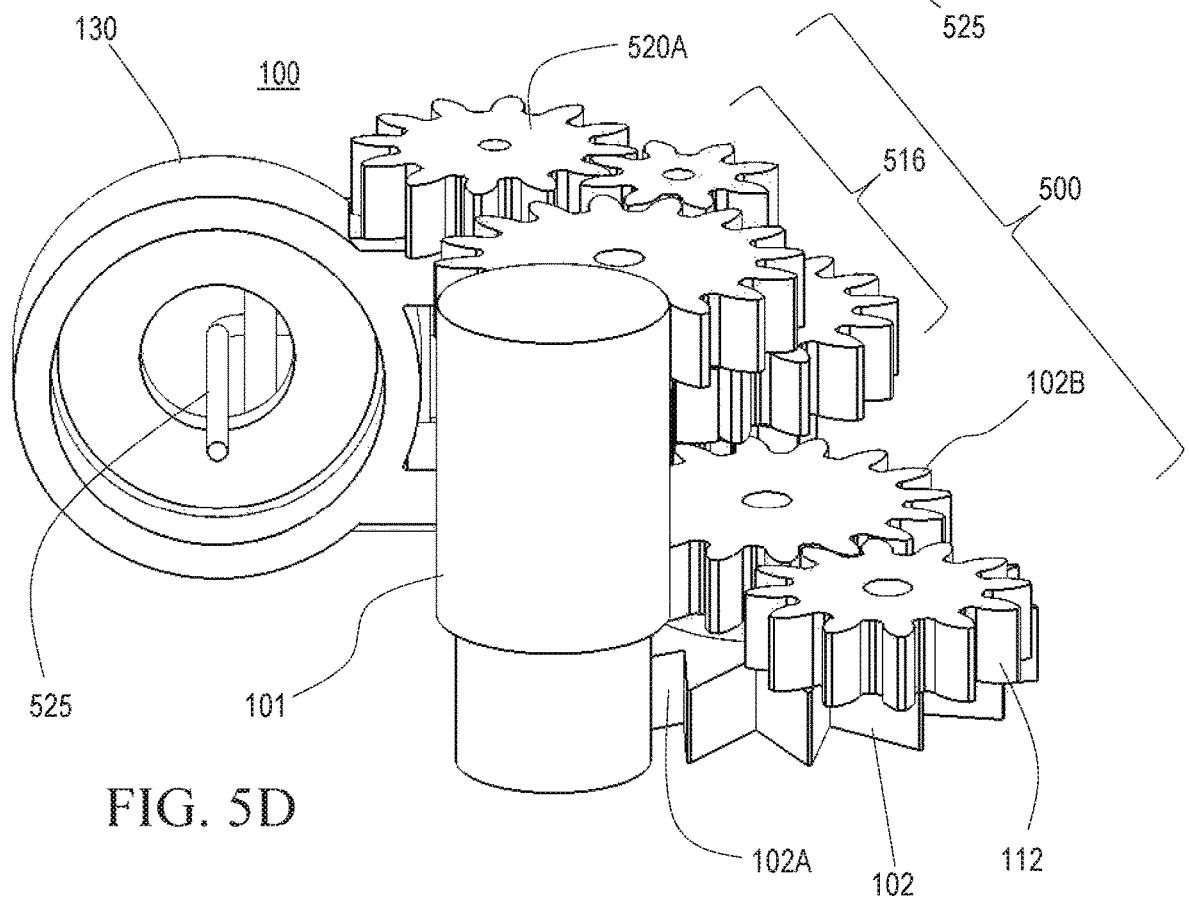

As shown in FIGS. 2A-2E and 3A-3D, and in isolation in FIGS. 4 and 5A-5B, in embodiments of the present invention, the regulating mechanism 500 includes a gear assembly controlled by an actuator 101 of the drive mechanism 100. The regulating mechanism retards or restrains the distribution of tether 525, only allowing it to advance at a regulated or desired rate or according to selected intervals. This restricts movement of piston 110 within barrel 58, which is pushed by one or more biasing members 122, hence, controlling the movement of plunger seal 60 and delivery of the drug contained in chamber 21. As the plunger seal 60 advances in the drug container 50, the drug substance is dispensed through the sterile pathway connection 300, conduit 30, insertion mechanism 200, and into the target for drug delivery. The actuator 101 may be a number of power/motion sources including, for example, a solenoid, a stepper motor, or a rotational drive motor. In a particular embodiment, the actuator 101 is a rotational stepper motor engaged with a gear interface such as a shaft with a notch that corresponds with the gear teeth of the main/star gear 102. In at least one embodiment, the notch of the gear interface forms a recess within which one or more teeth of the main gear may partially reside during operation of the system. This is more clearly visible in FIGS. 5A-5B. When the gear interface 101A is in alignment with a tooth 102A of the main gear 102, rotational motion of the motor 101 allows rotation of the main gear 102. When the notch is between gear teeth of the main gear, it may act as a resistance for, for example, rotation, back-spinning or unwinding of the gear assembly 116. In one particular embodiment, the motor 101 utilizes an alternating direction type motor to rotate the motor 101 backwards and forwards. This configuration aids in the prevention of a runaway condition, where the motor and the gears are freely permitted to rotate, by using the multi-direction of the motor to prevent continuous spin in one direction (as would be needed for a runaway condition). Further, because main gear 102 is only able to advance when a tooth 102A is aligned with the notch of the gear interface 101A, main gear 102 is only able to incrementally rotate. The bi-directional movement of the motor, coupled with the use of the gear interface coupled to the motor, provide suitable safety features to prevent a runaway condition that could potentially lead to over-delivery of drug to the target. Further detail about the gear assembly 116, regulating mechanism 500, and drive mechanism 100 are provided herein. In a particular embodiment shown in FIGS. 5A-5B, the regulating element 500 further includes one or more gears 511, 512, 513, 514, of a gear assembly 516. One or more of the gears 511, 512, 513, 514 may be, for example, compound gears having a small diameter gear attached at a shared center axis to a large diameter gear. Gear 513 may be rotationally coupled to winch gear 520A, thereby coupling rotation of gear assembly 516 to winch assembly 520. Compound gear 512 engages the small diameter gear 513 such that rotational movement of the compound gear aspect 512B is conveyed by engagement of the gears (such as by engagement of corresponding gear teeth) to gear 513. Gear aspect 512A is engaged with gear aspect 512B, thereby coupling rotation of compound gear 512 with compound gear 511. Compound gear aspect 511A, the rotation of which is coupled to gear aspect 511B, is caused to rotate by action of compound gear aspect 102B of the main/star gear 102A. Compound gear aspect 102B, the rotation of which is coupled to main/star gear 102A, is caused to rotate by interaction between main/star gear 102A and interface 101A of the actuator 101. Thus, rotation of main/star gear 102A is conveyed to winch assembly 520. Accordingly, rotation of the gear assembly 516 initiated by the actuator 101 may be coupled to winch assembly 520 (i.e., through the gear assembly 516), thereby controlling the distribution of tether 525, and the rate of movement of plunger seal 60 within barrel 58 to force a fluid from drug chamber 21. The rotational movement of the winch assembly 520, and thus the axial translation of the piston 110 and plunger seal 60, are metered, restrained, or otherwise prevented from free axial translation by other components of the regulating element 500, as described herein. As described above, the actuator 101 may be a number of known power/motion sources including, for example, a motor (e.g., a DC motor, AC motor, or stepper motor) or a solenoid (e.g., linear solenoid, rotary solenoid). One of skill in the art will recognize that regulating mechanism 500 may include any number of gears to achieve the desired gear ratio. The regulating mechanism may provide any desirable gear ratio between main gear 102A and winch gear 520A. The gear ratio may, for example, be selected based on the desired drug delivery profile. Additionally, the resolution of the gear assembly may be configured based on the number of teeth of main gear 102. The more teeth that main gear 102 has, the finer the resolution of the gear assembly. Conversely, if the main gear 102 has fewer teeth the gear assembly will have a coarser resolution (i.e., more drug fluid will be delivered per each rotation of the actuator).

Figure 6B:
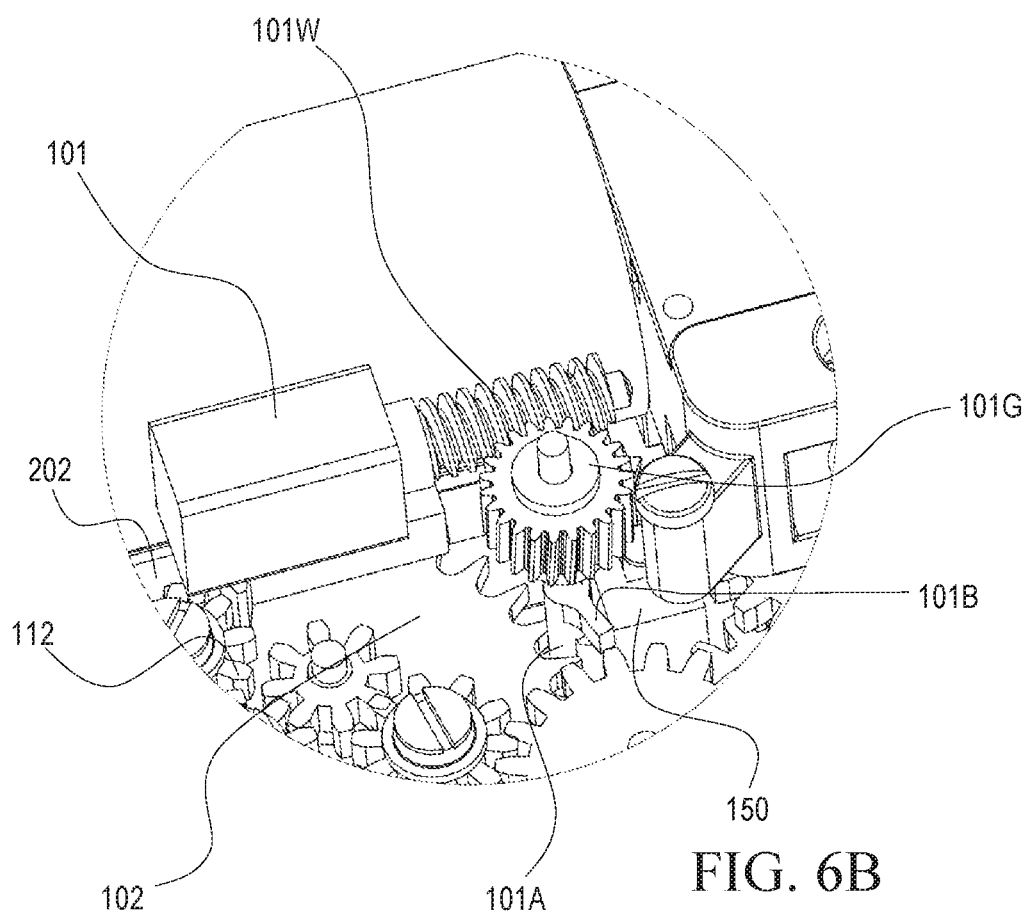
FIG. 6B is an enlarged view of the drive mechanism shown in FIG. 6A

The embodiment described above and shown in FIGS. 1A-5D show an actuator 101 that is in vertical alignment and in direct engagement with gear interface 101A and, thereby, the main/star gear 102. As would readily be appreciated by one having ordinary skill in the mechanical arts, the actuator 101 could be modified to be in horizontal alignment. Additionally or alternatively, the actuator 101 could be modified to be in indirect engagement with the gear interface 101A and main/star gear 102. The embodiments shown in FIGS. 6A-6B show an actuator 101 that is in horizontal alignment and indirect engagement with the gear interface 101A and main/star gear 102. Such an embodiment may utilize a rack and pinion engagement, a drive screw, or a worm gear 101W, as shown in FIGS. 6A-6B, to change the direction of motion from horizontal to vertical (i.e., perpendicular interaction). Actuator 101 rotates worm gear 101W, which engages gear 101G and conveys the motion to the gear interface 101A, in this embodiment a shaft with a notch. The gear interface 101A engages main/star gear 102 to enable operation of the drive mechanism and the drug delivery device, as described herein. Main/star gear 102 may also drive operation of gear 112 to enable operation of the needle insertion mechanism 200, as described herein. In one particular embodiment, the actuator 101 utilizes an alternating direction type motor to rotate the worm gear 101W, gear 101G, and gear interface 101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 101, coupled with the use of the worm gear 101W, gear 101G, and gear interface 101A with the main/star gear 102, provide suitable safety features to prevent a runaway condition that could potentially lead to over-delivery of drug to the target. Additionally, the gear interface 101A may include a stop member 101B that stops the rotation of the gear interface 101A against a stop block 150. Stop block 150 further prevents over-rotation of the gear interface 101A and, accordingly, the main/star gear 102 to prevent a runaway condition that could potentially lead to over-delivery of drug to the target. For the device to function in this configuration, the gear interface 101A must be rotated backwards in the other direction before rotating forwards again to progress the main/star gear 102 because the stop member 101B prevents over rotation in one direction by interaction with the stop block 150. Additionally, the geometry of worm gear 101W may be configured such that it is self-locking and/or cannot be back-driven by gear 101G. This may be done by configuration of parameters such as: pitch, lead angle, pressure angle, and number of threads. In so doing, runaway conditions of the drive mechanism will be prevented by the worm gear's resistance to rotations that are not caused by actuator 101.

Figure 15A:
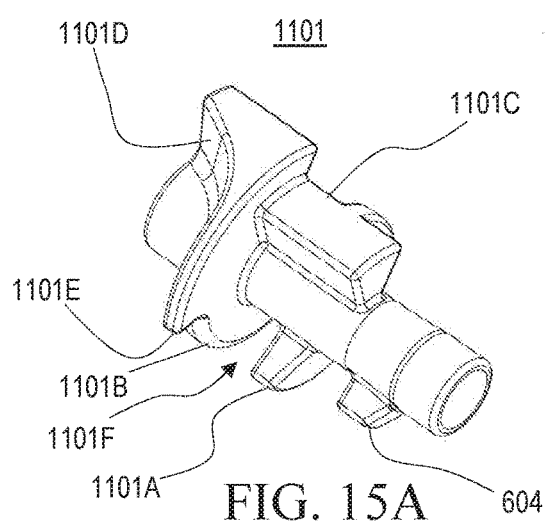
FIGS. 15A-15B are isometric views of a key according to at least one embodiment of the present invention.
Figure 15B:
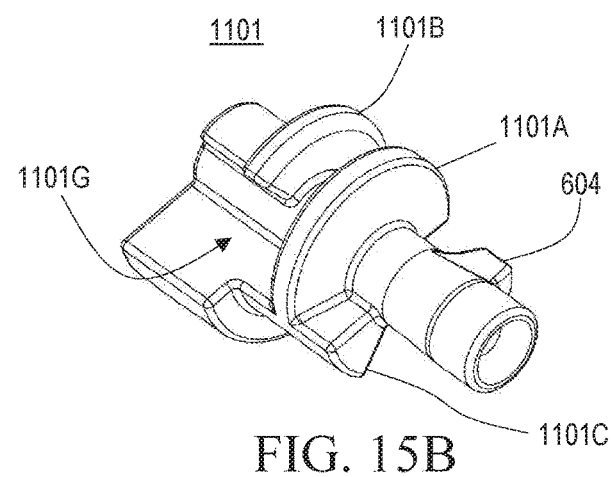

In another embodiment, the actuator 101 is rotationally coupled to a gear interface such as a key 1101, such as that shown in FIGS. 15A-15B. The actuator may be an alternating direction type motor as described above. The key 1101 may be a shaft with one or more flanges 1101A, 1101B, which interface with main gear 1102. The first flange 1101A and second flange 1101B are offset along the length of the shaft. Alternating clockwise and anti-clockwise rotation of the key 1101 allows stepwise rotation of the main gear 1102. In the embodiment shown, the key 1101 has two flanges but it is contemplated that the key 1101 may include any number of flanges. As shown, the key 1101 may further include a rotation limiter 1101C and a status reader interface 1101D. The second flange 1101B may further include a step 1101E. These features are configured to interact with the main gear 1102 during operation to control rotation of the gear assembly 1516 and, optionally, interact with a status reader 1550 to monitor the rotation of the regulating mechanism 1500. The rotation limiter 1101C and status step 1101E are configured such that contact of these features with the main gear 1102 restricts continued rotation of the key.

Figure 16:
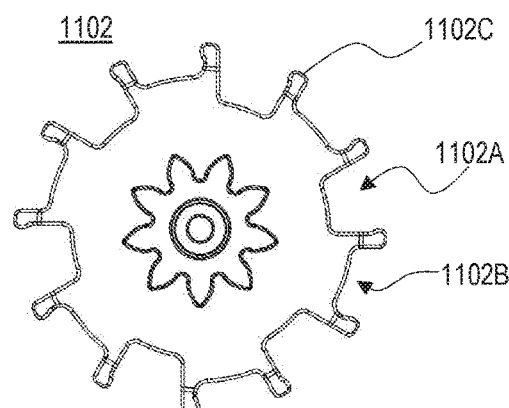
FIG. 16 is a plan view of a main gear according to at least one embodiment of the present invention.

As shown in FIG. 16, the main gear 1102 includes variable pass-throughs that allow passage of the flanges 1101A, 1101B of the key 1101 and, thereby, rotation of the key 1101. As shown, the main gear 1102 may include cyclically alternating large 1102A and small 1102B pass-throughs, each separated by a tooth 1102C. The size of the pass-throughs may be configured to control rotation of the key 1101 to allow operation of the regulating mechanism 1500 to be monitored, as will be described further hereinafter.

Figure 17A:
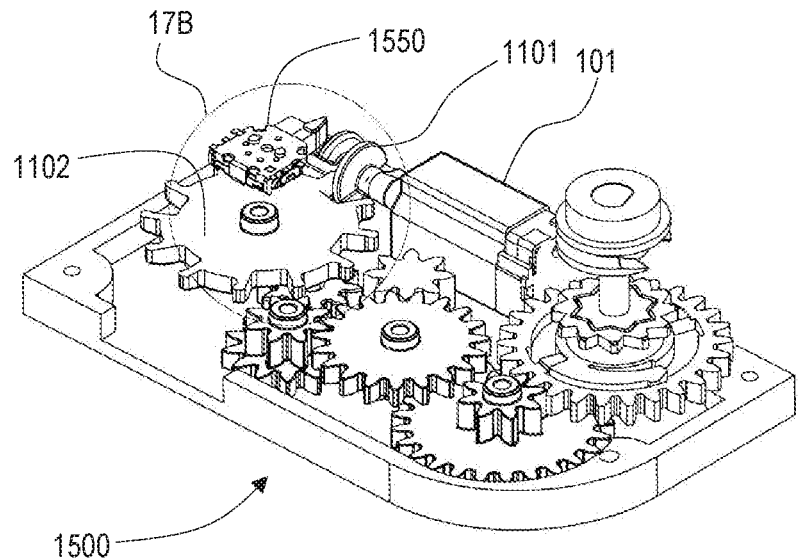
FIG. 17A is an isometric view of a drive mechanism according to one embodiment of the invention in a first configuration.
Figure 17B:
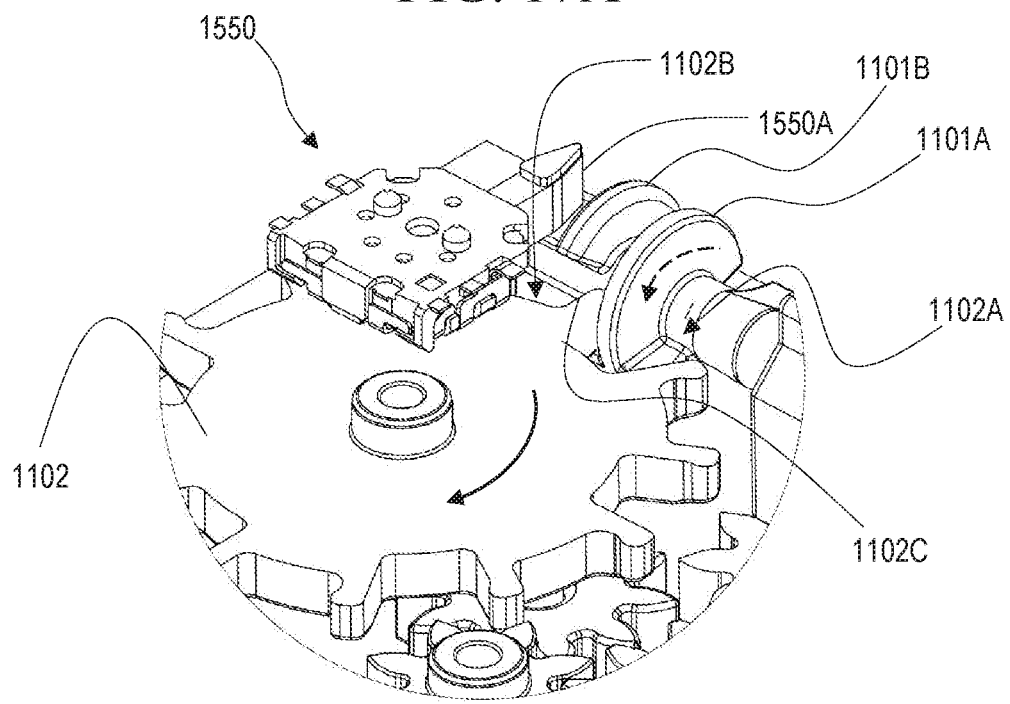
FIG. 17B is an enlarged, fragmentary, isometric view of the drive mechanism of FIG. 17A in the first configuration.

The steps of operation of the key 1101 and main gear 1102 are described further with reference to FIGS. 17A-20B. Although sequential terms such as first, second, third, and fourth are used to describe the stages of operation, these terms are used for explanatory purposes only. The key and gear train may begin in any of the described configurations. FIGS. 17A-17B show the key 1101 and main gear 1102 in a first configuration. A tooth of the main gear 1102 is contacting the first flange 1101A of the key 1101 and rotation of the main gear 1102 is thereby restricted. A portion of the first flange 1101A of the key 1101 is disposed in a large pass-through 1102A of the main gear 1102. The tension applied to the tether by the drive biasing member applies a torque to the main gear (through the regulating mechanism 1500) that is in the direction of the solid arrow shown in FIG. 17B. The contact between the tooth 1102C of the main gear 1102 and the first flange 1101A of the key resists rotation in this direction.

Figure 18A:
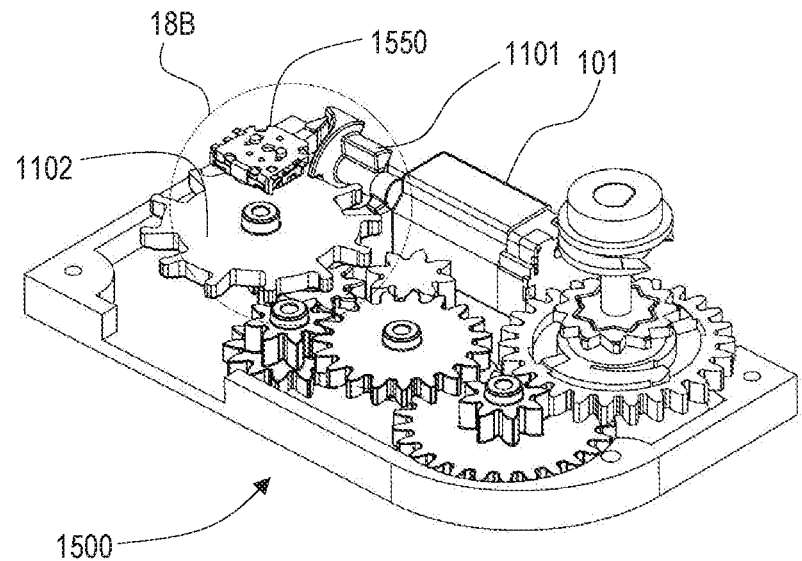
FIG. 18A is an isometric view of the drive mechanism of FIG. 17A in a second configuration.
Figure 18B:
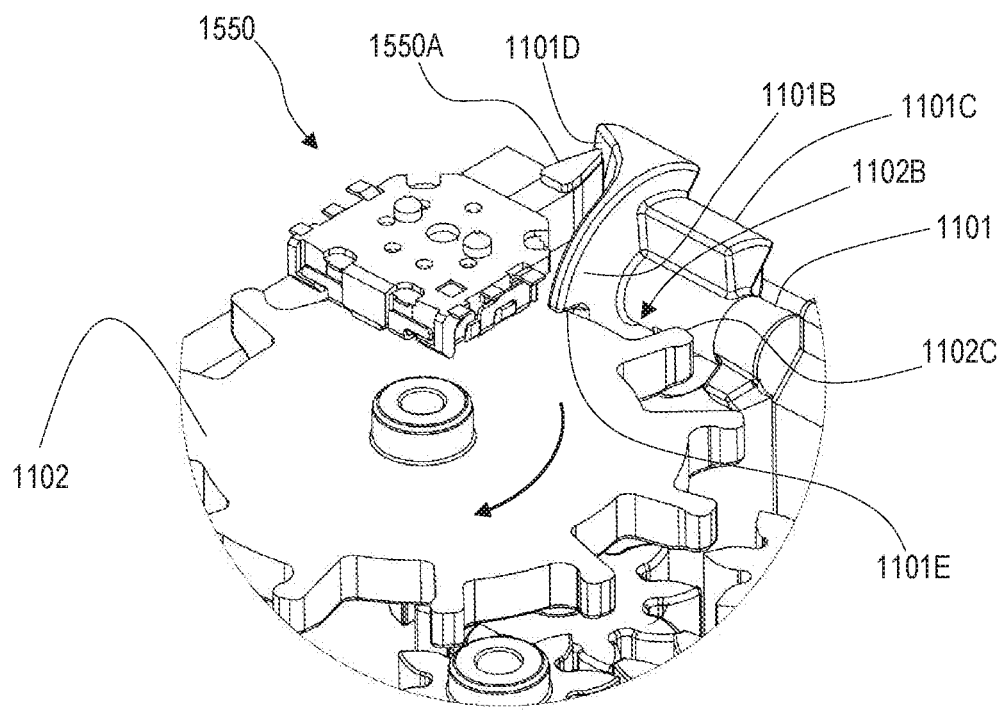
FIG. 18B is an enlarged, fragmentary, isometric view of the drive mechanism of FIG. 18A in the second configuration.

To allow the main gear 1102 to advance, the key 1101 may be rotated such that the first aperture 1101F of the first flange 1101A is aligned with the tooth 1102C of the main gear 1102. In the embodiment shown, the rotation is in the direction of the dashed arrow of FIG. 17B. The amount of rotation of the key 1101 will be limited by contact of the step 1101E of the second flange 1101B with the main gear 1102. In this position, the key 1101 is not preventing rotation of the main gear 1102 as no teeth of the main gear are in contact with the key. If the regulating mechanism 1500 is operating properly, the tension on the tether will cause the main gear 1102 to rotate (in the direction of the solid arrow of FIG. 17B) until a tooth 1102C of the main gear 1102 comes into contact with the second flange 1101B of the key 1101. Hence, the main gear 1102 advances a controlled amount, allowing the rotation of the key 1101 to control unspooling of the tether and translation of the piston. As shown in FIGS. 18A-18B, in this position, the contact between the step 1101E of the second flange 1101B and the main gear 1102 restricts rotation of key 1101 and, thereby, prevents the status reader interface 1101D from coming into contact with the status reader 1550.

Figure 19A:
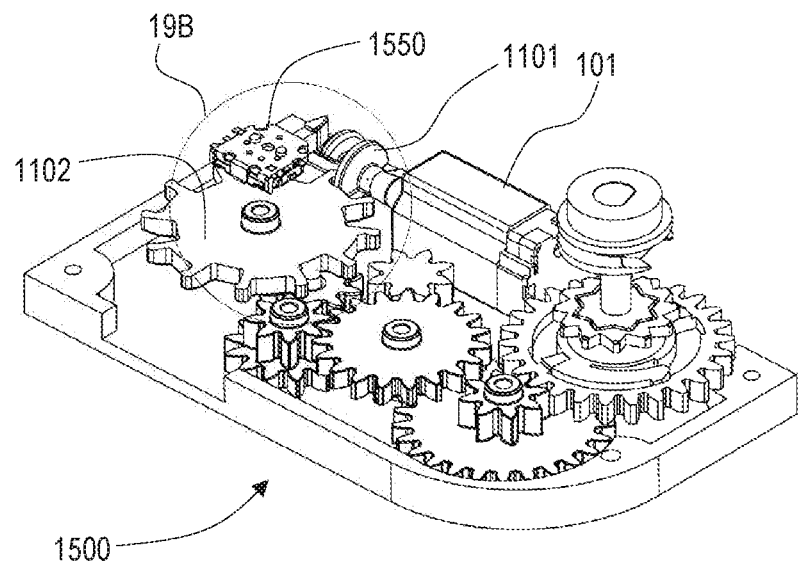
FIG. 19A is an isometric view of the drive mechanism of FIG. 17A in a third configuration.
Figure 19B:
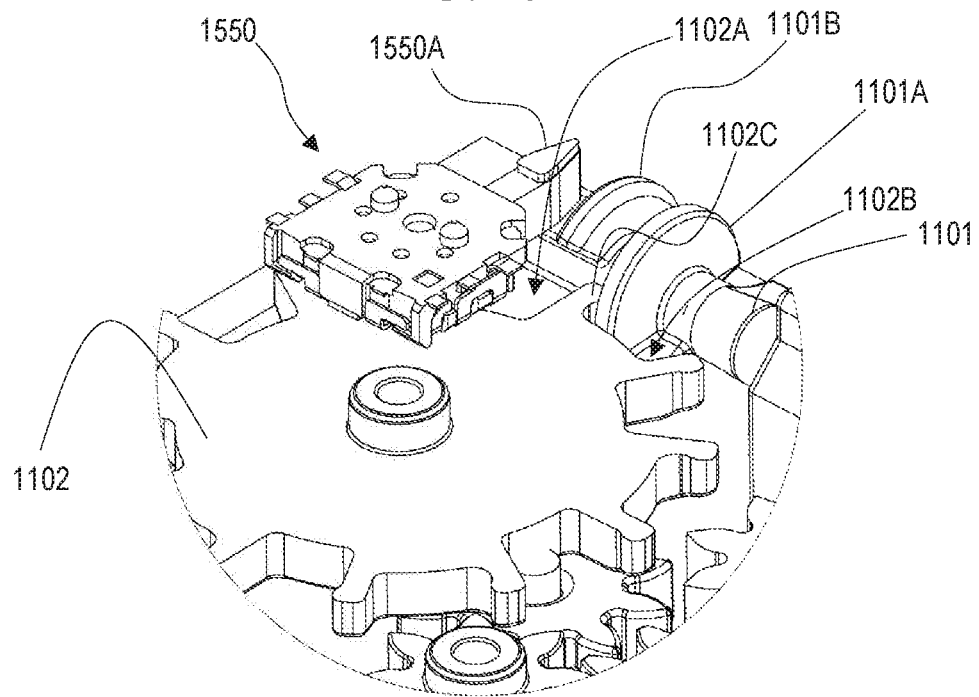
FIG. 19B is an enlarged, fragmentary, isometric view of the drive mechanism of FIG. 19A in the third configuration.

From this position, the main gear 1102 may be allowed to advance another step by rotation of the key 1101 in the opposite direction to that rotated previously. For example, if the key was rotated in an anti-clockwise direction to transform from the first position to the second position, the key would now be rotated in a clockwise direction to transform from the second position to the third position. After rotation of the second flange 1101B past the main gear 1102 such that the second aperture 1101G is aligned with the main gear 1102, the tooth 1102C of the main gear 1102 that was in contact with the second flange 1101B is able to advance until it comes in contact with the first flange 1101A. This, third position, is shown in FIGS. 19A-19B. In this position, the first flange 1101A is disposed in a small pass-through 1102B of the main gear 1102 and the second flange 1101B is aligned with, but not disposed in, a large pass-through 1102A of the main gear 1102.

Figure 20A:
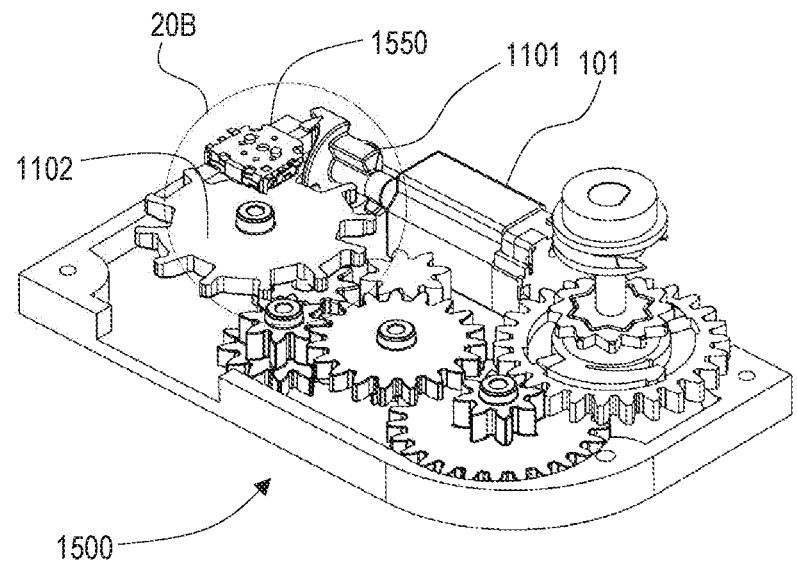
FIG. 20A is an isometric view of the drive mechanism of FIG. 17A in a fourth configuration.
Figure 20B:
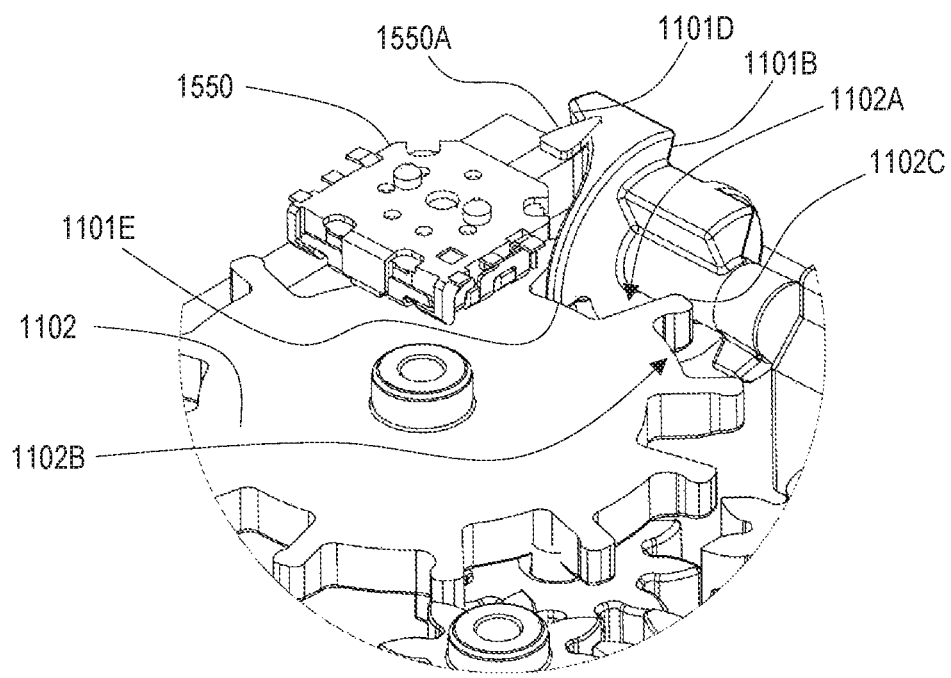
FIG. 20B is an enlarged, fragmentary, isometric view of the drive mechanism of FIG. 20A in the fourth configuration.

Rotation of the key 1101 will again allow advancement of the main gear 1102. In transforming from the third position to the fourth position, however, the step 1101E of the second flange 1101B will not make contact with the main gear 1102 as the large pass-through 1102A of the main gear 1102 is configured to allow passage of the step 1101E (i.e., the large pass-through is large enough to allow the step to pass through it). Hence, as shown in FIGS. 20A-20B, in the fourth position, the status reader interface 1101D of the key 1101 contacts the status reader 1550. This contact causes a signal to be sent to the power and control system. The status reader may be, for example, a detector switch which creates or modifies an electrical signal upon contact with, or displacement of, the status reader arm 1550A. The status reader 1550 may be mounted to the housing 12 or top plate 1530 and be in electrical communication with the power and control system.

In this way, the operation of the regulating mechanism may be monitored. In the embodiment described above, when the main gear 1102 is operating properly, the key 1101 will contact the status reader 1550 at a predefined rotation interval during operation, for example once every four rotations of the key 1101. However, if the main gear 1102 is not rotating properly, the key 1101 will contact the status reader 1550 at some other interval or not contact the status reader at all. For example, if the main gear 1102 stops rotating in a position, wherein the second flange 1101B is aligned with a large pass-through 1102A of the main gear 1102, the key 1101 will contact the status reader 1550 every other rotation of the key 1101 (i.e., each time the key is rotated in the direction of the dashed arrow in FIG. 17B). Alternatively, if the main gear 1102 stops rotating in a position wherein the second flange 1101B is aligned with a small pass-through 1102B of the main gear 1102, the key 1101 will be prevented from contacting the status reader 1550. Hence, the power and control system can compare the frequency of contact between the key and the status reader with an expected frequency and determine whether the regulating mechanism is operating properly.

This may provide safety advantages to the target. For example, if the key 1101 rotates four times and the power and control system does not receive a signal from the status reader 1550, the power and control system may terminate delivery of medicament to the target. Similarly, if the power and control system receives a signal from the status reader 1550 after only two rotations, this would also signal a fault in the regulating mechanism and initiate termination of delivery. The power and control system may terminate delivery by activating one or more actions such as retraction of the needle or cannula from the target.

While the embodiment described above is configured such that the key 1101 contacts the status reader 1550 once every four rotations, these components may be configured for any frequency of activation by, for example, varying the distribution of large 1102A and small 1102B pass-throughs in the main gear 1102.

Further, the key 1101 may be configured to provide additional advantages in preventing runaway drug delivery scenarios. In the embodiment shown in FIGS. 15A-15B, the key 1101 is configured such that the main gear 1102 is only able to rotate one rotational increment at a time. At all times, because first aperture 1101F and second aperture 1101G are not aligned (i.e., they are offset around the circumference of the shaft), at least one of the first flange 1101A and the second flange 1101B is positioned to prevent rotation of the main gear 1102 by being in the path of travel of the teeth 1102C of the main gear 1102. Further, in the embodiment shown, the flanges 1101A, 1101B of the key 1101 are oriented substantially perpendicular to the path of travel of the teeth 1102C of the main gear. Hence, the force applied to the key by the main gear does not impart a torque on the key and therefore the key 1101 cannot be backdriven by the main gear 1102. Hence, rotation of the main gear 1102 will be restricted by the key 1101 even when the actuator 101 is not powered to prevent rotation of the key 1101.

Figure 15C:
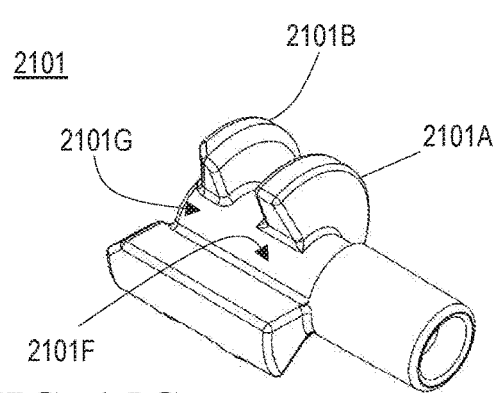
FIG. 15C is an isometric views of a key according to another embodiment of the present invention.

The drive mechanism may also be configured to allow unrestrained unspooling of the tether. FIG. 15C shows an embodiment of a key 2101 which would allow such a configuration of the drive mechanism. As shown, aperture 2101F of first flange 2101A is circumferentially aligned with aperture 2101G of second flange 2101B. Hence, upon rotation of key 1101, tooth 1102C of main gear 1102 is aligned with both apertures. This allows main gear 1102 to rotate freely, without being restrained by key 2101. As a result, biasing member 122 is able to expand without being restrained by the tether. This results in substantially all of the contents of the drug container being delivered at one time, at a rate controlled by the stiffness of the biasing member and the pneumatic/hydraulic resistance of the system. The versatility of being able to configure the drug delivery device to deliver a metered drug profile over an extended period as described above or, alternatively, to deliver the drug in a single, relatively short dose provides a number of advantages. Specifically, it allows the device to use like components across a platform of drug delivery devices, thereby providing economies of scale in terms of component and assembly prices.

Notably, the regulating mechanisms 500, 1500 and actuators 101 of the present invention do not drive the delivery of fluid substances from the drug chamber 21. The delivery of fluid substances from the drug chamber 21 is caused by the expansion of the biasing member 122 from its initial energized state acting upon the piston 110 and plunger seal 60. The regulating mechanisms 500, 1500 instead function to provide resistance to the free motion of the piston 110 and plunger seal 60 as they are pushed by the expansion of the biasing member 122 from its initial energized state. The regulating mechanism 500, 1500 does not drive the delivery but only controls the delivery motion. The tether limits or otherwise restrains the motion of the piston 110 and plunger seal 60, but does not apply the force for the delivery. According to a preferred embodiment, the controlled delivery drive mechanisms and drug pumps of the present invention include a regulating mechanism indirectly or directly connected to a tether metering the axial translation of the piston 110 and plunger seal 60, which are being driven to axially translate by the biasing member 122. The rate of drug delivery as controlled by the regulating mechanism may be determined by: selection of the gear ratio of gear assembly 516; selection of the main/star gear 102; selection of the diameter of winch drum 520B; using electromechanical actuator 101 to control the rate of rotation of the main/star gear 102, 1102; or any other method known to one skilled in the art. By using electromechanical actuator 101 to control the rate of rotation of the main/star gear 102, 1102 it may be possible to configure a drug pump to provide a variable dose rate (i.e., the rate of drug delivery is varied during a treatment).

In another embodiment, the power and control system of the drug pump is configured to receive one or more inputs to meter the release of the tether 525 by the winch assembly 520 and thereby permit axial translation of the piston 110 by the biasing member 122 to translate a plunger seal 60 within a barrel 58. The one or more inputs may be provided by the actuation of the activation mechanism, a control interface, and/or a remote control mechanism. The power and control system may be configured to receive one or more inputs to adjust the restraint provided by the tether 525 and winch assembly 520 on the free axial translation of the piston 110 upon which the biasing member 122 bears upon to meet a desired drug delivery rate or profile, to change the dose volume for delivery to the target, and/or to otherwise start, stop, or pause operation of the drive mechanism. For example, if the power and control system has determined that the pump is not operating properly, the power and control system may terminate rotation of actuator 101.

The components of the drive mechanism 100, upon activation, may be used to drive axial translation in the distal direction of the plunger seal 60 of the drug container 50. Optionally, the drive mechanism 100 may include one or more compliance features which enable additional axial translation of the plunger seal 60, for example, to ensure that substantially the entire drug dose has been delivered to the target. For example, the plunger seal 60, itself, may have some compressibility permitting a compliance push of drug fluid from the drug container.

The novel controlled delivery drive mechanisms of the present invention may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. As the end-of-dose indication is tied to the piston reaching the end of its axial translation, the drive mechanism and drug pump provide a true end-of-dose indication to the user.

The tether 525 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 525 that would contact the status reader at the end of axial travel of the piston 110 and plunger 60 within the barrel 58 of the drug container 50. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 525 to be read or recognized at positions which correspond with the beginning and end of drug delivery, as well as at desired increments during drug delivery. As the drug pump is activated and drug delivery is begun by release of the biasing member 122 and the resulting force applied to the piston 110 and plunger seal 60, the rate or profile of drug delivery to the target is controlled by the regulating mechanism 500, gear assembly 516, and winch assembly 520 releasing the tether 525 and permitting expansion of the biasing member 122 and axial translation of the piston 110 and plunger seal 60. As this occurs, the status triggers of the tether 525 are contacted or recognized by the status reader and the status of the drive mechanism before, during, and after operation can be relayed to the power and control system to provide feedback to the user. Depending on the number of status triggers located on the tether 525, the frequency of the incremental status indication may be varied as desired. As described above, a range of status readers may be utilized depending on the status triggers utilized by the system.

In a preferred embodiment, the status reader may apply a tensioning force to the tether 525. When the system reaches end-of-dose, the tether 525 goes slack and the status reader 544 is permitted to rotate about a fulcrum. This rotation may operate an electrical or electromechanical switch, for example a switch, signaling slack in the tether 525 to the power and control system. Additionally, a gear of gear assembly may act as an encoder along with a sensor. The sensor/encoder combination is used to provide feedback of gear assembly rotation, which in turn can be calibrated to the position of piston 110 when there is no slack in the tether 525. For example, rotation of main gear 102, 1102 may be configured to be monitored by an optical sensor. A reflective surface coating may be applied to at least a portion of the face of main gear 102, 1102 to improve the accuracy of the optical sensor. Together, the status reader and sensor/encoder may provide positional feedback, end-of-dose signal, and error indication, such as an occlusion, by observing slack in the tether 525 or another component of the drive mechanism prior to reaching the expected number of motor rotations as counted by the sensor/encoder.

Referring back to FIGS. 2A-2E and 3A-3D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the drive mechanisms of the present invention may concurrently or sequentially perform the steps of: triggering a needle insertion mechanism to provide a fluid pathway for drug delivery to a target; and connecting a sterile fluid pathway to a drug container to permit fluid flow from the drug container to the needle insertion mechanism for delivery to the target. In at least one embodiment, as shown in FIGS. 2A-2E and 3A-3D, initial motion by the actuator 101 of the drive mechanism 100 causes rotation of main/star gear 102. Main/star gear 102 is shown as a compound gear with aspects 102A and 102B (see FIG. 4). In one manner, main/star gear 102 conveys motion to the regulating mechanism 500 through gear assembly 516. In another manner, main/star gear 102 conveys motion to the needle insertion mechanism 200 through gear 112. As gear 112 is rotated by main/star gear 102, gear 112 engages the needle insertion mechanism 200 to initiate the fluid pathway connection into the target, as described in detail above. In one particular embodiment, needle insertion mechanism 200 is a rotational needle insertion mechanism. Accordingly, gear 112 is configured to engage a corresponding gear surface 208 of the needle insertion mechanism 200. Rotation of gear 112 causes rotation of needle insertion mechanism 200 through the gear interaction between gear 112 of the drive mechanism 100 and corresponding gear surface 208 of the needle insertion mechanism 200. Once suitable rotation of the needle insertion mechanism 200 occurs, for example rotation along axis 'R' shown in FIG. 2D, the needle insertion mechanism may be initiated to create the fluid pathway connection into the target, as described in detail above.

In an alternative embodiment, as shown in FIGS. 6A-6B, gear 112 may indirectly engage the needle insertion mechanism 200 to initiate the fluid pathway connection into the target. For example, gear 112 may be configured to engage a corresponding gear surface of a control arm 202 (visible in FIGS. 6A and 6B) that contacts or blocks the needle insertion mechanism 200. Rotation of gear 112 causes movement of the control arm 202, which may initiate or permit rotation of needle insertion mechanism 200. Such a needle insertion mechanism, as shown in FIGS. 6A-6B, includes a rotationally biased member 210 which is initially held in an energized state. The rotational biasing member may be prevented from de-energizing by contact of a component of the insertion mechanism with a rotation prevention feature, such as a blocking aspect 206, of the drug pump. Rotation or translation of blocking aspect 206 is initially prevented by contact with control arm 202. Translation of control arm 202, caused by rotation of gear 112, positions control arm 202 such that it no longer prevents rotation of blocking aspect 206. Upon activation of the device, or another input, the rotationally biased member 210 is permitted to, at least partially, de-energize. This causes one or more components of the insertion mechanism to rotate and, in turn, cause, or allow, the insertion of the needle into the target. Further, a cannula may be inserted into the target as described above. At a later time, such as when the control arm or another component of the device recognizes a slack in the tether 525, the rotationally biased member may be allowed to further de-energize, such as by further interaction with the control arm, causing additional rotation of one or more components of the insertion mechanism. This rotation may cause, or allow, the needle to be retracted from the target. The needle may be fully retracted in a single step or there may be multiple steps of retraction.

As shown in FIGS. 2A-2E and 3A-3D, rotation of the needle insertion mechanism 200 in this manner may also cause a connection of a sterile fluid pathway to a drug container to permit fluid flow from the drug container to the needle insertion mechanism for delivery to the target. Ramp aspect 222 of needle insertion mechanism 200 is caused to bear upon a movable connection hub 322 of the sterile fluid pathway connection 300. As the needle insertion mechanism 200 is rotated by the drive mechanism 100, ramp aspect 222 of needle insertion mechanism 200 bears upon and translates movable connection hub 322 of the sterile fluid pathway connection 300 to facilitate a fluid connection therein. Such translation may occur, for example, in the direction of the hollow arrow along axis 'C' shown in FIG. 2B. In at least one embodiment, the needle insertion mechanism 200 may be configured such that a particular degree of rotation upon rotational axis 'R' (shown in FIG. 2D) enables the needle/trocar to retract as detailed above. Additionally or alternatively, such needle/trocar retraction may be configured to occur upon a user-activity or upon movement or function of another component of the drug pump. In at least one embodiment, needle/trocar retraction may be configured to occur upon end-of-drug-delivery, as triggered by, for example, the regulating mechanism 500 and/or one or more of the status readers as described above. During these stages of operation, delivery of fluid substances from the drug chamber 21 may be initiated, on-going, and/or completed by the expansion of the biasing member 122 from its initial energized state acting upon the piston 110 and plunger seal 60. As described above, the regulating mechanism 500 functions to provide resistance to the free motion of the piston 110 and plunger seal 60 as they are pushed by the expansion of the biasing member 122 from its initial energized state. The regulating mechanism 500 does not drive the delivery but only controls the delivery motion. The tether limits or otherwise restrains the motion of the piston 110 and plunger seal 60, but does not apply the force for the delivery. This is visible through the progression of the components shown in FIGS. 2A-2E and 3A-3D. The motion of the piston 110 and plunger seal 60 as they are pushed by the expansion of the biasing member 122 from its initial energized state are shown in the direction of the solid arrow (FIG. 2D) along axis 'A' from proximal or first position 'P' to the distal or second position 'D', as shown in the transition of FIGS. 2A-2E and 3A-3D.

Further aspects of the novel drive mechanism will be described with reference to FIG. 4 and FIGS. 5A-5B. FIG. 4 shows a perspective view of the drive mechanism, according to at least a first embodiment, during its initial locked stage. Initially, the tether 525 may retain the biasing member 122 in an initial energized position within piston 110. Directly or indirectly upon activation of the device by the user, the drive mechanism 100 may be activated to permit the biasing member to impart a force to piston 110 and therefore to tether 525. This force on tether 525 imparts a torque on winch drum 520B which causes the gear assembly 516 and regulating mechanism 500 to begin motion. As shown in FIG. 5A, the piston 110 and biasing member 122 are both initially in a compressed, energized state behind the plunger seal 60. The biasing member 122 may be maintained in this state until activation of the device between internal features of drive housing 130 and interface surface 110C of piston 110. As the drug pump 10 is activated and the drive mechanism 100 is triggered to operate, biasing member 122 is permitted to expand (i.e., decompress) axially in the distal direction (i.e., in the direction of the solid arrow shown in FIG. 2D). Such expansion causes the biasing member 122 to act upon and distally translate interface surface 110C and piston 110, thereby distally translating plunger seal 60 to push drug fluid out of the drug chamber 21 of barrel 58. In at least one embodiment, an end-of-dose status indication may be provided to the user once the status reader contacts or recognizes a status trigger positioned on the tether 525 to substantially correspond with the end of axial travel of the piston 110 and plunger seal 60 within the barrel 58 of the drug container 50. The status triggers may be positioned along the tether 525 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 525 to be read or recognized at positions which correspond with the beginning and end of drug delivery, as well as at desired increments during drug delivery. As shown, tether 525 passes substantially axially through the drive mechanism housing 130, the biasing member 122, and connects to the piston 110 to restrict the axial translation of the piston and the plunger seal 60 that resides adjacent thereto.

The novel embodiments of the present invention may be utilized to meter, restrain, or otherwise prevent free rotational movement of winch drum 520B and, thus, axial translation of the components of the controlled delivery drive mechanism 100. Accordingly, the regulating mechanism 500 only controls the motion of the drive mechanism, but does not apply the force for the drug delivery. One or more additional biasing members 122, such as compression springs, may be utilized to drive or assist the driving of the piston 110. For example, a compression spring may be utilized within the drive housing 130 for this purpose. The regulating mechanism 500 only controls, meters, or regulates such action. The controlled delivery drive mechanisms and/or drug pumps of the present invention may additionally enable a compliance push to ensure that substantially all of the drug substance has been pushed out of the drug chamber 21. The plunger seal 60, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear assembly 516. As the gear assembly 516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present invention. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present invention to provide incremental status indication to the user. While the drive mechanisms of the present invention are described with reference to the gear assembly and regulating mechanism shown in the figures, a range of configurations may be acceptable and capable of being employed within the embodiments of the present invention, as would readily be appreciated by an ordinarily skilled artisan. Accordingly, the embodiments of the present invention are not limited to the specific gear assembly and regulating mechanism described herein, which is provided as an exemplary embodiment of such mechanisms for employment within the controlled delivery drive mechanisms and drug delivery pumps.

In at least one embodiment of the present invention, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present invention, the delivery profile may be adjusted automatically based on one or more inputs. For example, the delivery profile may be adjusted based on activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 101. The change in the rate of movement of actuator 101 causes a change in the rotation rate of regulating mechanism 500, 1500 which, in turn, controls the rate of drug delivery to the target. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the target. Accordingly, one or more embodiments of the present invention are capable of producing a change to the rate of medicament delivery from the drug container thereby providing a dynamic control capability to the drive mechanism and/or the drug delivery device.

In order to quickly prime the drug pump, while conserving energy, the drug pump may include a priming mechanism such as that shown in FIGS. 21A-24. Priming mechanism 700 may allow unwinding of the tether and displacement of the piston without rotation of actuator 101. This displacement of piston 110 may provide at least two benefits. First, any gap that is present between piston 110 and plunger seal 60 after assembly will be quickly closed, bringing the two into contact such that they are ready to begin delivery of the medicament. Second, after piston 110 is brought into contact with plunger seal 60, continued translation of piston 110 will cause commensurate displacement of plunger seal 60. This may allow the primable drug pump containing the priming mechanism to be primed. Upon activation of the fluid pathway connection and the opening of the fluid path from the drug container, translation of plunger seal 60 may cause air or gas that is initially present in fluid pathway connection 300, fluid conduit 30, and needle insertion mechanism 200 to be expelled. This air or gas may be replaced by the medicament contained in the drug container to allow for delivery of the medicament to the target tissue to begin.

In the embodiment shown in FIGS. 21A-24, the priming mechanism includes winch gear 1520 and winch drum 1522. The winch drum 1522 includes coupler 702, capstan 704, and winder 706. Winch gear 1520 is rotationally coupled to the gear interface through the gear assembly. Tether 1525 is wound around capstan 704 and is engaged with winder 706. As a result, tension applied to the tether, by the piston, results in a torque being applied to capstan 704. Capstan 704 is keyed to coupler 702 such that rotation of capstan 704 is transferred to coupler 702. In the embodiment illustrated, external key aspect 704A of capstan 704 is engaged with internal key aspect 702A of coupler 702 to transfer rotation from one component to another. In one embodiment, the key aspects are in the form of complementary teeth. Hence, application of a force to tether 1525 causes a rotational force to be applied to coupler 702 in the direction of the arrow in FIG. 21A.

Figure 21A:
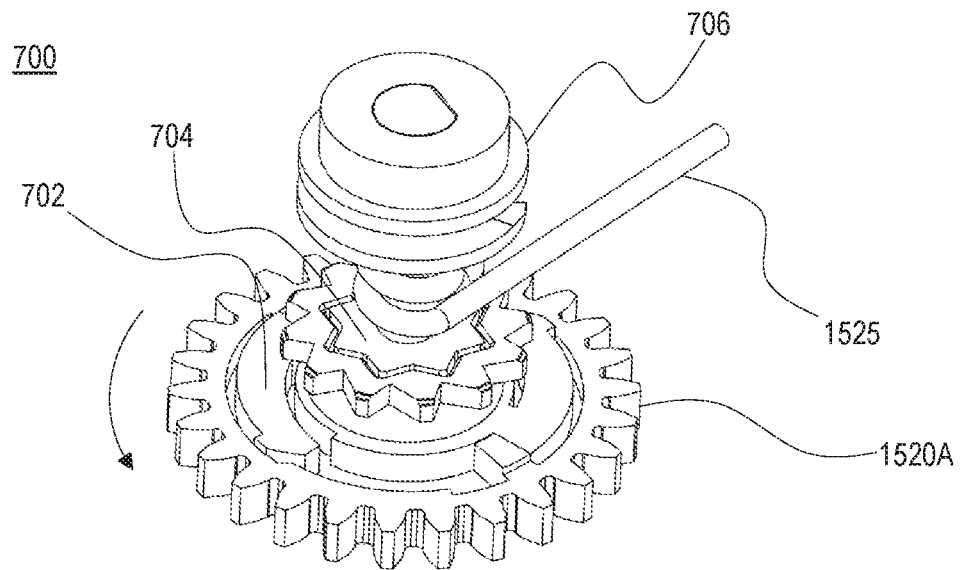
FIG. 21A is an isometric view of one embodiment of a winch drum and winch gear in a first configuration.
Figure 21B:
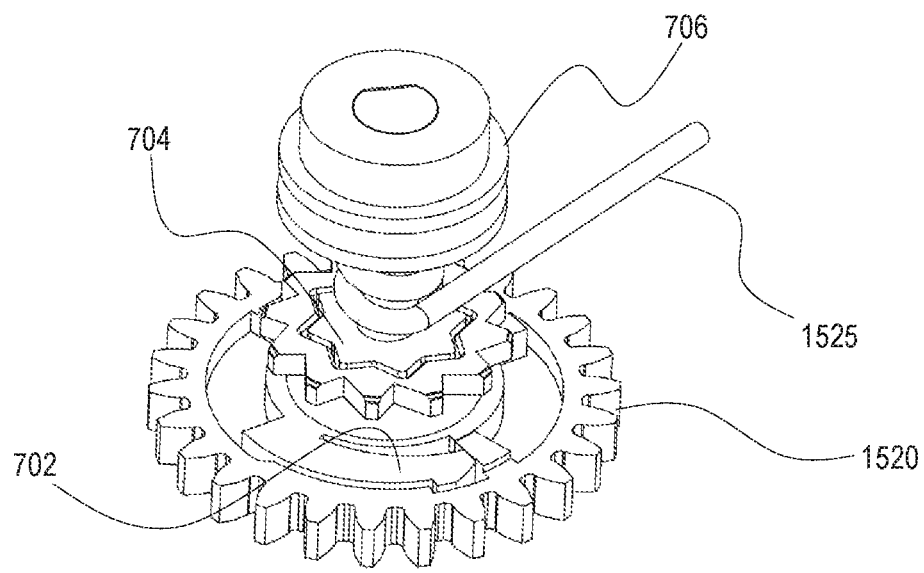
FIG. 21B is an isometric view of the winch drum and winch gear of FIG. 21A in a second configuration.

Winch gear 1520 includes a gear interface such as the spur gear interface 1520A shown in FIG. 22 which is engaged, through gear assembly 116 with actuator 101. Winch gear 1520 further includes hollow 1520E within which coupler 702 is at least partially disposed. Hollow 1520E is configured with features for controlling the rotation of coupler 702, such as ramp 1520D and stop 1520C. Coupler 702, shown in FIG. 23, includes one or more extensions 702B which are configured to be relatively flexible. As shown in FIG. 21A, coupler 702 is initially positioned such that angled face 702C of extension 702B is adjacent to, or in contact with ramp 1520D of winch gear 1520. Contact between angled face 702C and ramp 1520D prevents inadvertent rotation of coupler 702 with respect to winch gear 1520.

One or more components of drug pump 10 form a release mechanism which is initially engaged with release aspect 702D of coupler 702. This engagement initially prevents rotation of coupler 702. The release mechanism may be caused to release rotation of coupler 702 by an action of the user, such as depression of activation mechanism 14. Alternatively, the rotation mechanism may be caused to allow rotation of coupler 702 by an action of power and control system 400. Upon disengagement of the release mechanism, and in response to a torque applied by tether 525, coupler 702 rotates to the position shown in FIG. 21B. In this position, extension 702B is in contact with stop 1520C. This contact prevents further relative rotation of coupler 702 with respect to winch gear 1520 in the direction of the arrow in FIG. 21A. Additionally, extension 702B may engage step 1520F of winch gear 1520 to thereby lock coupler 702 in position with respect to winch gear 1520. With coupler 702 and winch gear 1520 in the configuration shown in FIG. 21B, any further rotation of coupler 702 must be accompanied by commensurate rotation of winch gear 1520. Because winch gear 1520 is engaged with actuator 101 through gear assembly 116, rotation of coupler 702 is also controlled by actuator 101. In this way, the rate of translation of piston 110 and the rate of delivery of medicament can be controlled by actuator 101. Also, the initial translation of piston 110 and rotation of coupler 702, from the position shown in FIG. 21A to that shown in FIG. 21B, allows assembly tolerances to be taken up and the primable drug delivery device to be primed without rotation of the actuator. This allows the primable drug delivery device to conserve energy during this initial stage of operation.

In at least one embodiment, the drug pump and or drive mechanism include one or more safety mechanisms for automatically slowing or terminating the flow of medicament to the target in the event of a fault in delivery. This may be a beneficial feature in the delivery of controlled substances. Some substances, such as insulin, can be harmful or even deadly if delivered in too large a quantity or at too rapid of a delivery rate. The safety mechanisms described herein may be used to ensure that a so-called "run-away" delivery does not occur. For example, means may exist for terminating or restraining the flow of the medicament in the case of slack in, or failure of, the tether during operation.

Figure 32A:
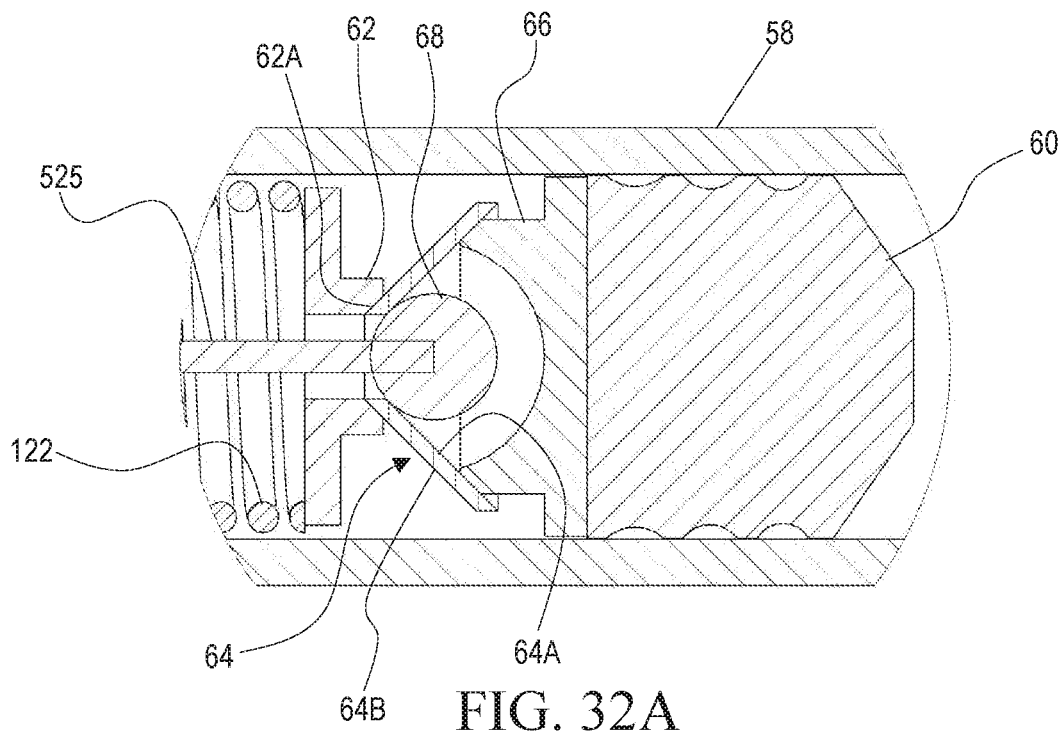
FIG. 32A is a fragmentary cross-sectional view of a drug container and safety mechanism in an initial, unrestrained configuration.
Figure 32B:
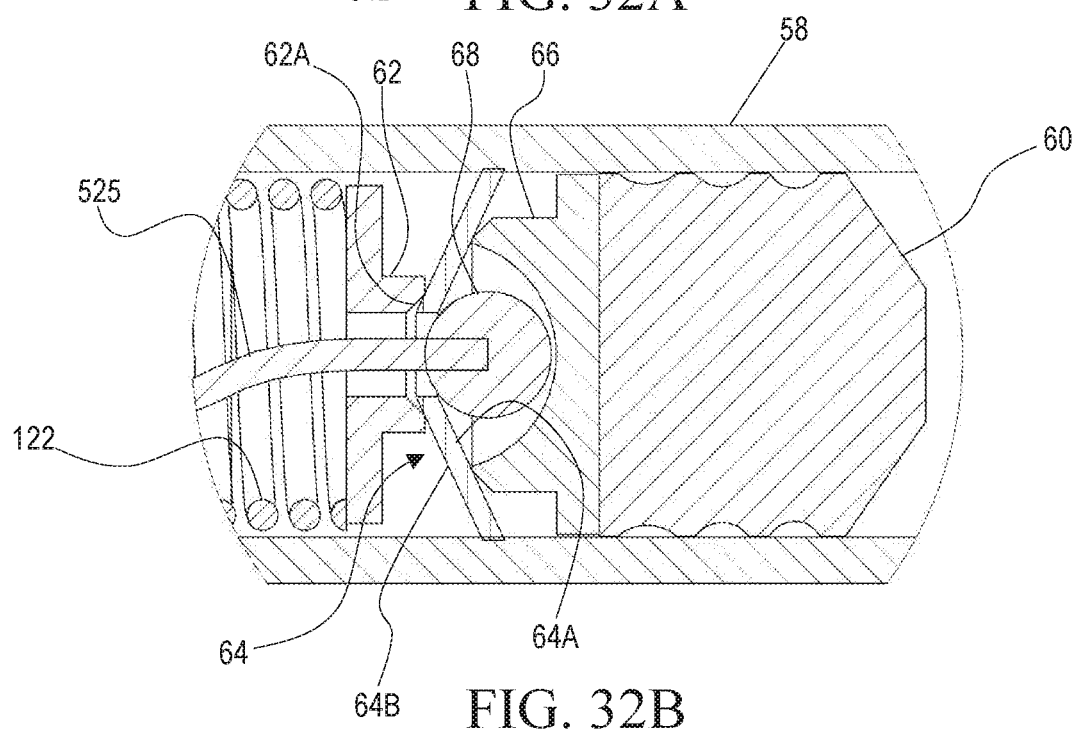
FIG. 32B is a fragmentary cross-sectional view of the drug container and safety mechanism of FIG. 32A in an activated configuration.

In one embodiment, the safety mechanism is a brake mechanism as shown in FIGS. 32A-32B. Disposed within barrel 58 are brake 64, sleeve 62, and plug 68, and optionally retainer 66. Biasing member 122 bears against sleeve 62. Tether 525 is engaged with plug 68, thereby allowing tether 525 to restrain the motion of sleeve 62. This restraint controls the rate of expansion or de-energizing of biasing member 122. When tether 525 is under tension, plug 68 bears against distal face 64A of brake 64, causing proximal face 64B of brake 64 to bear against sleeve 62. Due to this contact, and the profile of the distal end 62A of sleeve 62, brake 64 is maintained in a substantially conical configuration as shown in FIG. 32A. In this configuration, expansion or de-energizing of biasing member 122 is restrained by the tether. Also, in this conical configuration, the outer diameter of brake 64 is less than the inner diameter of barrel 58, thus translation of the brake is not restrained by contact with the inner wall of the drug container. This permits the brake to be in a position that is not sufficient for braking contact with the inner wall of the barrel. Braking contact is contact sufficient to restrain or prevent further de-energizing of the biasing member and does not necessarily require complete contact of the brake with the inner wall of the barrel. Similarly, the brake may be retained in an initial state not in braking contact with the inner wall of the barrel, but does not necessarily require no contact with the inner wall of the barrel. In at least one embodiment, some contact between the brake and the inner wall of the barrel may be desired prior to activation of the brake mechanism, for example to center the brake within the barrel, as long as the brake does not substantially restrain or prevent further de-energizing of the biasing member prior to activation of the brake mechanism. Also, a portion of brake 64 is in contact with retainer 66. Because brake 64 is maintained in this configuration by plug 68 and sleeve 62, translation of sleeve 62, caused by decompression of biasing member 122, is transferred to retainer 66. Likewise, contact of retainer 66 with plunger seal 60 causes translation of plunger seal 60.

As shown in FIG. 32B, in the event of slack in, or failure of, tether 525, plug 68 is no longer held in position by tether 525 and, therefore, no longer restrains motion of sleeve 62. As biasing member 122 decompresses or de-energizes, brake 64 transforms to a relatively less conical or flatter configuration. This may be caused by a natural bias of brake 64 to transform to this configuration or, alternatively, may be caused by contact of brake 64 with both retainer 66 and sleeve 62. As the brake is transformed, it comes into contact with the inner wall of barrel 58. The brake thus acts as a wedge to restrict translation of sleeve 62. This may prevent further translation or may act to restrict the rate of translation. Optionally, restoring tension in the tether may cause the plug to contact the brake and to transform the brake back to its conical configuration and thus restore normal operation of the drug pump.

FIGS. 32A-32B show the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface with the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 62 (i.e., applying a braking force). In another embodiment, the brake 64 could employ a star-shaped or other configuration when in a substantially flattened position so as to make contact with the inner diameter of the barrel 58 to prevent or restrict further axial translation of sleeve 62. Without further translation of sleeve 62, biasing member 122 cannot expand or de-energize further which, in turn, prevents or restricts further drug delivery to the target. This provides a necessary and useful safety measure for drug delivery, to prevent over-delivery or accelerated delivery of drug to the target.

In another embodiment, shown in FIGS. 25A-27B, the safety mechanism may be a plunger seal piercing mechanism 1000 and be positioned at least partially within the barrel 58 or the drive housing 1130. The plunger seal piercing mechanism 1000 may include one or more safety piercing members 1072, a hub 1074, a piston 1110, and a safety biasing member 1078. The piston may additionally have an aperture 1110A through which the tether 1525 may pass and an internal chamber 1110B wherein one or more components of the plunger seal piercing mechanism 1000 may be disposed. The piston may additionally be engaged with a safety base 1076. The base 1076 may include a central aperture 1076A through which the tether 1525 may pass and one or more peripheral apertures 1076B in which the one or more piercing members 1072 may be disposed. The one or more safety piercing members 1072 may be, for example, a hollow needle, such as a stainless steel needle. Alternatively, the piercing members 1072 may be solid trocars. They may also be constructed of any other material such as a thermoplastic or thermosetting polymer. The one or more piercing members 1072 may have a beveled end to increase the efficacy of piercing the plunger seal 1060 and have a lumen 1072B through which material may pass. The one or more piercing members 1072 may be connected to the hub 1074 by any means known to one skilled in the art such as staking, press-fit, and adhesive. Alternatively, the piercing members may be integrally formed portions of the hub. A proximal plug 1070 and a distal plug 1068 may be fixedly engaged with the tether 1525 such that the plugs are fixed in position along the length of the tether 1525. The plugs 1068, 1070 may be, for example, ball cable fittings. Alternatively, they may be an integral feature of the tether 1525. The plunger seal 1060 may include a cavity 1060A within which the distal end 1072A of the one or more piercing members 1072 are initially disposed.

Figure 25A:
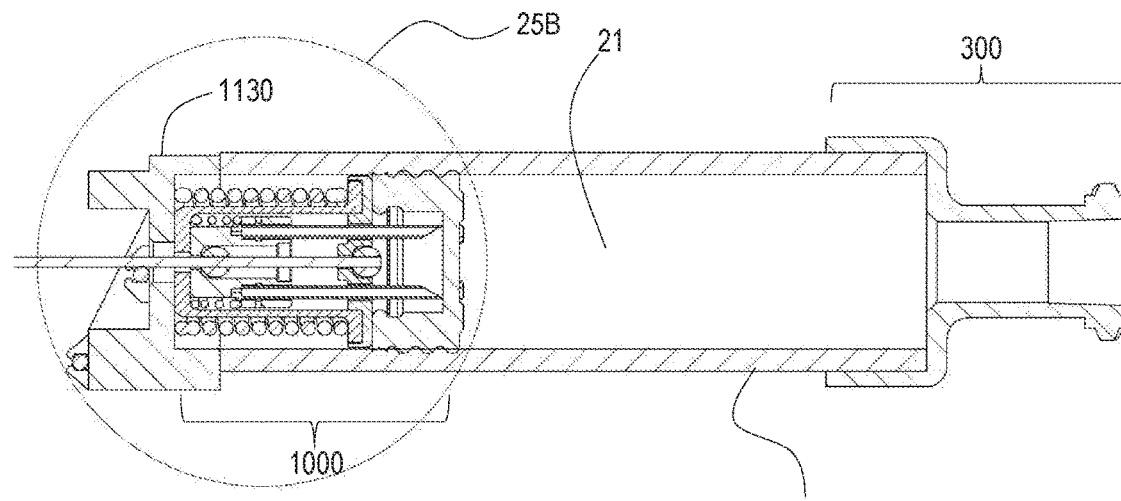
FIG. 25A is a cross-sectional view of a safety mechanism according to one embodiment of the invention in an initial configuration.
Figure 25B:
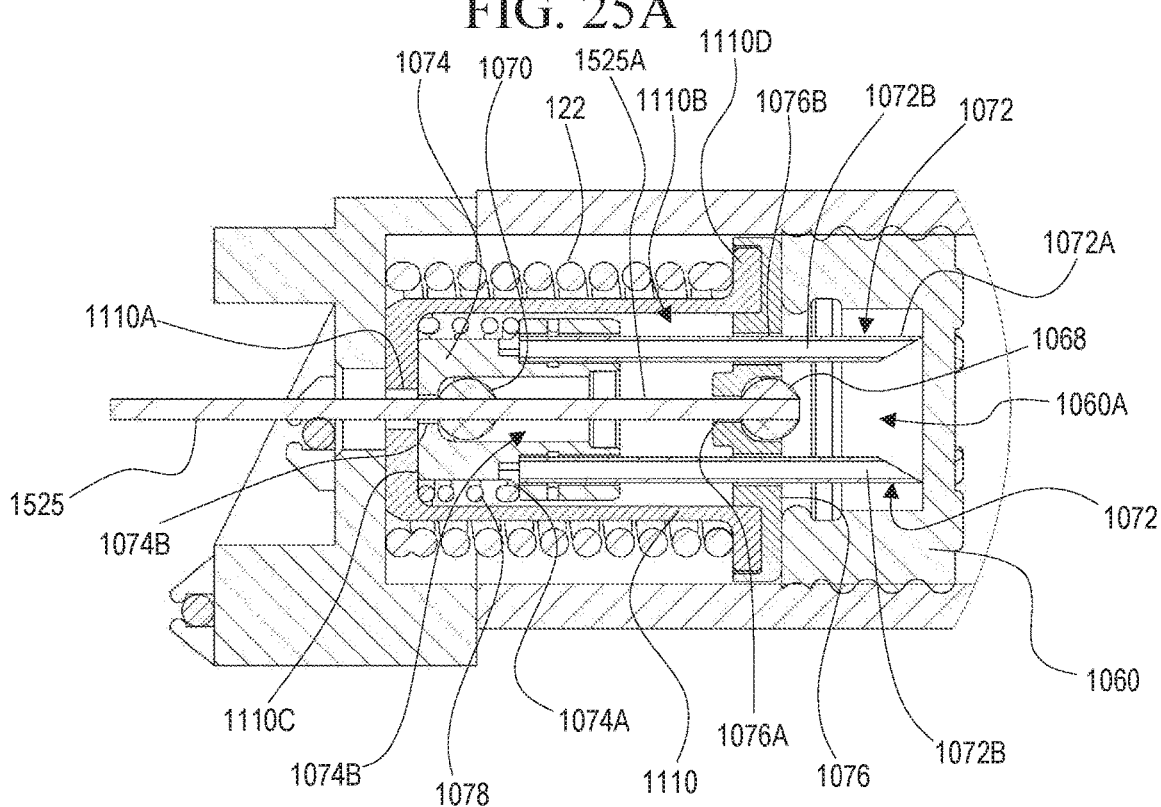
FIG. 25B is an enlarged, fragmentary, cross-sectional view of the safety mechanism of FIG. 25A in an initial configuration.
Figure 26A:
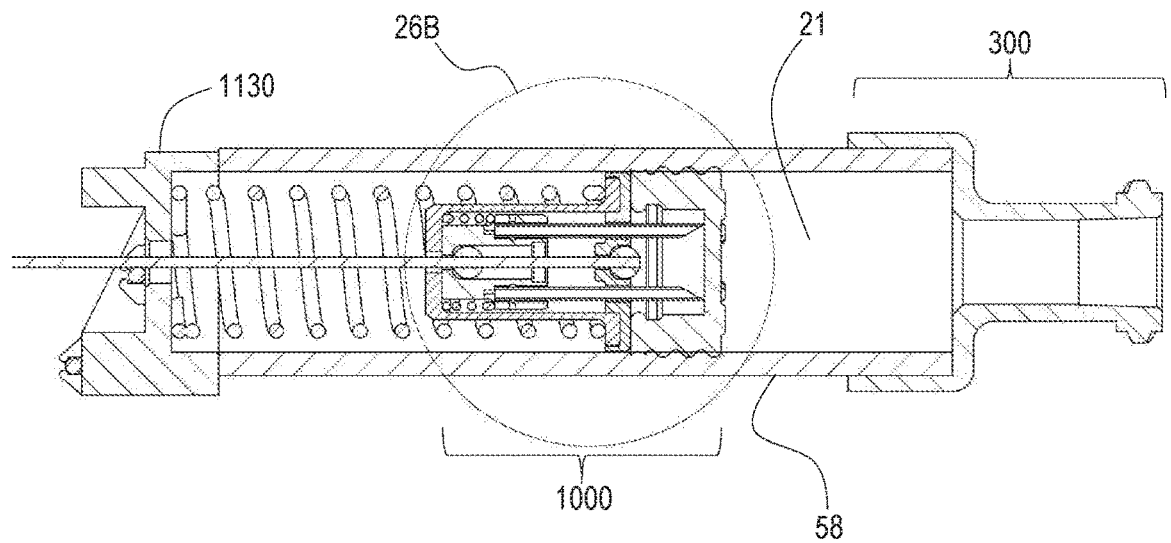
FIG. 26A is a cross-sectional view of a safety mechanism of FIG. 25A in an actuated configuration.
Figure 26B:
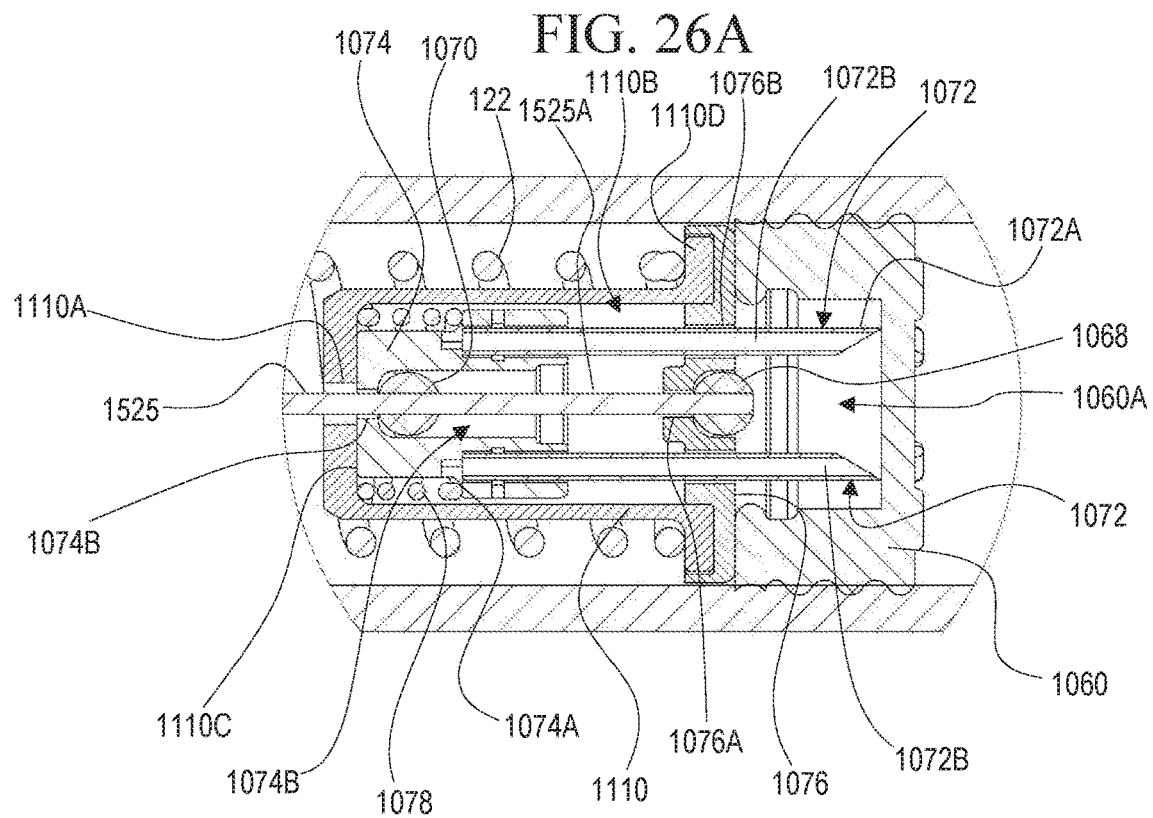
FIG. 26B is an enlarged, fragmentary, cross-sectional view of the safety mechanism of FIG. 26A in the actuated configuration.

In an initial configuration, as shown in FIGS. 25A-25B, the safety biasing member 1078 is held in a compressed or energized state between a portion of hub 1074 such as shoulder 1074A and an internal face 1110C of the piston 1110 by tension in the tether 1525. In the embodiment shown, tension of the tether 1525 restricts motion of the hub 1074 by way of the proximal plug 1070 disposed in a cavity 1074B of the hub 1074. The stiffness of the safety biasing member 1078 is such that during normal operation the tension in the tether 1525 is sufficient to prevent decompression of the safety biasing member 1078. Hence, during normal operation, the hub 1074 and the one or more piercing members 1072 do not translate with respect to the piston 1110. In the absence of a failure or fault of the drive mechanism tension will be sustained in the tether 1525 and the safety biasing member 1078 will be prevented from decompressing throughout the drug delivery process. The distal plug 1068 may be positioned distal to at least a portion of the safety mechanism base 1076. Hence, the tension of the tether 1525 is transmitted to the plunger seal piercing mechanism 1000 by both the distal 1068 and proximal 1070 plugs. The piston 1110 may include a flange 1110D disposed between the plunger seal 1060 and the drive biasing member 122. Alternatively, the drive biasing member 122 may act on the safety mechanism base 1076. Motion of the drive biasing member 122 is transmitted through the flange 1110D of the piston 1110 and/or the safety mechanism base 1076 to the plunger seal 1060. This also allows decompression of the drive biasing member 122 and translation of the plunger seal 1060 to be restricted by the tether 1525. FIGS. 26A-26B show the drive biasing member 122 in a partially decompressed state in which the plunger seal 1060 has translated distally within the barrel 58.

Figure 27A:
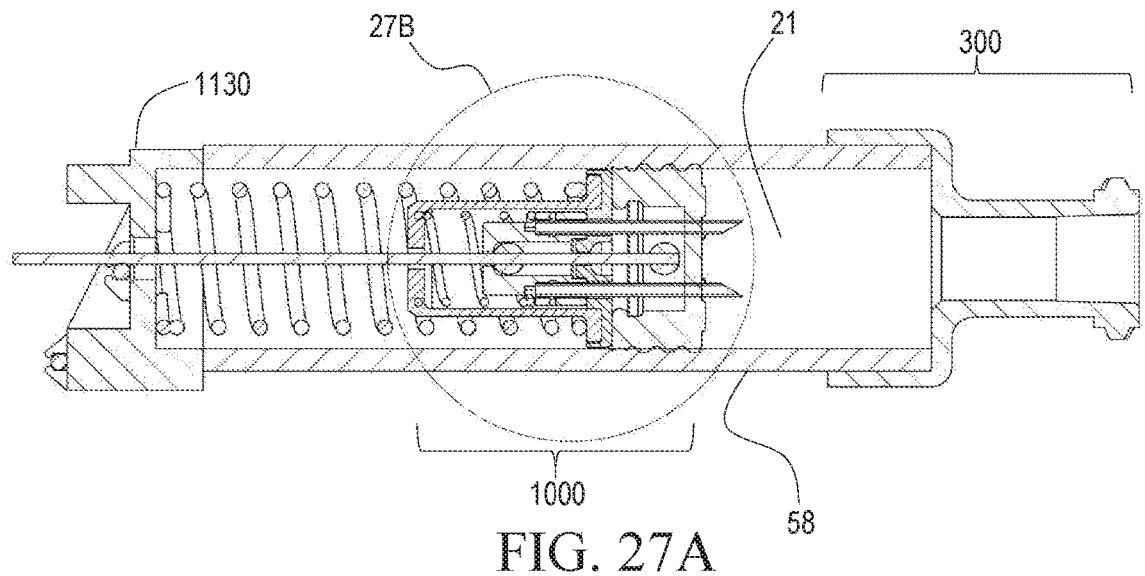
FIG. 27A is a cross-sectional view of a safety mechanism of FIG. 25A in a retracted configuration.
Figure 27B:
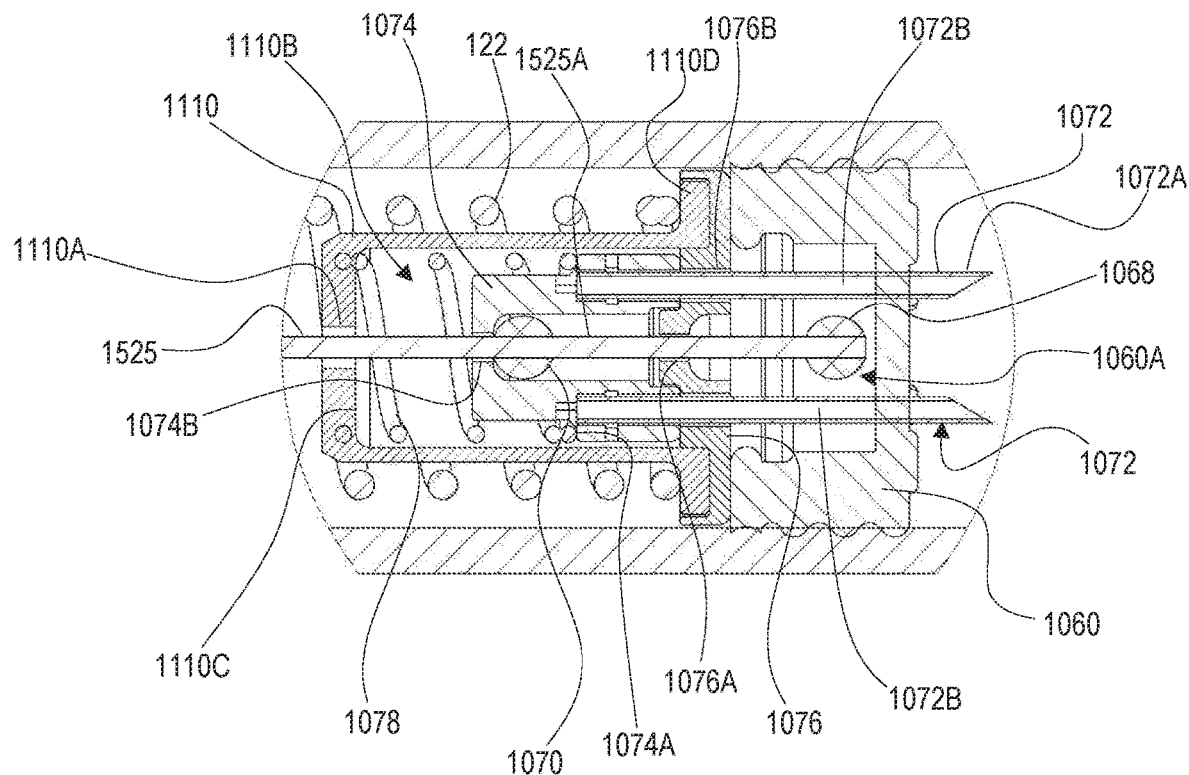
FIG. 27B is an enlarged, fragmentary, cross-sectional view of the safety mechanism of FIG. 27A in the retracted configuration.

In the event of failure of the drive mechanism or regulating mechanism, and a resulting reduction in tension in the tether, the safety biasing member 1078 is able to decompress or de-energize. As shown in FIGS. 27A-27B, this decompression of the safety biasing member 1078 causes the hub 1074 and the one or more piercing members 1072 to translate in the distal direction with respect to the piston 1110. As a result, the distal end 1072A of the one or more piercing members 1072 pierces the plunger seal 1060. Upon piercing of the plunger seal 1060, a fluid pathway is created from the drug chamber 21, through or around the one or more piercing members 1072, and into the piston 1110, proximal portion of the barrel 58, or another aspect of the drug pump 10. Because the fluid pathway through or around the one or more piercing members 1072 has a lower pressure (i.e., is a fluid path of lower resistance) than the fluid pathway through the sterile fluid pathway connection 300, continued translation of the plunger seal 1060 toward the distal end of the barrel 58 will result in the fluid drug traveling through or around the one or more piercing members 1072. Thus, the volume of drug delivered through the sterile fluid pathway connection 300 and delivered to the target will be reduced or terminated. In this way, the safety mechanism 1000 may reduce or eliminate the risk of a runaway fluid delivery scenario, thereby increasing the safety of the device.

As noted above, the tether 1525 may directly or indirectly restrict translation of the piston 1110 at one or more locations. For example, in the embodiment shown in FIGS. 25A-27B, the tether 1525 may restrict translation of the piston 1110 at the distal plug 1068 and proximal plug 1070 wherein the distal 1068 and proximal 1070 plugs are separated by an intermediate portion 1525A of the tether 1525. This may provide additional, redundant safety mechanisms. For example, if a failure occurs at the distal plug 1068 or in the intermediate portion 1525A of the tether 1525, the rate of decompression of the drive biasing member 122 will continue to be restricted due to engagement of the tether 1525 with the piston 1110 at the proximal plug 1070. Failure of the drive mechanism or tether 1525 proximal to the proximal plug 1070 will result in decompression of the safety biasing member 1078, piercing of the plunger seal 1060 by the one or more piercing members 1072, and a restriction or reduction in flow of drug fluid to the target as described above. The intermediate portion 1525A may be an integral portion of the tether 1525 or may be a separate component that is directly or indirectly coupled to the tether 1525.

During normal operation, the components of the plunger seal piercing mechanism 1000 do not come in contact with the drug. Additionally, in the event of activation of the plunger seal piercing mechanism 1000, the fluid that passes through or around the one or more piercing members 1072 will not be delivered to the target. Therefore, components of the plunger seal piercing mechanism 1000 do not require sterilization although they may be configured for sterilization if desired.

A method of manufacture of a plunger seal piercing mechanism includes one or more of the steps of: passing a tether 1525 through an aperture 1110A of a piston 1110; affixing one or more piercing members 1072 to a hub 1074; positioning a safety biasing member 1078 against an internal proximal face 1110C of the piston 1110; passing the tether 1525 through an aperture 1074B of the hub 1074; securing a proximal plug 1070 to the tether 1525; passing the tether 1525 through a central aperture 1076A of the safety base 1076; securing a distal plug 1068 to the tether 1525.

Figure 28A:
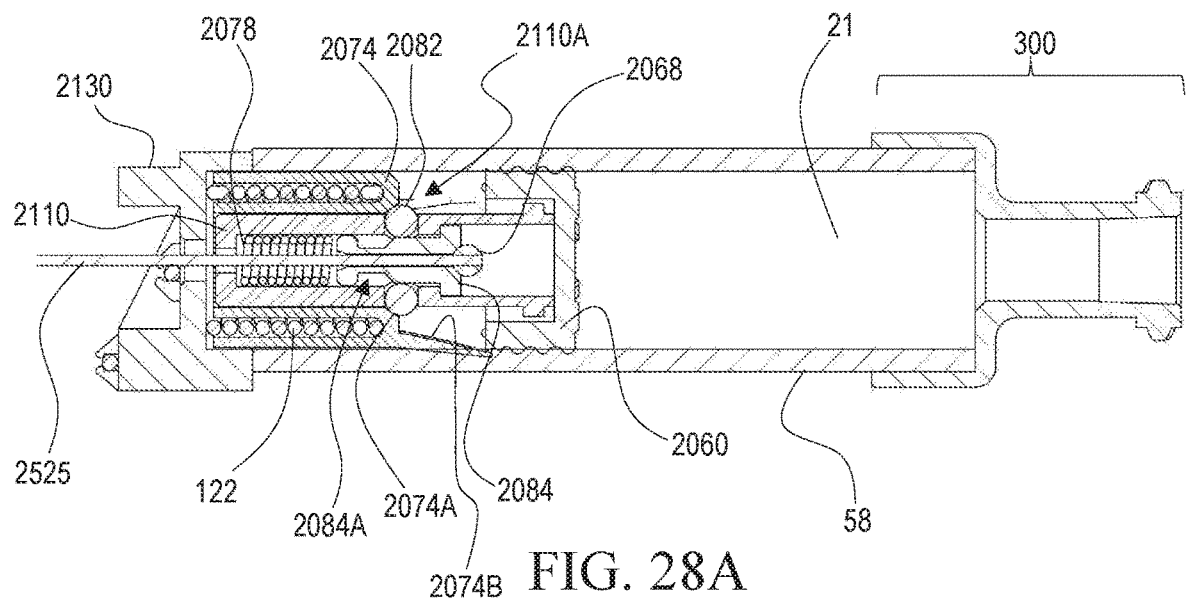
FIGS. 28A-28B are cross-sectional views of a safety mechanism according to another embodiment of the present invention.
Figure 28B:
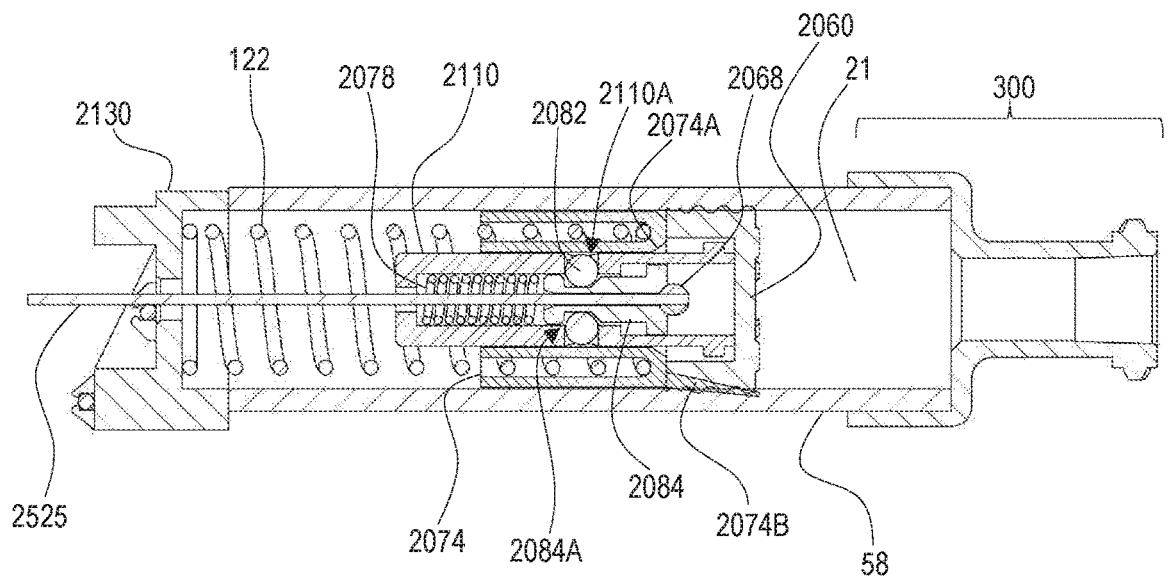
Figure 31:
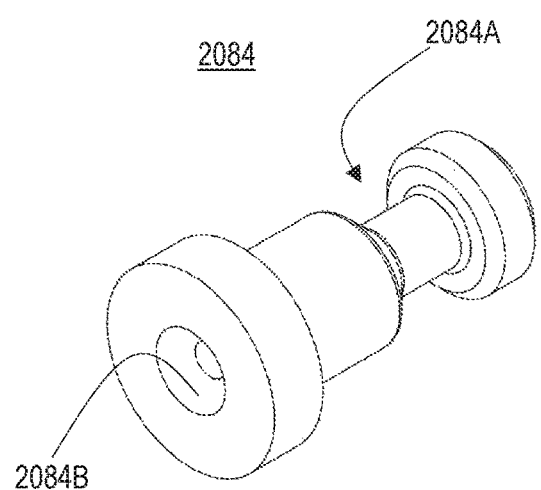
FIG. 31 is an isometric view of a sleeve for the safety mechanism of FIGS. 28A-28B.

In another embodiment, shown in FIGS. 28A-28B, the safety mechanism is a plunger seal displacing mechanism 2000. The displacing mechanism includes piston 2110, spring retainer 2074, sleeve 2084, safety biasing member 2078, plug 2068, and one or more transfer elements 2082. The plug 2068 may be fixedly engaged with the tether 2525. Further, plug 2068 may be positioned distal with respect to at least a portion of the sleeve 2084 such that the plug 2068 restricts distal displacement of the sleeve 2084. For example, plug 2068 may be disposed in recess 2084B of sleeve 2084 (shown in FIG. 31). The safety biasing member 2078 is positioned between the piston 2110 and the sleeve 2084 and is initially prevented from decompressing and/or de-energizing due to the restriction of displacement of the sleeve 2084. In an initial position, the transfer elements 2082 are disposed within apertures 2110A of the piston and are retained in that position by contact with the sleeve 2084. The transfer elements 2082 are also in contact with a portion of the spring retainer 2074—such as the contact surface 2074A—and, thereby, prevent translation of the spring retainer 2074 relative to the piston 2110. Hence, the force imparted on the spring retainer 2074 by the drive biasing member 122 is transferred through the transfer elements 2082 to the piston 2110 and from the piston 2110 to the plunger seal 2060. The contact surface 2074A of the spring retainer 2074 may be angled such that it applies a force to the transfer elements 2082 that is at least partially in an inward, radial direction.

Upon failure or fault of the drive mechanism or the tether, the safety biasing member 2078 will no longer be restricted from decompressing by tension in the tether. The decompression of the safety biasing member 2078 causes the sleeve 2084 to translate in the distal direction with respect to the piston 2110. As the sleeve 2084 translates, the receiving slot 2084A of the sleeve 2084 becomes aligned with the transfer elements 2082. When so aligned, the force applied to the transfer elements 2082 by the spring retainer 2074 causes the transfer elements 2082 to drop into the receiving slot 2084A. In this position, the transfer elements 2082 no longer prevent axial, distal translation of the spring retainer 2074 with respect to the piston 2110. Because of this, and in response to continued decompression of the drive biasing member 122, the spring retainer 2074 translates distally with respect to the piston 2110, allowing the prongs 2074B of the spring retainer 2074 to contact the plunger seal 2060.

Figure 29:
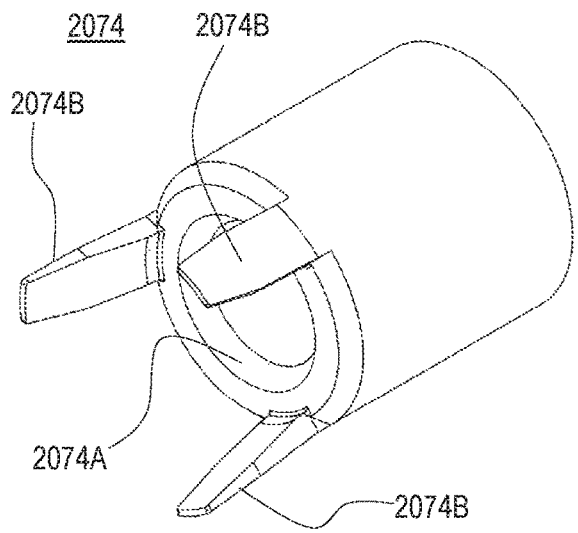
FIG. 29 is an isometric view according to one embodiment of a spring retainer for the safety mechanism of FIGS. 28A-28B.
Figure 30:
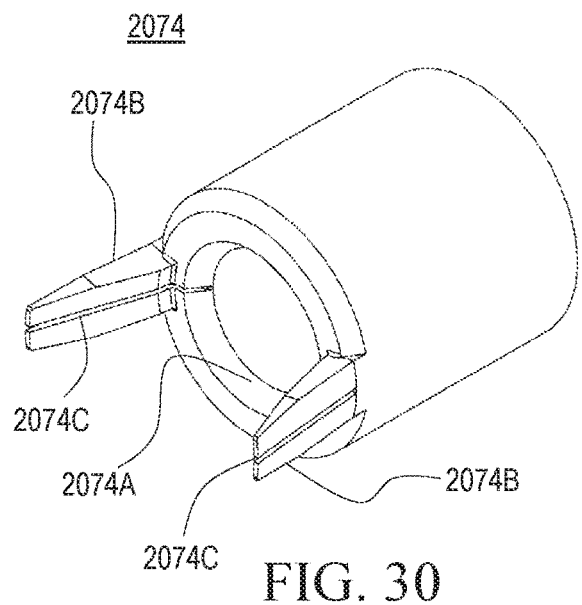
FIG. 30 is an isometric view according to another embodiment of a spring retainer for the safety mechanism of FIGS. 28A-28B.

The spring retainer 2074 may include any number of prongs 2074B and preferably includes two or three prongs. The prongs 2074B may be equally spaced around the circumference of the spring retainer 2074 or, alternatively, may be unequally spaced. As shown in FIGS. 29-30, the prongs 2074B may include a ramped surface. Contact of the ramped surface with the plunger seal 2060 may cause inwardly radial displacement of the plunger seal 2060. This displacement of the plunger seal 2060 may cause at least a partial loss of contact with the barrel 58, allowing the contents of the barrel to flow past the seal 2060 and into the proximal portion of the barrel 58. Continued distal translation of the plunger seal 2060 will result in the contents of the barrel flowing past the seal due to this being a flow path of lesser resistance than the flow path through the sterile fluid pathway connection 300. The prongs 2074B of the spring retainer 2074 may include bypass features 2074C such as slots or scallops that facilitate the flow of fluid past the plunger seal 2060.

In another embodiment, the spring retainer 2074 is configured to cause the plunger seal 2060 to skew within the barrel upon contact (i.e., cause the central axis of the plunger seal to not be parallel to the central axis of the barrel). This allows the contents of the barrel 58 to flow past the plunger seal 2060 and restricts or eliminates further delivery to the target. To cause the skewing of the plunger seal 2060, the spring retainer 2074 may be configured such that it applies pressure to the plunger seal 2060 unevenly such as, for example, by only having a single prong 2074B.

Other forms of safety mechanisms may be used to ensure that the contents of the drug container are not delivered at too high a rate. For example, the fluid pathway connection may include a pressure relief or "blowoff" valve which opens in response to increased pressure within the fluid pathway. This increased pressure may be caused by the plunger seal distally translating at too rapid of a rate. With the valve in the open position, the delivery of the drug fluid to the target may be terminated or reduced.

Assembly and/or manufacturing of controlled delivery drive mechanism 100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the target. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 may guide the insertion of the piercing member of the fluid pathway connection into the barrel 58 of the drug container 50. The drug container 50 may then be mounted to a distal end of drive housing 130.

One or more drive biasing members 122 may be inserted into a distal end of the drive housing 130. Optionally, a cover sleeve may be inserted into a distal end of the drive housing 130 to substantially cover biasing member 122. A piston may be inserted into the distal end of the drive housing 130 such that it resides at least partially within an axial passthrough of the biasing member 122 and the biasing member 122 is permitted to contact a piston interface surface 110C of piston 110 at the distal end of the biasing member 122. An optional cover sleeve may be utilized to enclose the biasing member 122 and contact the piston interface surface 110C of piston 110. The piston 110 and drive biasing member 122, and the optional cover sleeve, may be compressed into drive housing 130. Such assembly positions the drive biasing member 122 in an initial compressed, energized state and preferably places a piston interface surface 110C in contact with the proximal surface of the plunger seal 60 within the proximal end of barrel 58. The piston, piston biasing member, contact sleeve, and optional components, may be compressed and locked into the ready-to-actuate state within the drive housing 130 prior to attachment or mounting of the drug container 50. The tether 525 is pre-connected to the piston 110 and passed through the axial aperture of the biasing member 122 and drive mechanism housing 130, and then wound through the interior of the drug pump with the other end of the tether 525 wrapped around the winch drum 520B of the regulating mechanism 500.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the target. The components which constitute the pathway for fluid flow are now assembled. These components may be sterilized, by a number of known methods, and then mounted either fixedly or removably to an assembly platform 20 or housing 12 of the drug pump, as shown in FIG. 1B.

Certain optional standard components or variations of drive mechanism 100 or drug pump 10 are contemplated while remaining within the breadth and scope of the present invention. For example, the embodiments may include one or more batteries utilized to power a motor or solenoid, drive mechanisms, and drug pumps of the present invention. A range of batteries known in the art may be utilized for this purpose. Additionally, upper or lower housings may optionally contain one or more transparent or translucent windows 18 to enable the user to view the operation of the drug pump 10 or verify that drug dose has completed. Similarly, the drug pump 10 may contain an adhesive patch and a patch liner on the bottom surface of the housing 12. The adhesive patch may be utilized to adhere the drug pump 10 to the target for delivery of the drug dose. As would be readily understood by one having ordinary skill in the art, the adhesive patch may have an adhesive surface for adhesion of the drug pump to the target. The adhesive surface of the adhesive patch may initially be covered by a non-adhesive patch liner, which is removed from the adhesive patch prior to placement of the drug pump 10 in contact with the target. Removal of the patch liner may further remove the sealing membrane 254 of the insertion mechanism 200, opening the insertion mechanism to the target for drug delivery.

Similarly, one or more of the components of controlled delivery drive mechanism 100 and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the controlled delivery drive mechanism and/or drug pump to each other. Alternatively, one or more components of the controlled delivery drive mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the controlled delivery drive mechanisms and drug pumps disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. The novel controlled delivery drive mechanisms of the present invention may be directly or indirectly activated by the user. Furthermore, the novel configurations of the controlled delivery drive mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. Furthermore, the embodiments of the present invention permit device architecture and/or component integration in ways which are not suitable for devices that require terminal sterilization. For example, when sterilization of the entire device is necessary, the device architecture often requires adequate spacing of components to permit the sterilization gas or material to effectively reach the target surfaces. Removing the need for terminal sterilization permits reduction or elimination of those spaces and allows for device architectures that offer smaller overall dimensions, human factors benefits, and/or industrial design options that are not available for devices that require terminal sterilization.

Manufacturing of a drug pump includes the step of attaching both the controlled delivery drive mechanism and drug container, either separately or as a combined component, to an assembly platform or housing of the drug pump. The method of manufacturing further includes attachment of the fluid pathway connection, drug container, and insertion mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device. The method of assembly of the drug pump may further include positioning a safety mechanism such as a plunger seal piercing mechanism at least partially within the barrel and adjacent to or in contact with the plunger seal.

A method of operating the drug pump includes the steps of: activating, by a user, the activation mechanism; displacing a control arm to actuate an insertion mechanism; and actuating a power and control system to activate a controlled delivery drive mechanism to drive fluid drug flow through the drug pump according to a controlled rate or drug delivery profile. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the controlled delivery drive mechanism by the expansion of the biasing member acting upon a piston within a drug container to force fluid drug flow through the drug container, the fluid pathway connection, a sterile fluid conduit, and the insertion mechanism for delivery of the fluid drug to the target, wherein a regulating mechanism acting to restrain the distribution of a tether is utilized to meter the free axial translation of the piston. The method of operation of the drive mechanism and the drug pump may be better appreciated with reference to FIGS. 2A-2E and FIGS. 3A-3D, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

The invention claimed is:

1. A drug delivery pump, comprising:
a drug container including a barrel and a plunger seal;
a needle insertion mechanism;
a fluid pathway connection; and
a drive mechanism including:
a tether,
an electrical actuator,
a gear interface, rotation of the gear interface being controlled by the electrical actuator,
a gear assembly in rotational engagement with the gear interface, the gear assembly including a main gear and a regulating mechanism, wherein release of the tether is metered by operation of the gear assembly through the regulating mechanism,
a drive housing,
a piston connected to the tether and configured for disposition in the barrel adjacent the plunger seal, the piston being configured to translate substantially axially within the drug container, and
a biasing member configured for disposition at least partially within the barrel, the biasing member being retained in an energized state between the piston and drive housing, and
wherein the release of the tether controls the free expansion of the biasing member from its energized state and the free axial translation of the piston upon which the biasing member bears upon,
wherein the gear interface is configured such that a force applied to the gear interface by the gear assembly does not impart a torque causing the gear interface to rotate.

2. A drug delivery pump comprising:
a drug container including a barrel and a plunger seal;
a needle insertion mechanism;
a fluid pathway connection;
a drive mechanism including:
a tether,
an electrical actuator,
a gear interface, rotation of the gear interface being controlled by the electrical actuator,
a gear assembly in rotational engagement with the gear interface, the gear assembly including a main gear and a regulating mechanism, wherein release of the tether is metered by operation of the gear assembly through the regulating mechanism,
a drive housing,
a piston connected to the tether and configured for disposition in the barrel adjacent the plunger seal, the piston being configured to translate substantially axially within the drug container,
a biasing member configured for disposition at least partially within the barrel, the biasing member being retained in an energized state between the piston and the drive housing, and
wherein the release of the tether controls the free expansion of the biasing member from its energized state and the free axial translation of the piston upon which the biasing member bears upon;
an activation mechanism;
a slide; and
a selector member disposed between the drive mechanism and the needle insertion mechanism (NIM),
wherein actuation of the activation mechanism causes translation of the slide and wherein the drive mechanism causes the selector member to be positioned such that contact between the slide and the selector member causes at least a portion of the slide to be displaced bringing the slide into contact with a throw arm which is caused to translate with the slide the translation of the throw arm causing needle insertion by the NIM.

3. The drug delivery pump of claim 2, wherein the throw arm causes displacement of a NIM interlock which, in an initial configuration, prevents rotation of a NIM retainer, wherein the NIM retainer initially prevents activation of needle insertion.

4. The drug delivery pump of claim 2, wherein after translation of the NIM interlock, an aperture of the NIM interlock is aligned with a portion of the NIM retainer, allowing rotation of the NIM retainer, the rotation of which permits needle insertion by the NIM.

5. A drug deliver pump, comprising:
a drug container including a barrel and a plunger seal;
a needle insertion mechanism;
a fluid pathway connection;
a drive mechanism including:
a tether,
an electrical actuator,
a gear interface, rotation of the gear interface being controlled by the electrical actuator,
a gear assembly in rotational engagement with the gear interface, the gear assembly including a main gear and a regulating mechanism, wherein release of the tether is metered by operation of the gear assembly through the regulating mechanism,
a drive housing,
a piston connected to the tether and configured for disposition in the barrel adjacent the plunger seal, the piston being configured to translate substantially axially within the drug container,
a biasing member configured for disposition at least partially within the barrel, the biasing member being retained in an energized state between the piston and the drive housing, and
wherein the release of the tether controls the free expansion of the biasing member from its energized state and the free axial translation of the piston upon which the biasing member bears upon; and
a safety mechanism which is configured to terminate or slow delivery of the drug fluid through the fluid pathway connection upon a loss of tension in the tether.

6. A drug delivery pump, comprising:
a drug container including a barrel and a plunger seal;
a needle insertion mechanism;
a fluid pathway connection; and
a drive mechanism including:
a tether,
an electrical actuator,
a gear interface, rotation of the gear interface being controlled by the electrical actuator,
a gear assembly in rotational engagement with the gear interface, the gear assembly including a main gear and a regulating mechanism, wherein release of the tether is metered by operation of the gear assembly through the regulating mechanism,
a drive housing,
a piston connected to the tether and configured for disposition in the barrel adjacent the plunger seal, the piston being configured to translate substantially axially within the drug container,
a biasing member configured for disposition at least partially within the barrel, the biasing member being retained in an energized state between the piston and the drive housing, and
wherein the release of the tether controls the free expansion of the biasing member from its energized state and the free axial translation of the piston upon which the biasing member bears upon; and
wherein the gear interface is a key wherein the key has a first flange having a first aperture and a second flange having a second aperture, the first flange being axially offset from the second flange.

7. The drug delivery pump of claim 6, wherein the first aperture is circumferentially offset from the second aperture.

8. The drug delivery pump of claim 6, wherein the first aperture is circumferentially aligned with the second aperture.

* * * * *